(12) United States Patent
Sames et al.

(10) Patent No.: US 9,988,377 B2
(45) Date of Patent: Jun. 5, 2018

(54) SMALL MOLECULE INDUCERS OF GDNF AS POTENTIAL NEW THERAPEUTICS FOR NEUROPSYCHIATRIC DISORDERS

(75) Inventors: Dalibor Sames, New York, NY (US); Xiaoguang Li, Stillwater, MN (US); Shu Li, Stillwater, MN (US); Andrew Kruegel, New York, NY (US); Richard Karpowicz, Philadelphia, PA (US); Ignacio Carrera, Montevideo (UY); Souvik Rakshit, Urbana, IL (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 436 days.

(21) Appl. No.: 14/240,681

(22) PCT Filed: Aug. 24, 2012

(86) PCT No.: PCT/US2012/052327
§ 371 (c)(1),
(2), (4) Date: Nov. 7, 2014

(87) PCT Pub. No.: WO2013/028999
PCT Pub. Date: Feb. 28, 2013

(65) Prior Publication Data
US 2015/0056699 A1 Feb. 26, 2015

Related U.S. Application Data

(60) Provisional application No. 61/526,839, filed on Aug. 24, 2011.

(51) Int. Cl.
*C07D 453/06* (2006.01)
(52) U.S. Cl.
CPC ................. *C07D 453/06* (2013.01)
(58) Field of Classification Search
CPC .................................................. C07D 453/06
See application file for complete search history.

(56) References Cited

U.S. PATENT DOCUMENTS

| 3,716,528 A | 2/1973 | Nagata et al. |
| 5,869,672 A | 2/1999 | Kozikowski et al. |

(Continued)

FOREIGN PATENT DOCUMENTS

| EP | 0468562 A1 | 1/1992 |
| WO | WO 2006/023821 A2 | 3/2006 |

(Continued)

OTHER PUBLICATIONS

Levi, et al. Document No. 142:74753, retrieved from CAPLUS; (2004).*

(Continued)

*Primary Examiner* — Shawquia Jackson
(74) *Attorney, Agent, or Firm* — John P. White; Cooper & Dunham LLP

(57) ABSTRACT

This invention provides a compound having the structure

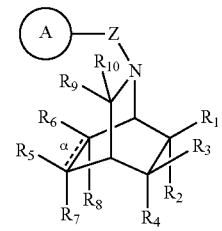

wherein
A is a ring structure, with or without substitution;
Z is present or absent and when present is

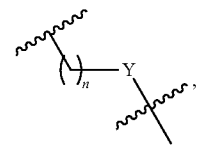

wherein
n is 0, 1, 2, 3, or 4;
Y is —$(CR_{11}R_{12})$—, —$NH(CR_{11}R_{12})$—, or —$O(CR_{11}R_{12})$—,
wherein $R_{11}$ and $R_{12}$ are each hydrogen or combine to form a carbonyl;
$R_1$, $R_2$, $R_3$, $R_4$, $R_5$ and $R_6$ are independently H, substituted or unsubstituted alkyl, substituted or unsubstituted aryl, substituted or unsubstituted heteroalkyl, substituted or unsubstituted heteroaryl, hydroxyl, amino, ester or amide;
α represents a bond, which is present or absent and when α is present, then $R_7$ and $R_8$ are absent;
$R_7$ and $R_8$ are present when α is absent and are independently H, substituted or unsubstituted alkyl, substituted or unsubstituted aryl, substituted or unsubstituted heteroalkyl, substituted or unsubstituted heteroaryl, hydroxyl, amino, ester, amide or $R_5$ and $R_7$ combine to form a carbonyl or $R_6$ and $R_8$ combine to form a carbonyl;
$R_9$ and $R_{10}$ are each hydrogen or combine to form a carbonyl; and
when α is present, Z is (Continued)

where n=1, Y is —(CR$_{11}$R$_{12}$)— where R$_{11}$ and R$_{12}$ are H, A is unsubstituted indole attached at the 3-position of the indole, R$_3$, R$_4$, R$_5$, R$_6$, R$_9$ and R$_{10}$ are each H, and one of R$_1$ or R$_2$ is H, then the other one of R$_1$ or R$_2$ is other than H or ethyl, or a pharmaceutically acceptable salt, diastereomer, or enantiomer thereof.

26 Claims, 19 Drawing Sheets

(56) References Cited

U.S. PATENT DOCUMENTS

| | | |
|---|---|---|
| 8,337,941 B2 | 12/2012 | Gubernator et al. |
| 8,741,891 B1 | 6/2014 | Mash |
| 9,075,014 B2 | 7/2015 | Sames et al. |
| 2008/0194522 A1 | 8/2008 | Chen et al. |
| 2010/0035279 A1 | 2/2010 | Gubernator et al. |
| 2013/0171664 A1 | 7/2013 | Sames et al. |
| 2013/0190497 A1 | 7/2013 | Gubernator et al. |
| 2017/0217913 A1 | 8/2017 | Kruegel et al. |

FOREIGN PATENT DOCUMENTS

| | | |
|---|---|---|
| WO | WO 2006/026368 A2 | 3/2006 |
| WO | WO 2007/022263 A1 | 2/2007 |
| WO | WO/2008/013997 A2 | 1/2008 |
| WO | WO 2011/094560 A1 | 8/2011 |
| WO | WO 2013/029999 A1 | 2/2013 |
| WO | WO 2015/138791 A1 | 9/2015 |
| WO | WO/2016/086158 A1 | 6/2016 |
| WO | WO 2017/165738 A1 | 9/2017 |

OTHER PUBLICATIONS

Poletto, et al. Document No. 79:132894, retrieved from CAPLUS; (1973).*

Levi, et al. Document No. 143:248545, retrieved from CAPLUS (2005).*

Levi, et al. Document No. 143:248545, retrieved from CAPLUS; (2005).*

Trost. Document No. 92:6781, retrieved from CAPLUS; (1979).*

Jana, et al. Tetrahedron Letters 51 (2010) 1441-1443.*

Registry No. 663195-14-0, entered in STN on Mar. 15, 2004.*

International Search Report dated Oct. 26, 2012 in connect on with International Application PCT/US2012/052327.

Written Opinion of the International Search Authority dated Oct. 26, 2012 in connection with International Application PCT/US2012/052327.

International Preliminary Report on Patentability dated Feb. 25, 2014, in connection with International Application PCT/US2012/052327.

Notification Concerning Transmittal of International Preliminary Report on Patentability (Chapter I of the Patent Cooperation Treaty), including an International Preliminary Report on Patentability and Written Opinion of the International Searching Authority, dated Mar. 6, 2014 by the International Bureau of WIPO in connection with PCT International Application No. PCT/US2012/052327, filed Aug. 24, 2012.

Nakano et al. (2010). A novel chiral oxazolidine organocatalyst for a synthesis of oseltamivir intermediate using a highly enantioselective Diels-Alder reaction of 1,2-dihyrdopyridine. *Chemical Communications*, 46(26), 4827-4829.

Eketjäll et al. (1999). Distinct structural elements in GDNF mediate binding to GFRα1 and activation of the GFRα1—c-Ret receptor complex. *The EMBO Journal*, 18(21), 5901-5910.

Johnstone et al. (1979). A Rapid, Simple, and Mild Procedure for Alkylation of Phenols, Alcohols, Amides and Acids. *Tetrahedron*, 35(18), 2169-2173.

Notification of Transmittal of the International Search Report and the Written Opinion of the International Searching Authority, or the Declaration, including an International Search Report and Written Opinion of the International Searching Authority, dated Oct. 26, 2012 in connection with PCT International Application No. PCT/US2012/052327, filed Aug. 24, 2012.

International Search Report dated Feb. 5, 2016 in connection with International Application PCT/US2015/062726.

Notification of Transmittal of the International Search Report and the Written Opinion of the International Searching Authority, or Declaration dated Feb. 5, 2016 in connection with International Application PCT/US2015/062726.

Written Opinion of the International Search Authority dated Feb. 5, 2016 in connection with International Application PCT/US2015/062726.

Paul, S. et al. (2011) "Synthesis of new series of iboga analogues." Tetrahedron Letters 52, 6166-6169.

Kruegel et al. "Constructing Iboga Alkaloids via C-H Bond Functionalization: Examination of the Direct and Catalytic Union of Heteroarenes and Isoquinuclidine Alkenes" J. Org. Chem. 2015, 80, 2062-2071.

* cited by examiner

SMALL MOLECULE INDUCERS OF GDNF AS POTENTIAL NEW THERAPEUTICS FOR NEUROPSYCHIATRIC DISORDERS

CROSS-REFERENCE TO RELATED APPLICATIONS

This application is a § 371 national stage of PCT International Application No. PCT/US2012/052327, filed Aug. 24, 2012, claiming the benefit of U.S. Provisional Application No. 61/526,839, filed Aug. 24, 2011, the contents of each of which are hereby incorporated by reference in their entirety.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Neurotrophic factors play important roles not only in the development of the nervous system, but also in maintenance of its function and plasticity. GDNF (Glial cell line-Derived Neurotrophic Factor) is essential for growth, development and plasticity of dopamine and motor neurons as well as other brain cell populations (Airaksinen, M. S. et al. 2002). In the brain, GDNF is released by both neurons and glia cells. Although the signaling mechanisms underlying the expression and release of GDNF are not fully mapped, the released GDNF exerts its function on the brain cells and neurocircuitry through a receptor complex, comprised of GFRα1 (GDNF Family Receptor α1) and receptor tyrosine kinase RET (Trupp, M. et al. 1997). On the basis of the trophic and repair effects GDNF has on neural cells, it was considered as a potential therapeutic agent for several neurological disorders. However, GDNF is a protein and thus not readily administered to the brain. Consequently, small molecule inducers of GDNF release are of interest as potential therapeutics, most notably in the context of Parkinson's disease and neuropathic pain. In the latter case, GDNF's effectiveness has been ascribed to the ability of GDNF signaling to reset the function of several sodium channel subunits (modified in response to injury) (Boucher, T. J. et al. 2000).

Recently, it has been shown that GDNF (Glial cell line-Derived Neurotrophic Factor) acts as a negative regulator of alcohol addiction in rodent behavioral models (Carnicella, S. et al. 2008) It has also been demonstrated that the small molecule agents, ibogaine and noribogaine, reduce self-administration and reinstatement of alcohol intake in rats and mice, and that this effect is dependent on the induction of GDNF in the VTA (Ventral Tegmental Area of midbrain) (He, D-Y. et al. 2005; Carnicella, S. et al. 2010). However, ibogaine is active at multiple CNS receptors, resulting in complex pharmacology and serious side effects. Therefore, compounds that act as selective GDNF inducers are desirable. In addition to alcohol, GDNF also counteracts behavioral and biochemical adaptations in mice chronically treated with cocaine and morphine (Messer, C. J. et al. 2000; Bolanos, C. A. et al. 2004). Therefore, the GDNF inducing compounds may also be effective against other substance use disorders (SUDs).

GDNF also plays an important role in cognition and the changes in GDNF levels have been associated with mood disorders and the treatment of depression (Takebayashi, M. et al. 2006). Consequently, GDNF inducers should be considered as potential therapeutics for depressive disorders.

Described herein is a new class of GDNF (Glial cell line-Derived Neurotrophic Factor) inducers based on the isoquinuclidine core (FIG. 1).

SUMMARY OF THE INVENTION

This invention provides a compound having the structure:

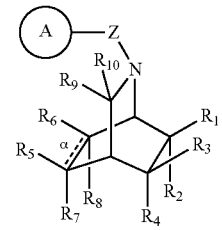

wherein
A is a ring structure, with or without substitution;
Z is present or absent and when present is

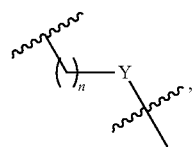

wherein
n is 0, 1, 2, 3, or 4;
Y is —(CR$_{11}$R$_{12}$)—, —NH(CR$_{11}$R$_{12}$)—, or —O(CR$_{11}$R$_{12}$)—,
wherein R$_{11}$ and R$_{12}$ are each hydrogen or combine to form a carbonyl;
R$_1$, R$_2$, R$_3$, R$_4$, R$_5$ and R$_6$ are independently H, substituted or unsubstituted alkyl, substituted or unsubstituted aryl, substituted or unsubstituted heteroalkyl, substituted or unsubstituted heteroaryl, hydroxyl, amino, ester or amide;
α represents a bond, which is present or absent and when α is present, then R$_7$ and R$_8$ are absent;
R$_7$ and R$_8$ are present when α is absent and are independently H, substituted or unsubstituted alkyl, substituted or unsubstituted aryl, substituted or unsubstituted heteroalkyl, substituted or unsubstituted heteroaryl, hydroxyl, amino, ester, amide or R$_5$ and R$_7$ combine to form a carbonyl or R$_6$ and R$_8$ combine to form a carbonyl;
R$_9$ and R$_{10}$ are each hydrogen or combine to form a carbonyl; and
when α is present, Z is

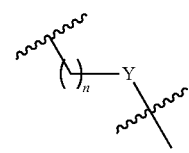

where n=1, Y is —(CR$_{11}$R$_{12}$)— where R$_{11}$ and R$_{12}$ are H, A is unsubstituted indole attached at the 3-position of the indole, R$_3$, R$_4$, R$_5$, R$_6$, R$_9$ and R$_{10}$ are each H, and one of R$_1$ or R$_2$ is H, then the other one of R$_1$ or R$_2$ is other than H or ethyl, or a pharmaceutically acceptable salt, diastereomer, or enantiomer thereof.

This invention provides a method for inducing a neural cell to release Glial cell-derived neurotrophic factor (GDNF) comprising contacting the cell with a compound having the structure:

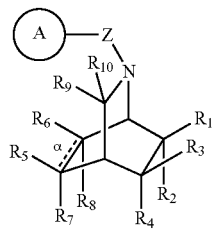

wherein
A is a ring structure, with or without substitution;
Z is present or absent and when present is

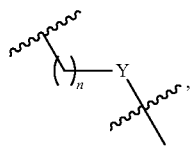

wherein
n is 0, 1, 2, 3, or 4;
Y is —(CR$_{11}$R$_{12}$)—, —NH(CR$_{11}$R$_{12}$)—, or —O(CR$_{11}$R$_{12}$)—,
  wherein R$_{11}$ and R$_{12}$ are each hydrogen or combine to form a carbonyl;
R$_1$, R$_2$, R$_3$, R$_4$, R$_5$ and R$_6$ are independently H, substituted or unsubstituted alkyl, substituted or unsubstituted aryl, substituted or unsubstituted heteroalkyl, substituted or unsubstituted heteroaryl, hydroxyl, amino, ester or amide;
α represents a bond, which is present or absent;
α represents a bond, which is present or absent and when α is present, then R$_7$ and R$_8$ are absent;
R$_7$ and R$_8$ are present when α is absent and are independently H, substituted or unsubstituted alkyl, substituted or unsubstituted aryl, substituted or unsubstituted heteroalkyl, substituted or unsubstituted heteroaryl, hydroxyl, amino, ester, amide or R$_5$ and R$_7$ combine to form a carbonyl or R$_6$ and R$_8$ combine to form a carbonyl;
R$_9$ and R$_{10}$ are each hydrogen;
when α is present, Z is

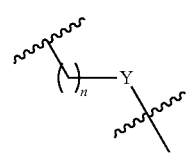

where n=1, Y is —(CR$_{11}$R$_{12}$)— where R$_{11}$ and R$_{12}$ are H, A is unsubstituted indole attached at the 3-position of the indole, R$_3$, R$_4$, R$_5$, R$_6$, R$_9$ and R$_{10}$ are each H, and one of R$_1$ or R$_2$ is H, then the other one of R$_1$ or R$_2$ is other than ethyl ester; and when α is present, Z is

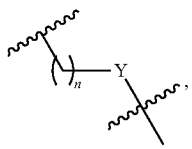

Y is —(CR$_{11}$R$_{12}$)—, one of R$_1$ or R$_2$ is ethyl, n=1 and R$_3$, R$_4$, R$_5$, R$_6$, R$_9$, R$_{10}$, R$_{11}$ and R$_{12}$ are each H, then A is other than unsubstituted thiophene attached at the 3-position of the thiophene or phenyl;

or a pharmaceutically acceptable salt, diastereomer, or enantiomer thereof.

DETAILED DESCRIPTION OF THE INVENTION

Figure 1:
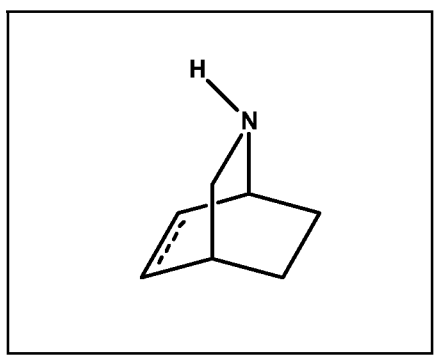
FIG. 1. Isoquinuclidine core structure.

This invention provides a compound having the structure:

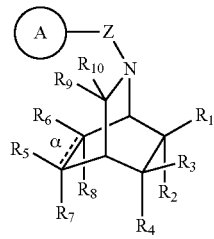

wherein
A is a ring structure, with or without substitution;
Z is present or absent and when present is

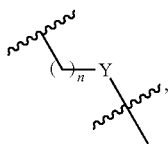

wherein
n is 0, 1, 2, 3, or 4;
Y is —($CR_{11}R_{12}$)—, —NH($CR_{11}R_{12}$)—, or —O($CR_{11}R_{12}$)—,
  wherein $R_{11}$ and $R_{12}$ are each hydrogen or combine to form a carbonyl;
$R_1$, $R_2$, $R_3$, $R_4$, $R_5$ and $R_6$ are independently H, substituted or unsubstituted alkyl, substituted or unsubstituted aryl, substituted or unsubstituted heteroalkyl, substituted or unsubstituted heteroaryl, hydroxyl, amino, ester or amide;
α represents a bond, which is present or absent and when α is present, then $R_7$ and $R_8$ are absent;
$R_7$ and $R_8$ are present when α is absent and are independently H, substituted or unsubstituted alkyl, substituted or unsubstituted aryl, substituted or unsubstituted heteroalkyl, substituted or unsubstituted heteroaryl, hydroxyl, amino, ester, amide or $R_5$ and $R_7$ combine to form a carbonyl or $R_6$ and $R_8$ combine to form a carbonyl;
$R_9$ and $R_{10}$ are each hydrogen or combine to form a carbonyl; and when (i) α is present, Z is

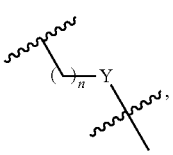

where n=1, Y is —($CR_{11}R_{12}$)— where $R_{11}$ and $R_{12}$ are H, A is unsubstituted indole attached at the 3-position of the indole, $R_3$, $R_4$, $R_5$, $R_6$, $R_9$ and $R_{10}$ are each H, and one of $R_1$ or $R_2$ is H, then (ii) the other one of $R_1$ or $R_2$ is other than H or ethyl,
or a pharmaceutically acceptable salt, diastereomer, or enantiomer thereof.

In some embodiments of the above compound,
when (i) α is present, Z is

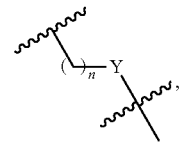

where n=1, Y is —($CR_{11}R_{12}$)— where $R_{11}$ and $R_{12}$ are H, A is unsubstituted indole attached at the 3-position of the indole, $R_3$, $R_4$, $R_5$, $R_6$, $R_9$ and $R_{10}$ are each H, and one of $R_1$ or $R_2$ is H, then (ii) the other one of $R_1$ or $R_2$ is other than ethyl ester; and
when (i) α is present, Z is

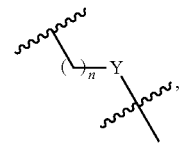

Y is —($CR_{11}R_{12}$)—, one of $R_1$ or $R_2$ is ethyl, n=1 and $R_3$, $R_4$, $R_5$, $R_6$, $R_9$, $R_{10}$, $R_{11}$ and $R_{12}$ are each H, then (ii) A is other than unsubstituted thiophene attached at the 3-position of the thiophene or phenyl;
or a pharmaceutically acceptable salt, diastereomer, or enantiomer thereof.

In some embodiments of the above compound, bond α is present.

In some embodiments of the above compound, bond α is absent.

In some embodiments, the ring structure A is an aromatic or non-aromatic monocycle, bicycle, mono-heterocycle, or bi-heterocycle, each with or without substitution,
or a pharmaceutically acceptable salt, diastereomer, or enantiomer thereof.

In some embodiments, ring structure A is phenyl, naphthalene, pyrrole, furan, thiophene, indole, benzofuran, benzothiophene, azaindole, benzimidazole, benzothiazole, or benzoxazole, each with or without substitution,
or a pharmaceutically acceptable salt, diastereomer, or enantiomer thereof.

In some embodiments, the ring structure A is

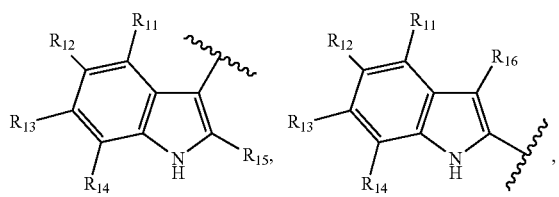

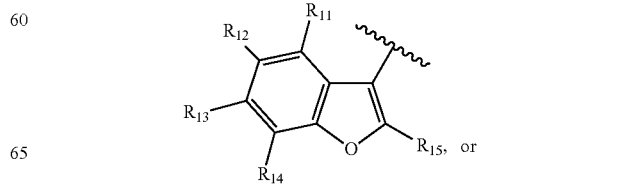

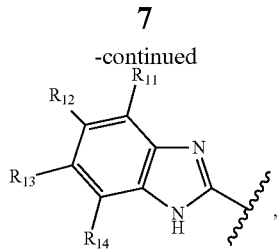

or a pharmaceutically acceptable salt, diastereomer, or enantiomer thereof.

In some embodiments, $R_{11}$, $R_{12}$, $R_{13}$, $R_{14}$ and $R_{15}$ are each independently H, alkyl, aryl, heteroalkyl, heteroaryl, ester, or halide, each with or without substitution,
or a pharmaceutically acceptable salt, diastereomer, or enantiomer thereof.

In some embodiments, $R_{12}$, $R_{13}$ and $R_{15}$ are each independently H, F, Cl, Br, $CH_3$, $CF_3$, OMe, $OCF_3$, $C(O)OR_{16}$, wherein $R_{16}$ is alkyl,
or a pharmaceutically acceptable salt, diastereomer, or enantiomer thereof.

In some embodiments, the ring structure A is,

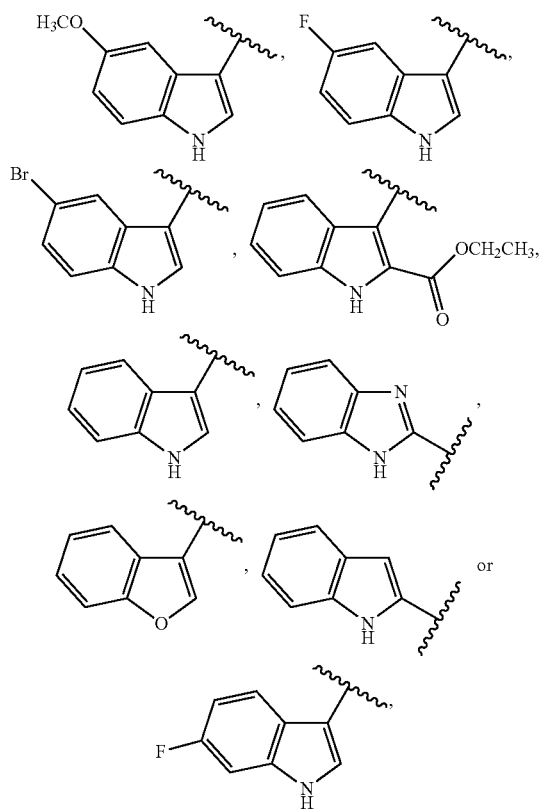

or a pharmaceutically acceptable salt, diastereomer, or enantiomer thereof.

In some embodiments, the compound wherein
wherein $R_{11}$ and $R_{14}$ are each independently H, F, Cl, Br, $CH_3$, $CF_3$, OMe, $OCF_3$, $C(O)OR_{16}$, wherein $R_{16}$ is alkyl,
or a pharmaceutically acceptable salt, diastereomer, or enantiomer thereof.

In some embodiments, the compound wherein the ring structure A is,

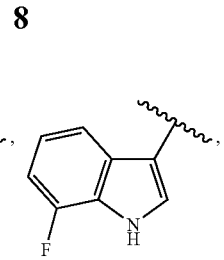

or a pharmaceutically acceptable salt, diastereomer, or enantiomer thereof.

In some embodiments, the compound wherein the ring structure A is,

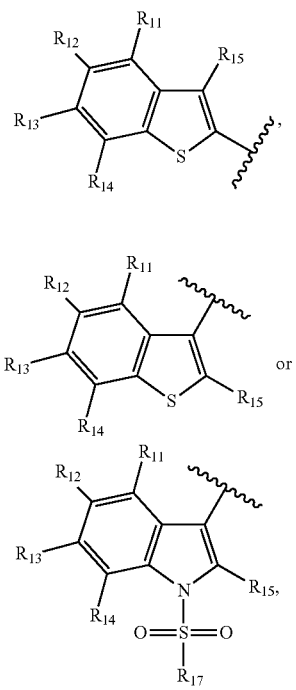

or a pharmaceutically acceptable salt, diastereomer, or enantiomer thereof.

In some embodiments, the compound wherein
wherein $R_{11}$, $R_{12}$, $R_{13}$, $R_{14}$ and $R_{15}$ are each independently H, alkyl, aryl, heteroalkyl, heteroaryl, ester, or halide, each with or without substitution; and
$R_{17}$ is alkyl, aryl, heteroalkyl, or heteroaryl, each with or without substitution,
or a pharmaceutically acceptable salt, diastereomer, or enantiomer thereof.

In some embodiments, the compound wherein
wherein $R_{11}$, $R_{12}$, $R_{13}$, $R_{14}$ and $R_{15}$ are each independently H, F, Cl, Br, $CH_3$, $CF_3$, OMe, $OCF_3$, $C(O)OR_{16}$, wherein $R_{16}$ is alkyl; and
$R_{17}$ is phenyl, benzyl, or tolyl,
or a pharmaceutically acceptable salt, diastereomer, or enantiomer thereof.

In some embodiments, the compound wherein the ring structure A is,

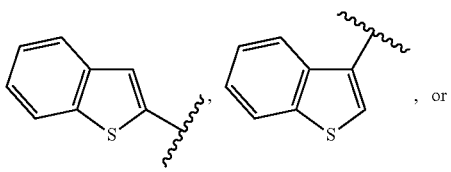

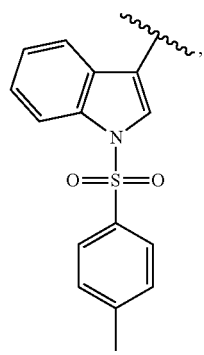

or a pharmaceutically acceptable salt, diastereomer, or enantiomer thereof.

In some embodiments, Z is

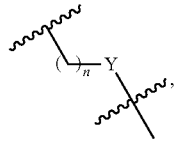

Y is —(CR$_{11}$R$_{12}$)—, n=0, 1 or 2, R$_1$ is H and R$_2$ is alkyl, ester, or CH$_2$-aryl, or a pharmaceutically acceptable salt, diastereomer, or enantiomer thereof.

In some embodiments, R$_2$ is CH$_2$CH$_3$, CH$_2$CH$_2$CH$_3$, CH$_2$C$_6$H$_5$, CH(CH$_3$)$_2$ or CO$_2$CH$_2$CH$_3$, or a pharmaceutically acceptable salt, diastereomer, or enantiomer thereof.

In some embodiments, R$_2$ is CH$_2$CH$_2$CH$_2$CH$_3$.

In some embodiments, Z is

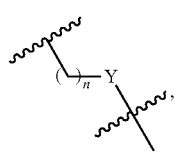

Y is —(CR$_{11}$R$_{12}$)—, n=0, 1 or 2, R$_2$ is H and R$_1$ is alkyl, ester, or CH$_2$-aryl, or a pharmaceutically acceptable salt, diastereomer, or enantiomer thereof.

In some embodiments, R$_1$ is CH$_2$CH$_3$, CH$_2$CH$_2$CH$_3$, CH$_2$C$_6$H$_5$, CH(CH$_3$)$_2$ or CO$_2$CH$_2$CH$_3$, or a pharmaceutically acceptable salt, diastereomer, or enantiomer thereof.

In some embodiments, R$_1$ is CH$_2$CH$_2$CH$_2$CH$_3$.

In some embodiments, Z is

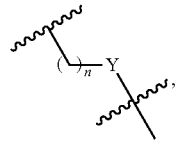

Y is —(CR$_{11}$R$_{12}$)—, n=0, 1 or 2, R$_3$ is H and R$_4$ is alkyl, ester, or CH$_2$-aryl, or a pharmaceutically acceptable salt, diastereomer, or enantiomer thereof.

In some embodiments, the compound wherein R$_4$ is CH$_2$CH$_3$, CH$_2$CH$_2$CH$_3$, CH$_2$CH$_2$CH$_2$CH$_3$, CH$_2$C$_6$H$_5$, CH(CH$_3$)$_2$ or CO$_2$CH$_2$CH$_3$, or a pharmaceutically acceptable salt, diastereomer, or enantiomer thereof.

In some embodiments, the compound wherein Z is

Y is —(CR$_{11}$R$_{12}$)—, n=0, 1 or 2, R$_4$ is H and R$_3$ is alkyl, ester, or CH$_2$-aryl, or a pharmaceutically acceptable salt, diastereomer, or enantiomer thereof.

In some embodiments, the compound wherein R$_3$ is CH$_2$CH$_3$, CH$_2$CH$_2$CH$_3$, CH$_2$CH$_2$CH$_2$CH$_3$, CH$_2$C$_6$H$_5$, CH(CH$_3$)$_2$ or CO$_2$CH$_2$CH$_3$, or a pharmaceutically acceptable salt, diastereomer, or enantiomer thereof.

In some embodiments, the compound wherein Z is

Y is —(CR$_{11}$R$_{12}$)—, n=0, 1 or 2, R$_1$ is H and R$_2$ is substituted alkyl or substituted heteroalkyl, or a pharmaceutically acceptable salt, diastereomer, or enantiomer thereof.

In some embodiments, the compound wherein R$_2$ is —CH$_2$-aryl, —CH$_2$-heteroaryl, —CH$_2$—O—CH$_2$-aryl, —CH$_2$—O—CH$_2$-heteroaryl, or a pharmaceutically acceptable salt, diastereomer, or enantiomer thereof.

In some embodiments, the compound wherein R$_2$ is

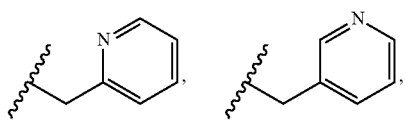

-continued

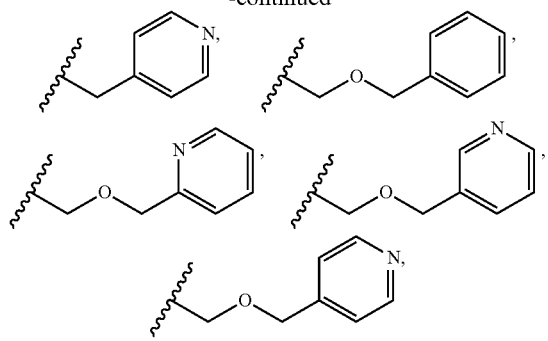

or a pharmaceutically acceptable salt, diastereomer, or enantiomer thereof.

In some embodiments, the compound wherein Z is

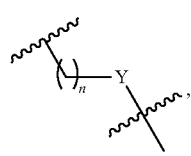

Y is —(CR$_{11}$R$_{12}$)—, n=0, 1 or 2, R$_2$ is H and R$_1$ is substituted alkyl or substituted heteroalkyl,
or a pharmaceutically acceptable salt, diastereomer, or enantiomer thereof.

In some embodiments, the compound wherein R$_1$ is —CH$_2$-aryl, —CH$_2$-heteroaryl, —CH$_2$—O—CH$_2$-aryl, —CH$_2$—O—CH$_2$-heteroaryl,
or a pharmaceutically acceptable salt, diastereomer, or enantiomer thereof.

In some embodiments, the compound wherein R$_1$ is

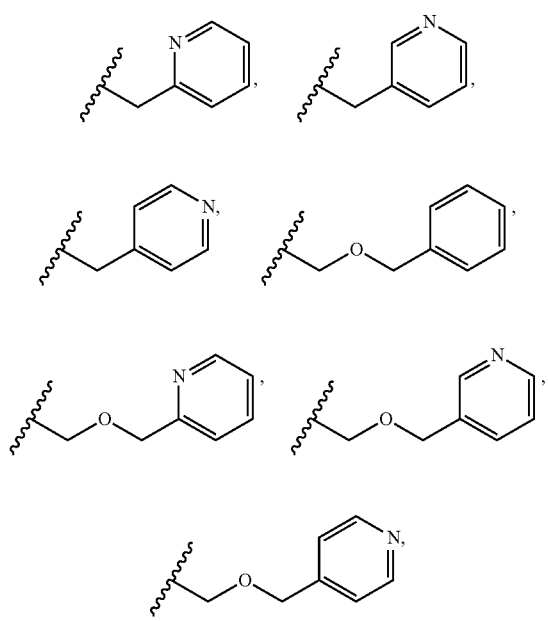

or a pharmaceutically acceptable salt, diastereomer, or enantiomer thereof.

In some embodiments, Z is

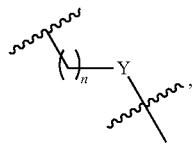

Y is —(CR$_{11}$R$_{12}$)—, α is absent, n=1 or 2, R$_6$ and R$_8$ combine to form a =O, and R$_5$ and R$_7$ are independently H, alkyl, ester, or CH$_2$-aryl,
or a pharmaceutically acceptable salt, diastereomer, or enantiomer thereof.

In some embodiments, R$_5$ and R$_7$ are independently H, CH$_2$CH$_3$, CH$_2$CH$_2$CH$_3$, CH$_2$C$_6$H$_5$, CH(CH$_3$)$_2$ or CO$_2$CH$_2$CH$_3$,
or a pharmaceutically acceptable salt, diastereomer, or enantiomer thereof.

In some embodiments, Z is

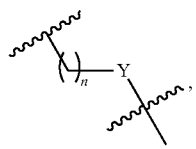

Y is —(CR$_{11}$R$_{12}$)—, α is absent, n=1 or 2, R$_5$ and R$_7$ combine to form a =O, and R$_6$ and R$_8$ are independently H, alkyl, ester, or CH$_2$-aryl,
or a pharmaceutically acceptable salt, diastereomer, or enantiomer thereof.

In some embodiments, R$_6$ and R$_8$ are independently H, CH$_2$CH$_3$, CH$_2$CH$_2$CH$_3$, CH$_2$C$_6$H$_5$, CH(CH$_3$)$_2$ or CO$_2$CH$_2$CH$_3$,
or a pharmaceutically acceptable salt, diastereomer, or enantiomer thereof.

In some embodiments, Z is

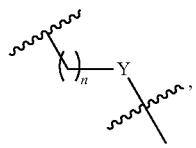

Y is —(CR$_{11}$R$_{12}$)—, α is present, n=1 or 2, R$_5$ and R$_6$ are independently H, alkyl, ester, or CH$_2$-aryl,
or a pharmaceutically acceptable salt, diastereomer, or enantiomer thereof.

In some embodiments, R$_5$ and R$_6$ are independently H, CH$_2$CH$_3$, CH$_2$CH$_2$CH$_3$, CH$_2$C$_6$H$_5$, CH(CH$_3$)$_2$ or CO$_2$CH$_2$CH$_3$,
or a pharmaceutically acceptable salt, diastereomer, or enantiomer thereof.

In some embodiments, R$_9$ and R$_{10}$ are each H,
or a pharmaceutically acceptable salt, diastereomer, or enantiomer thereof.

In some embodiments, R$_9$ and R$_{10}$ combine to form a =O,
or a pharmaceutically acceptable salt, diastereomer, or enantiomer thereof.

In some embodiments, R$_{11}$ and R$_{12}$ are each H,
or a pharmaceutically acceptable salt, diastereomer, or enantiomer thereof.

In some embodiments, $R_{11}$ and $R_{12}$ combine to form a =O,
or a pharmaceutically acceptable salt, diastereomer, or enantiomer thereof.

In some embodiments,
Z is

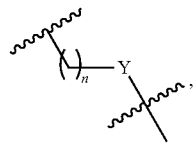

Y is —($CR_{11}R_{12}$)— where $R_{11}$ and $R_{12}$ are each H or combine to form a =O,
n is 0, 1, 2;
$R_1$ and $R_2$ are independently H, ethyl, or ester;
$R_3$, $R_4$, $R_5$, $R_6$, $R_9$, $R_{10}$ are each H;
α represents a bond, which is present or absent;
when α is present, then $R_7$ and $R_8$ are absent;
when α is absent, then $R_7$ and $R_8$ are present and are each H;
A is indole, benzimidazole or benzofuran, with or without substitution;
or a pharmaceutically acceptable salt, diastereomer, or enantiomer thereof.

In some embodiments,
wherein
Z is

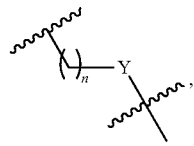

Y is —($CR_{11}R_{12}$)— where $R_{11}$ and $R_{12}$ are each H or combine to form a =O;
n is 0, 1, 2, or 3;
$R_1$ and $R_2$ are independently H, $CH_2CH_3$, $CH_2CH_2CH_2CH_3$, $CH_2CH_2CH_3$, $CH_2$-phenyl, $CH_2$-pyridyl, or —$CH_2$O-benzyl or ester;
$R_3$, $R_4$, $R_9$, $R_{10}$ are each H;
$R_5$ and $R_6$ are each independently H or $CH_2CH_3$,
α represents a bond, which is present or absent;
when α is present, then $R_7$ and $R_8$ are absent;
when α is absent, then $R_7$ and $R_8$ are present and are each H; and
A is indole, benzimidazole, benzofuran, or benzothiophene, with or without substitution;
or a pharmaceutically acceptable salt, diastereomer, or enantiomer thereof.

In some embodiments, the compound has the structure

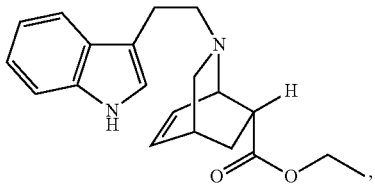

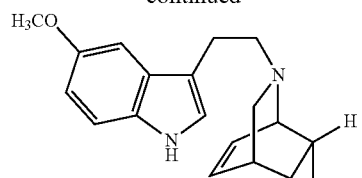

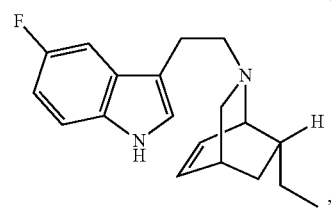

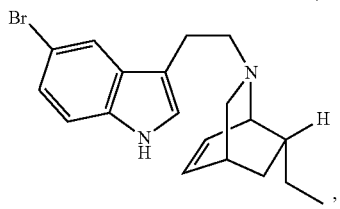

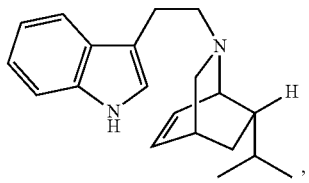

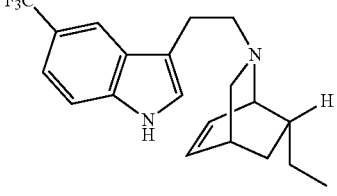

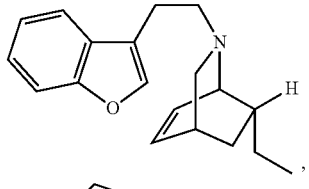

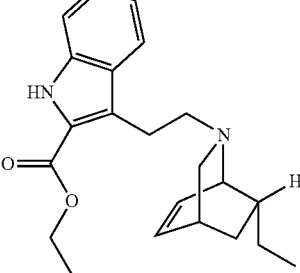

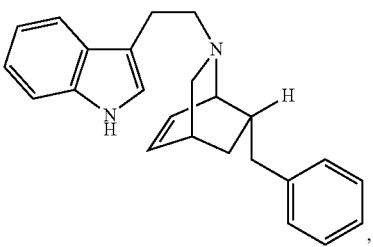

-continued
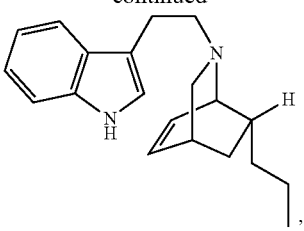
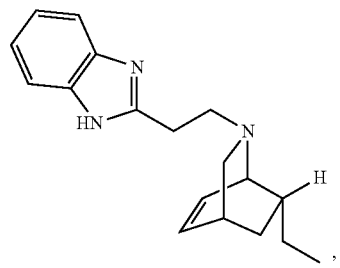
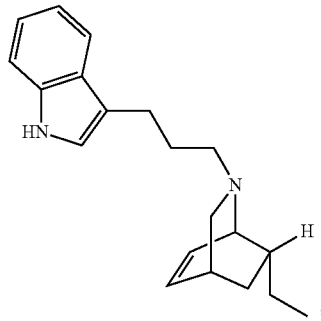
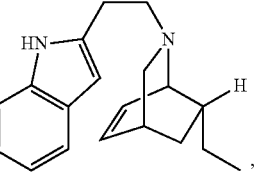
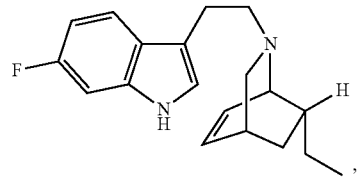
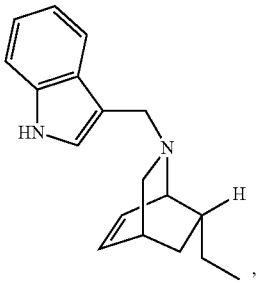
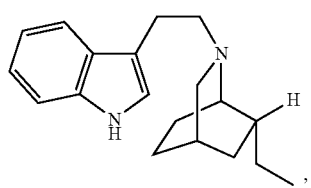
-continued
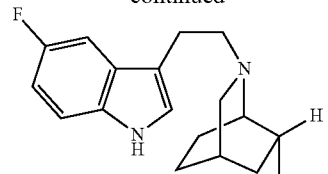
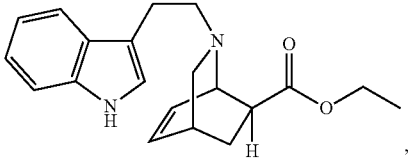
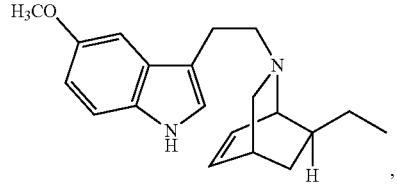
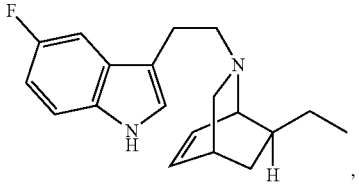
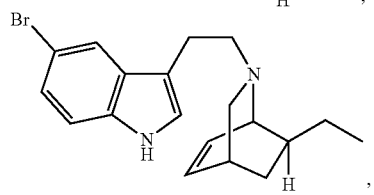
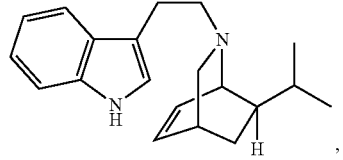
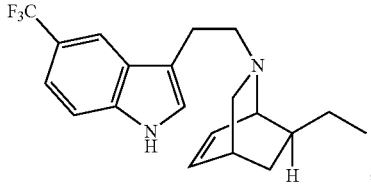
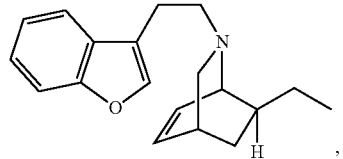
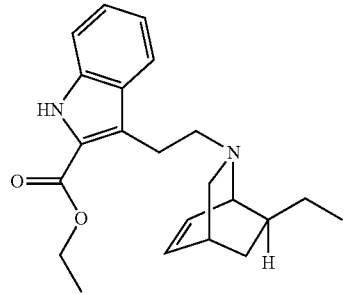

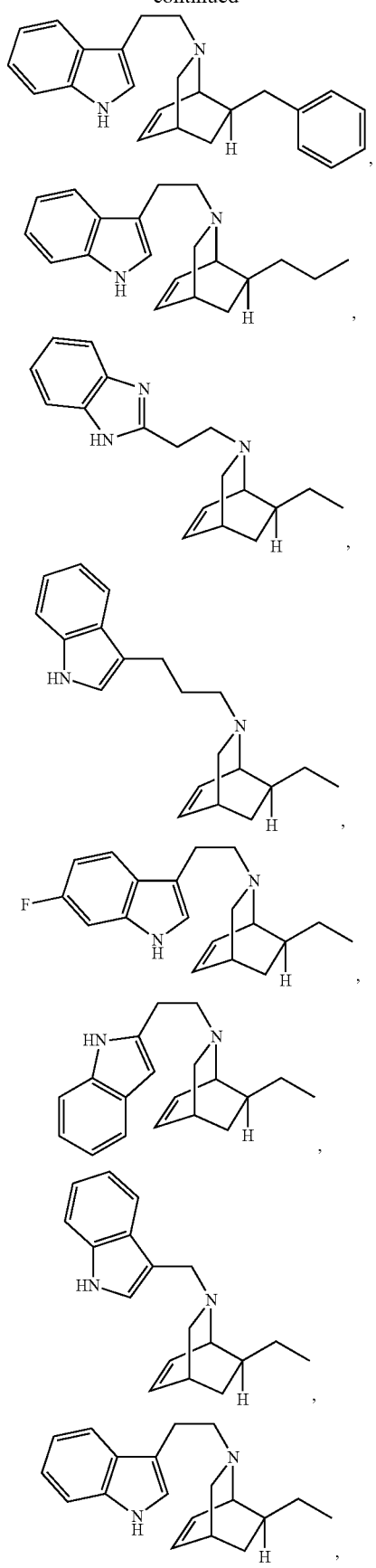
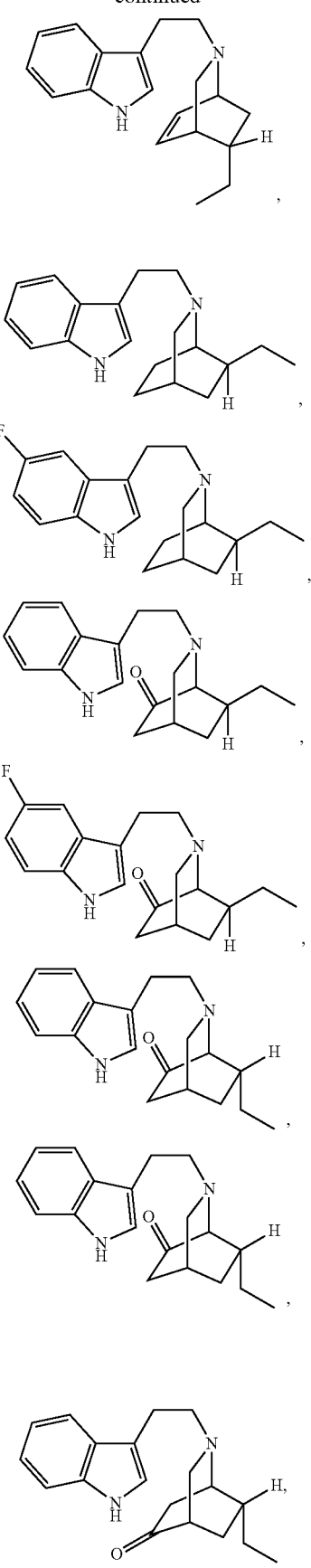

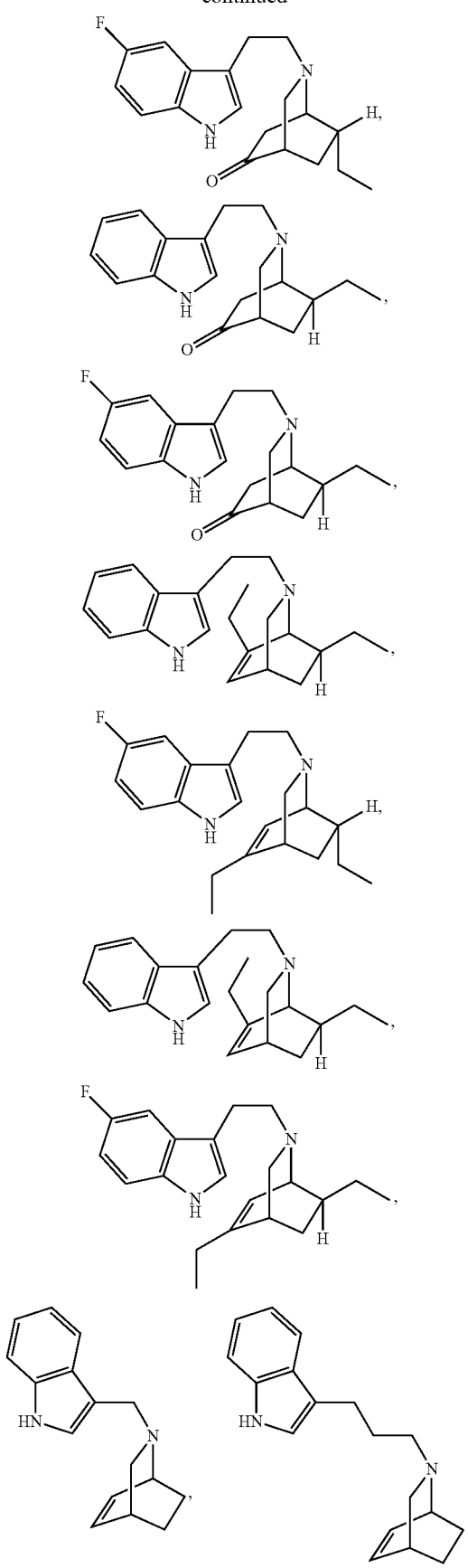
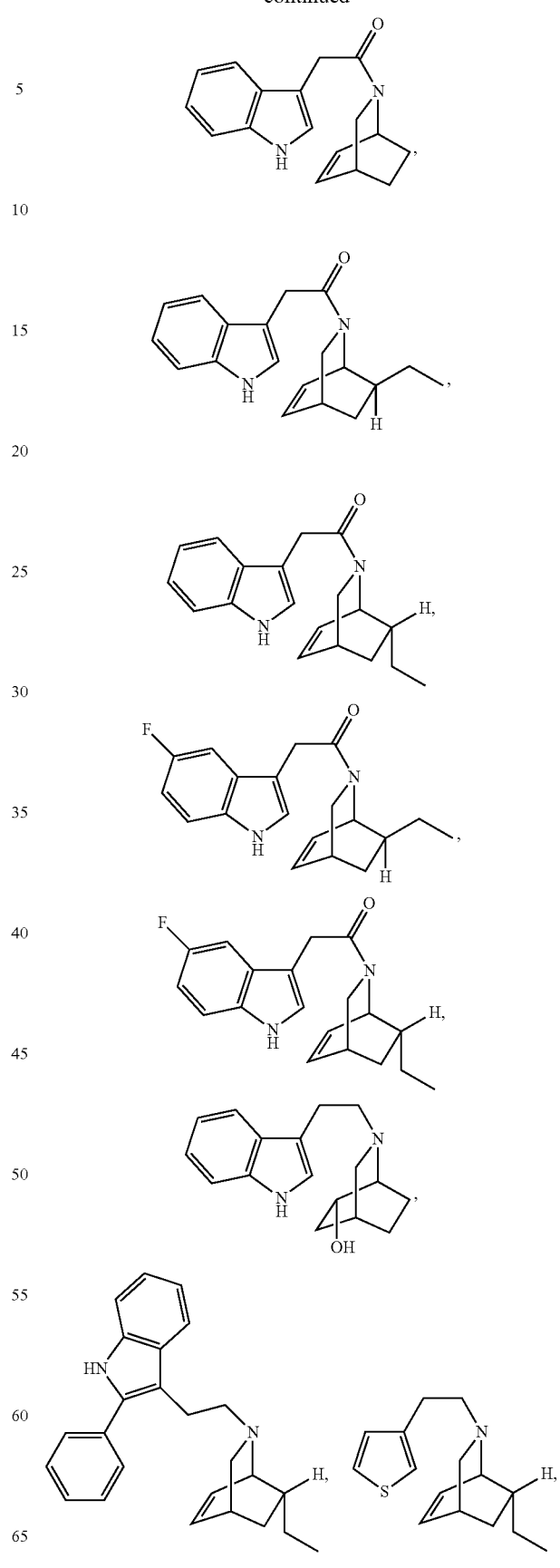

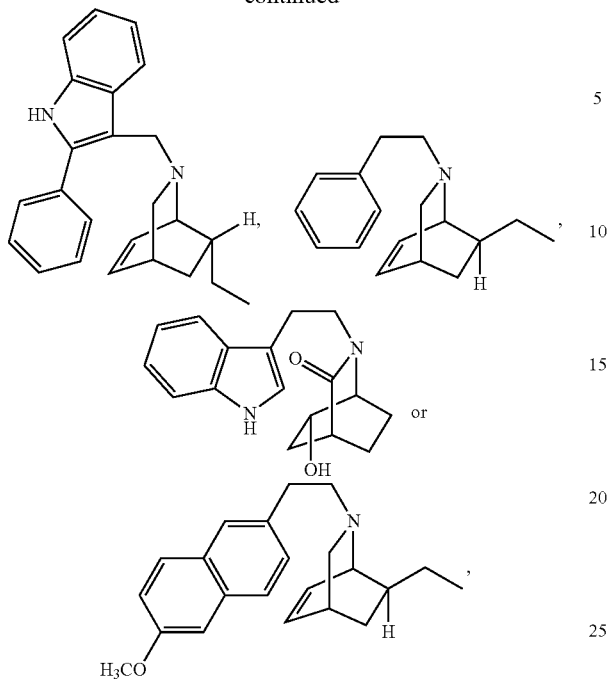
or a pharmaceutically acceptable salt, diastereomer, or enantiomer thereof.
In some embodiments, the structure of the compound is
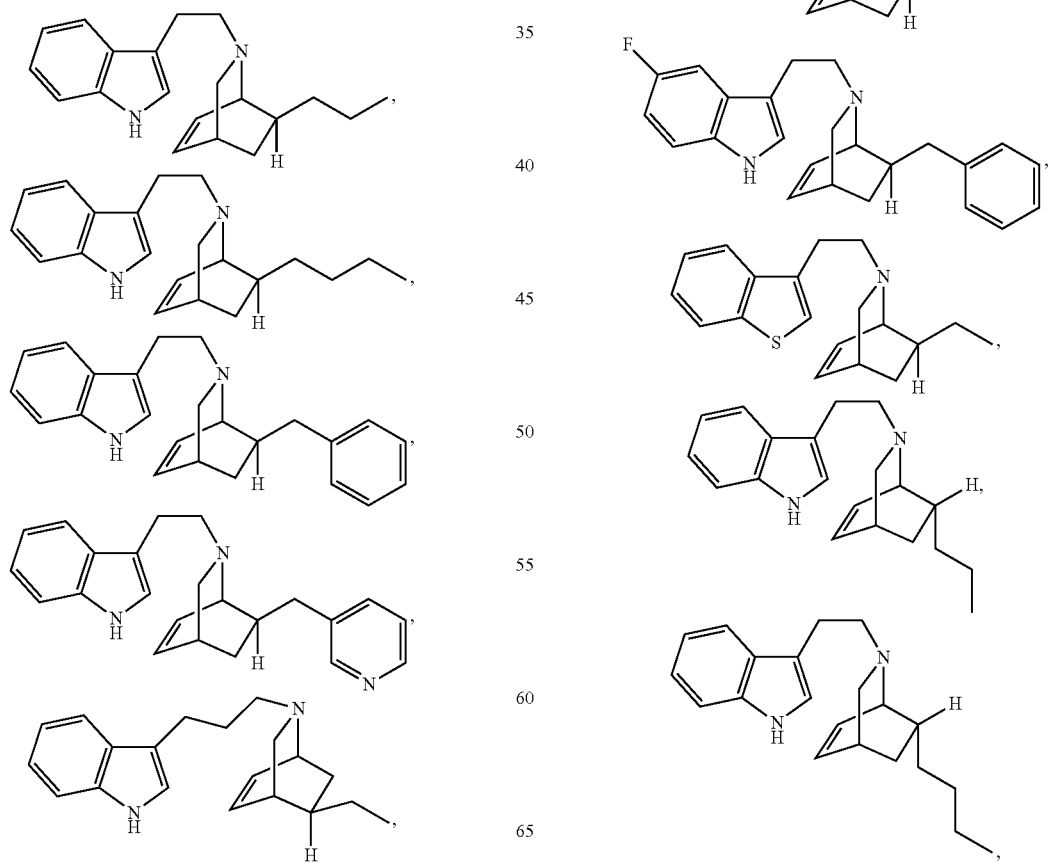

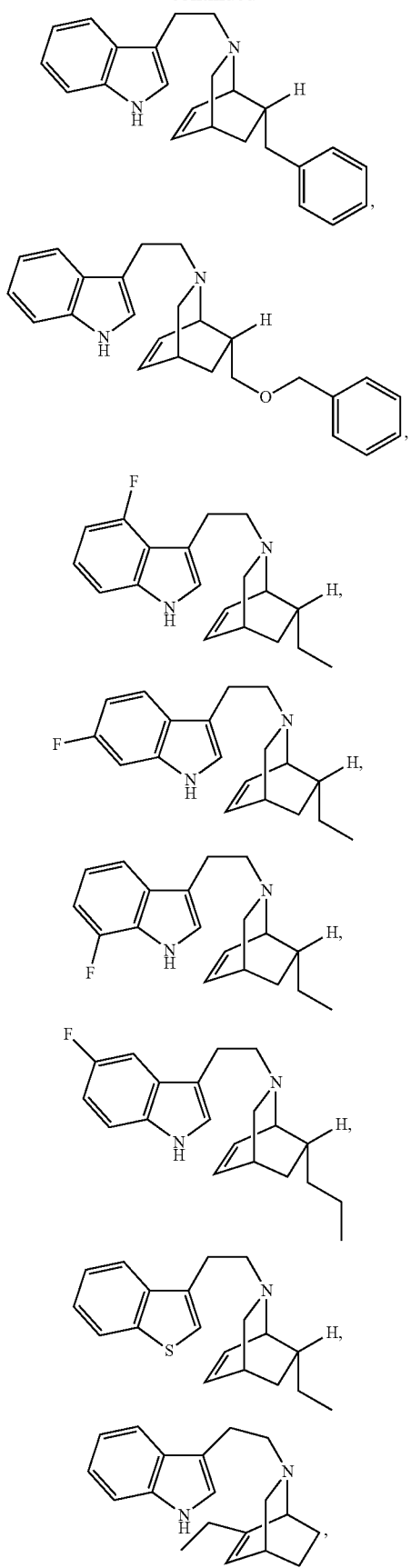

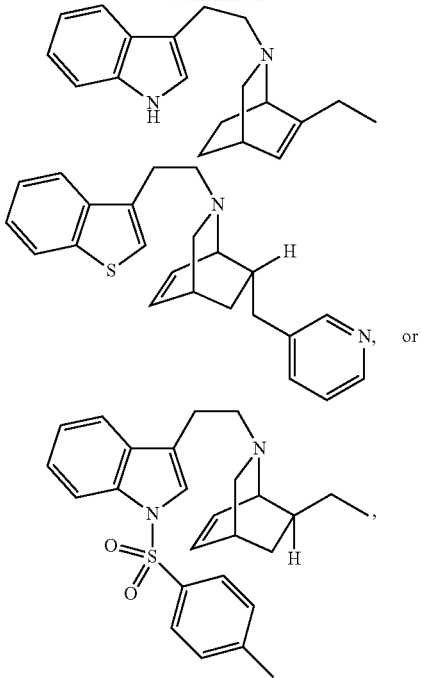

or a pharmaceutically acceptable salt, diastereomer, or enantiomer thereof.

This invention provides a method for inducing a neural cell to release Glial cell-derived neurotrophic factor (GDNF) comprising contacting the cell with a compound having the structure:

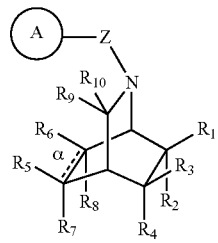

wherein
A is a ring structure, with or without substitution;
Z is present or absent and when present is,

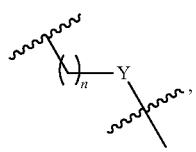

wherein
n is 0, 1, 2, 3, or 4;
Y is —(CR$_{11}$R$_{12}$)—, —NH(CR$_{11}$R$_{12}$)—, or —O(CR$_{11}$R$_{12}$)—,
wherein R$_{11}$ and R$_{12}$ are each hydrogen or combine to form a carbonyl;
R$_1$, R$_2$, R$_3$, R$_4$, R$_5$ and R$_6$ are independently H, substituted or unsubstituted alkyl, substituted or unsubstituted aryl, substituted or unsubstituted heteroalkyl, substituted or unsubstituted heteroaryl, hydroxyl, amino, ester or amide;

α represents a bond, which is present or absent;

α represents a bond, which is present or absent and when α is present, then $R_7$ and $R_8$ are absent;

$R_7$ and $R_8$ are present when α is absent and are independently H, substituted or unsubstituted alkyl, substituted or unsubstituted aryl, substituted or unsubstituted heteroalkyl, substituted or unsubstituted heteroaryl, hydroxyl, amino, ester, amide or $R_5$ and $R_7$ combine to form a carbonyl or $R_6$ and $R_8$ combine to form a carbonyl;

$R_9$ and $R_{10}$ are each hydrogen;

when (i) α is present, Z is

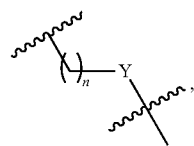

where n=1, Y is —($CR_{11}R_{12}$)— where $R_{11}$ and $R_{12}$ are H, A is unsubstituted indole attached at the 3-position of the indole, $R_3$, $R_4$, $R_5$, $R_6$, $R_9$ and $R_{10}$ are each H, and one of $R_1$ or $R_2$ is H, then (ii) the other one of $R_1$ or $R_2$ is other than ethyl ester; and when (i) α is present, Z is

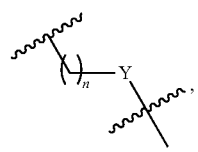

Y is —($CR_{11}R_{12}$)—, one of $R_1$ or $R_2$ is ethyl, n=1 and $R_3$, $R_4$, $R_5$, $R_6$, $R_9$, $R_{10}$, $R_{11}$ and $R_{12}$ are each H, then (ii) A is other than unsubstituted thiophene attached at the 3-position of the thiophene or phenyl;

or a pharmaceutically acceptable salt, diastereomer, or enantiomer thereof.

In some embodiments of the above method, the compound has the structure

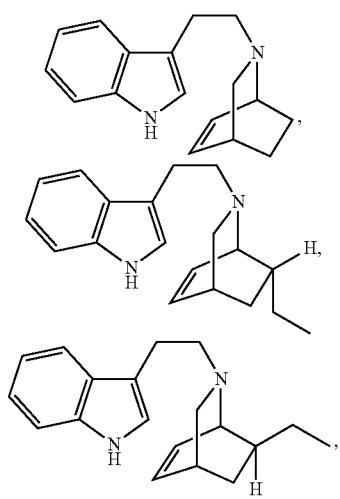

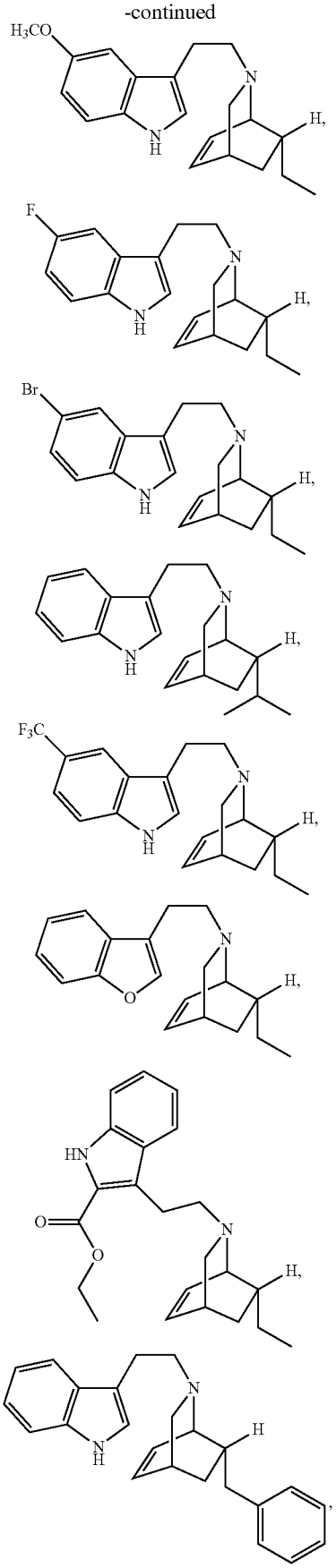

-continued
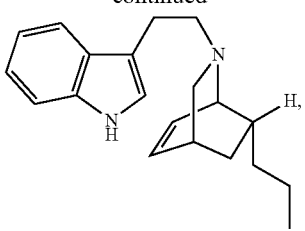
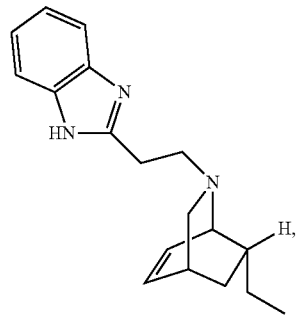
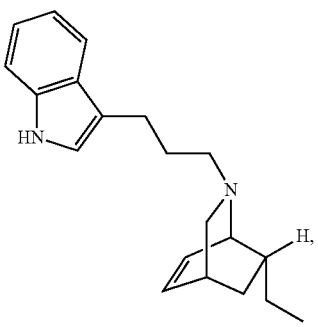
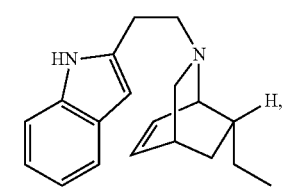
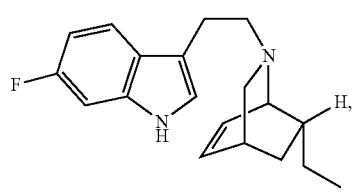
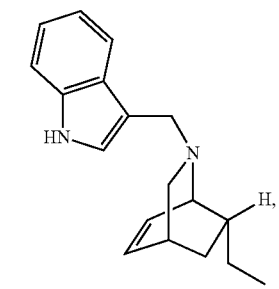
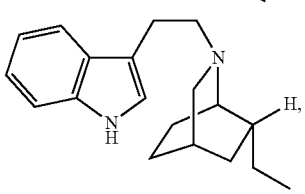
-continued
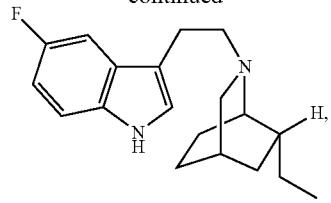
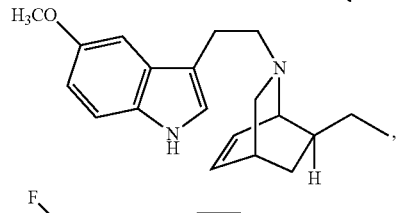
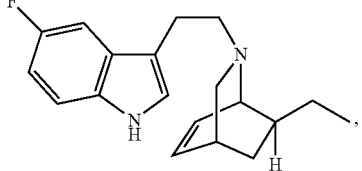
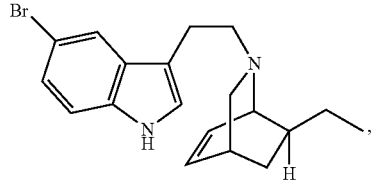
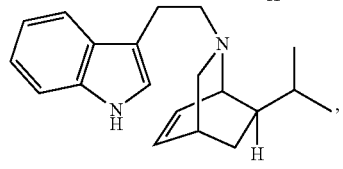
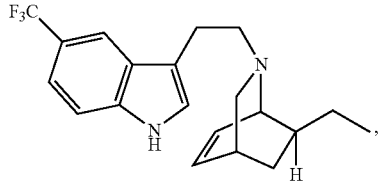
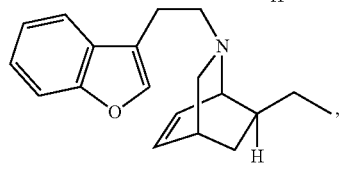
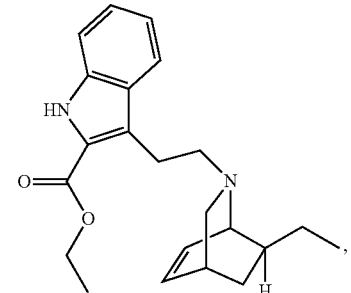
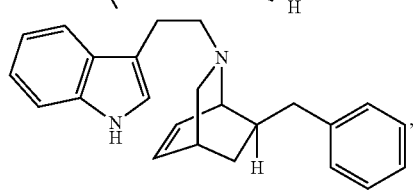

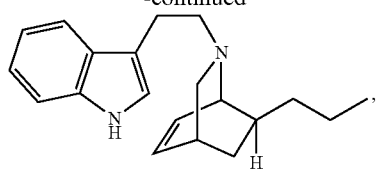
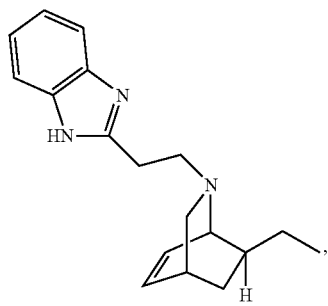
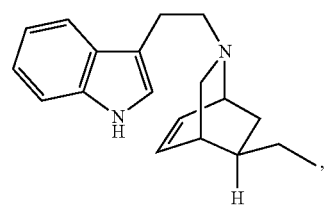
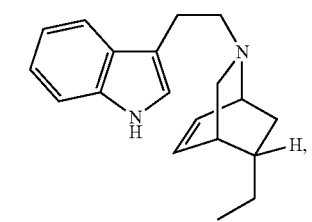
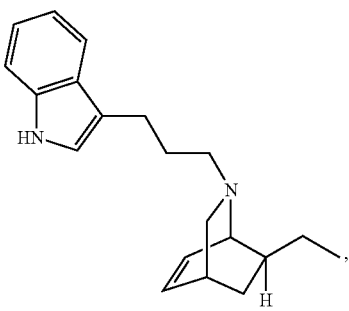
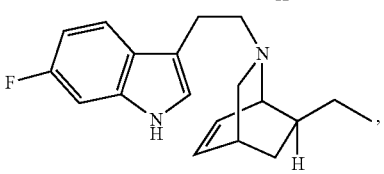
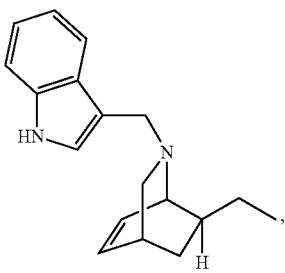
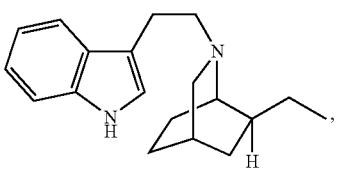
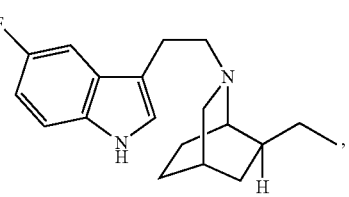
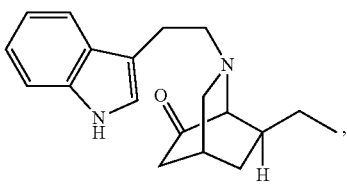
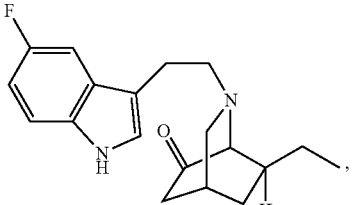
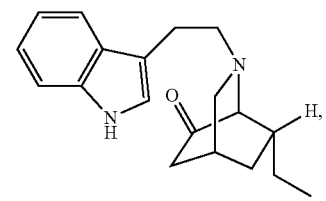
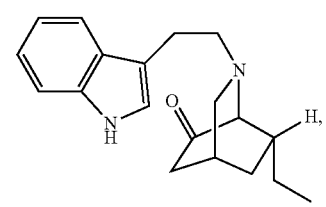
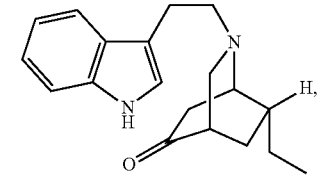

-continued
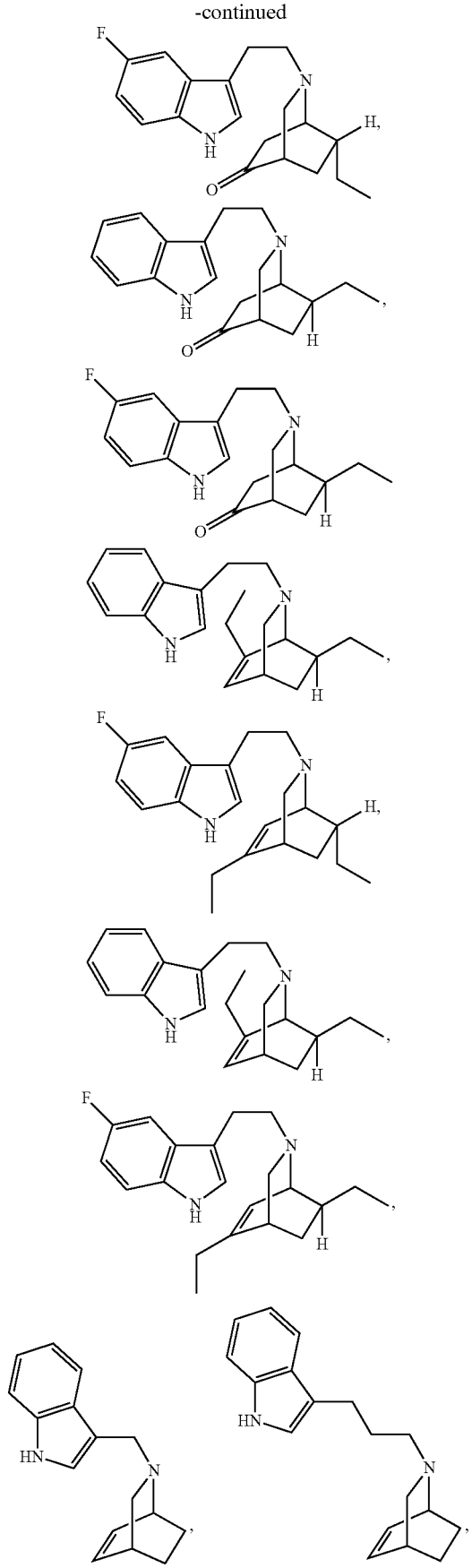
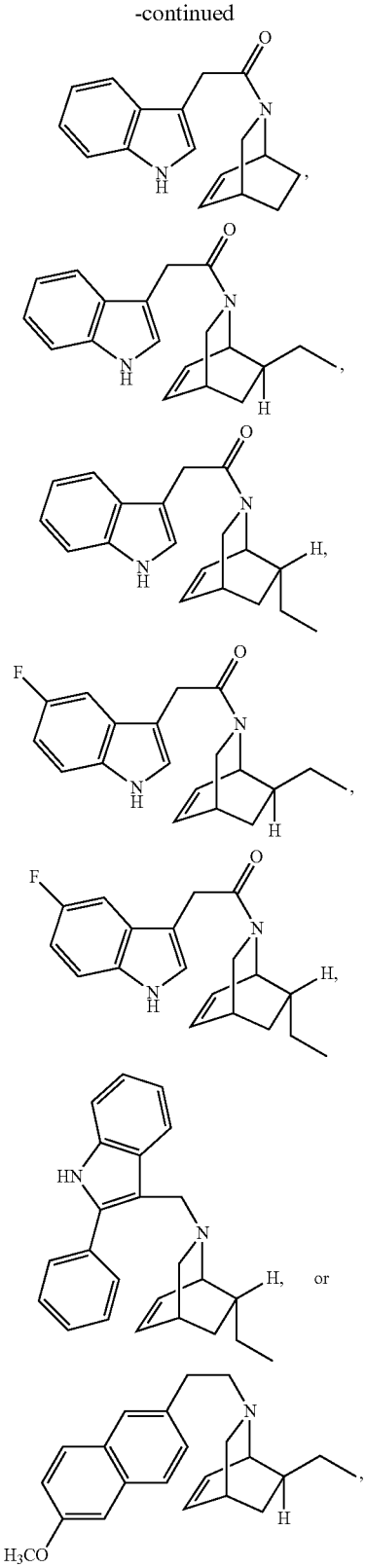
or a pharmaceutically acceptable salt, diastereomer, or enantiomer thereof.
In some embodiments of the above method, the compound has the structure -continued
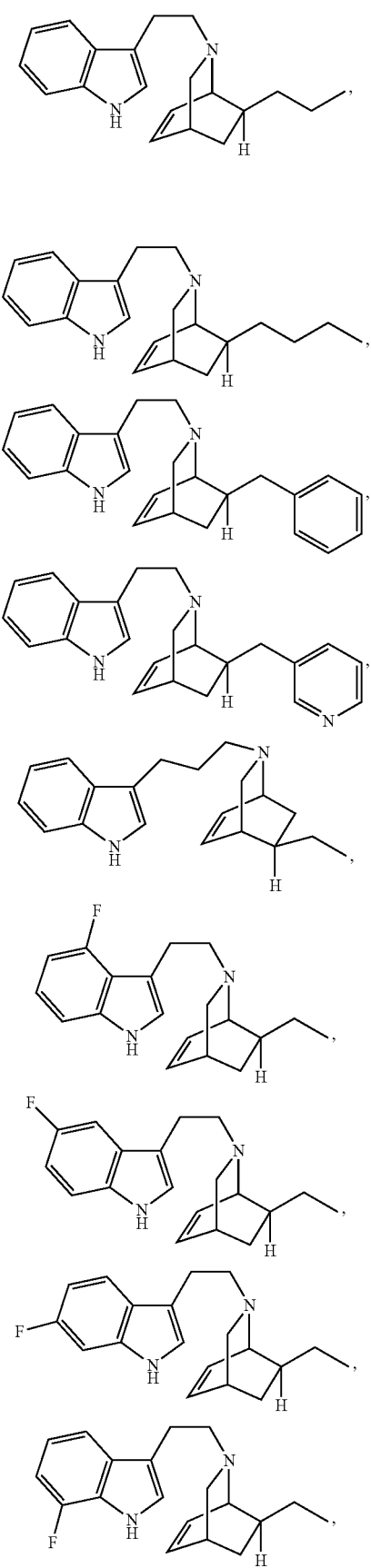
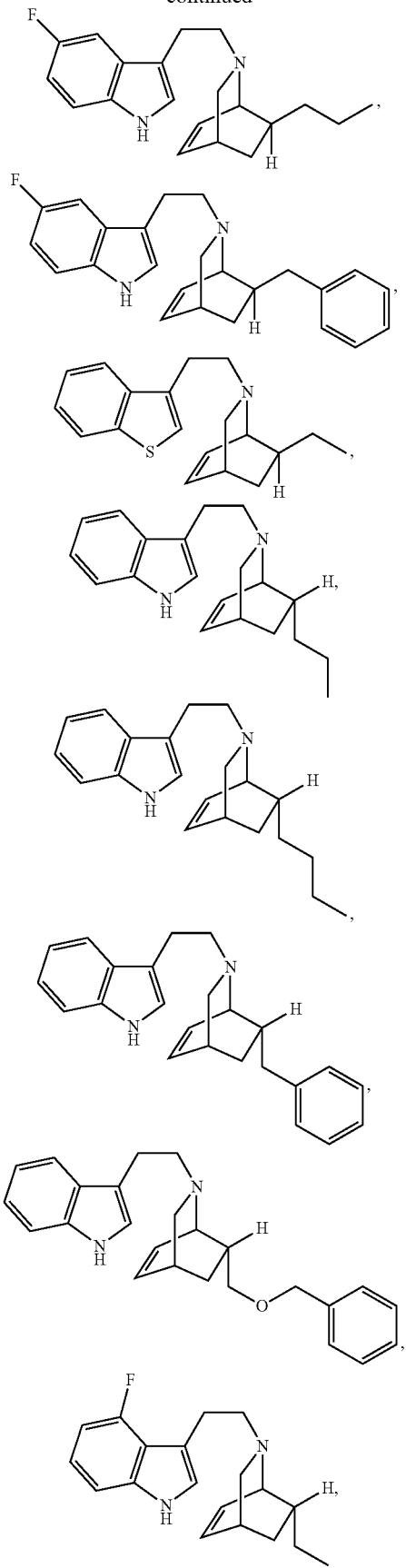

-continued

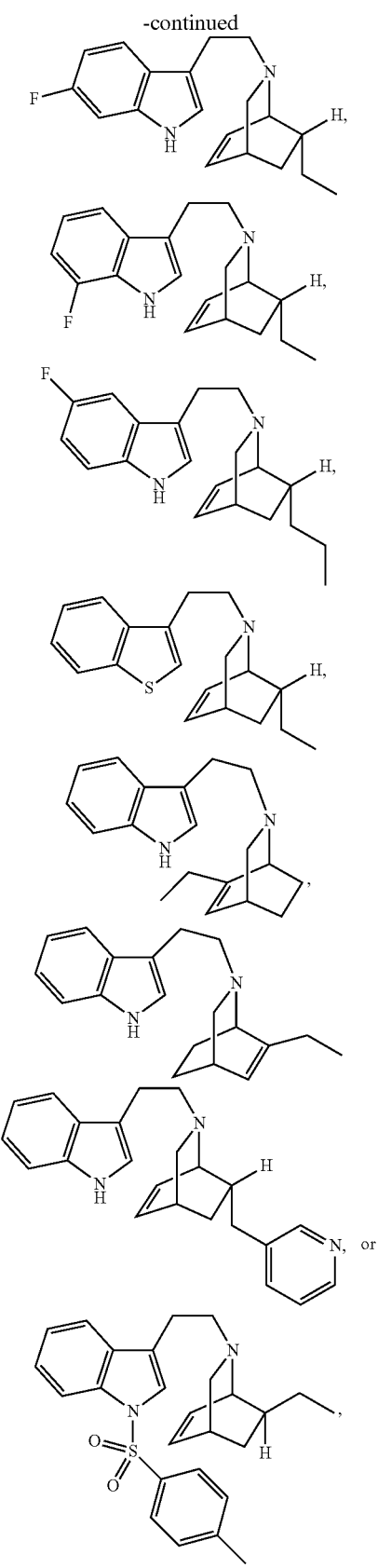

or a pharmaceutically acceptable salt, diastereomer, or enantiomer thereof.

In some embodiments, a method for inducing the release of Glial cell-derived neurotrophic factor (GDNF) in a mammal.

In some embodiments, a method for selectively inducing the release of Glial cell-derived neurotrophic factor (GDNF) in a mammal.

In some embodiments, a method for treating injury or degeneration of neurons in a mammal.

In some embodiments, a method for reducing one or more symptoms of disease in a mammal.

In some embodiments, a method of treating a human subject afflicted with alcohol addiction, drug addiction, depression, neuropathic pain, Parkinson's disease (PD), brain ischemia, stroke, head trauma injury, spinal trauma injury, neurotrauma, neurodegenerative disease, neurotoxic injury, nerve damage, dementia, Alzheimer's type dementia, senile dementia, depression, memory disorders, hyperactive syndrome, attention deficit disorder, Multiple Sclerosis (MS), schizophrenia, affective illness, Amyotrophic Lateral Sclerosis, Restless Legs Syndrome (RLS), hearing loss, Multiple System Atrophy (MSA), Glucoma, modifying Parkinson's disease, and Progressive Supranuclear Palsy (PSP), comprising administering to the human subject a compound or composition having the structure

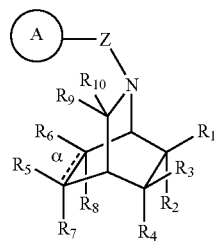

wherein
A is a ring structure, with or without substitution;
Z is present or absent and when present is

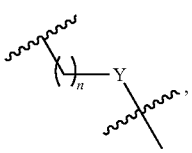

wherein
n is 0, 1, 2, 3, or 4;
Y is —(CR$_{11}$R$_{12}$)—, —NH(CR$_{11}$R$_{12}$)—, or —O(CR$_{11}$R$_{12}$)—,
wherein R$_{11}$ and R$_{12}$ are each hydrogen or combine to form a carbonyl;
R$_1$, R$_2$, R$_3$, R$_4$, R$_5$ and R$_6$ are independently H, substituted or unsubstituted alkyl, substituted or unsubstituted aryl, substituted or unsubstituted heteroalkyl, substituted or unsubstituted heteroaryl, hydroxyl, amino, ester or amide;
α represents a bond, which is present or absent;
α represents a bond, which is present or absent and when α is present, then R$_7$ and R$_8$ are absent;
R$_7$ and R$_8$ are present when α is absent and are independently H, substituted or unsubstituted alkyl, substituted or unsubstituted aryl, substituted or unsubstituted heteroalkyl, substituted or unsubstituted heteroaryl, hydroxyl, amino, ester, amide or $R_5$ and $R_7$ combine to form a carbonyl or $R_6$ and $R_8$ combine to form a carbonyl;

$R_9$ and $R_{10}$ are each hydrogen when (i) α is present, Z is

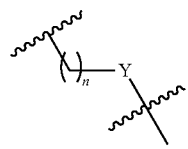

where n=1, Y is —$(CR_{11}R_{12})$— where $R_{11}$ and $R_{12}$ are H, A is unsubstituted indole attached at the 3-position of the indole, $R_3$, $R_4$, $R_5$, $R_6$, $R_9$ and $R_{10}$ are each H, and one of $R_1$ or $R_2$ is H, then (ii) the other one of $R_1$ or $R_2$ is other than ethyl ester; and when (i) α is present, Z is

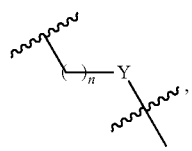

Y is —$(CR_{11}R_{12})$—, one of $R_1$ or $R_2$ is ethyl, n=1 and $R_3$, $R_4$, $R_5$, $R_6$, $R_9$, $R_{10}$, $R_{11}$ and $R_{12}$ are each H, then (ii) A is other than unsubstituted thiophene attached at the 3-position of the thiophene or phenyl;

or a pharmaceutically acceptable salt, diastereomer, or enantiomer thereof.

A process for producing the compound the present invention comprising:

(i) (a) contacting a compound having the structure:

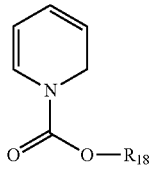

wherein $R_{18}$ is alkyl or benzyl, with methyl vinyl ketone so as to produce a mixture of exo and endo compounds having the structures:

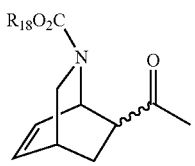

(b) reacting the product of step (a) with tosylhydrazine in a first suitable solvent so as to produce a mixture of exo and endo compounds having the structures:

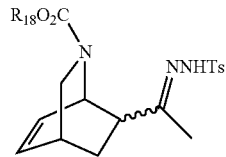

(c) separating the endo and exo products of step (b), and reacting each product with a reducing agent in a second suitable solvent to produce compounds having the structures:

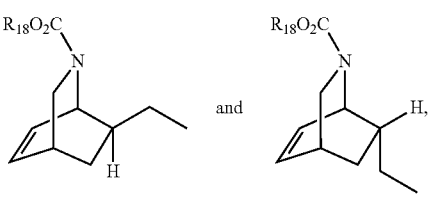

or (ii) (a) contacting a compound having the structure:

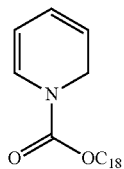

with ethyl acrylate so as to produce a mixture of exo and endo compounds having the structures:

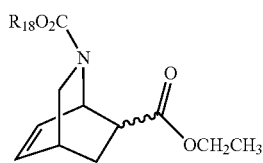

(b) reacting the product of step (a) with lithium hydroxide to produce the corresponding acid followed by reacting the acid with N,O-dimethylhydroxylamine in the presence of 1-ethyl-3-(3-dimethylaminopropyl)carbodiimide in a first suitable solvent so as to produce a mixture of exo and endo compounds having the structures:

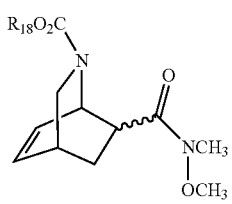

(c) reacting the product of step (b) with $R_{19}$MgBr in a ethereal solvent so as to produce a mixture of exo and endo compounds having the structures:

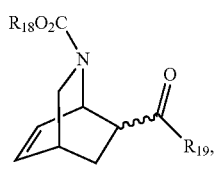

wherein R$_{19}$ is alkyl, (d) reacting the product of step (a) with tosylhydrazine in a first suitable solvent so as to produce a mixture of exo and endo compounds having the structures:

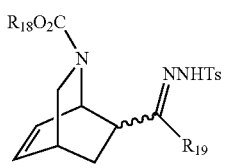

(e) separating the endo and exo products of step (b), and reacting each product with a reducing agent in a second suitable solvent to produce compounds having the structures:

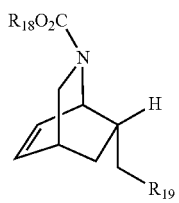 and 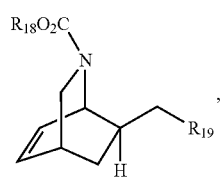, (iii) (a) contacting a compound having the structure:

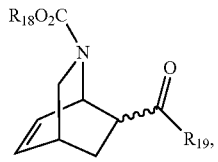

wherein R$_{19}$ is aryl or heteroaryl, with a reducing agent to produce a mixture of exo and endo compounds having the structures:

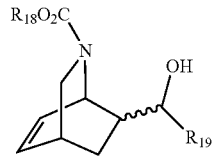

(b) reacting the product of step (a) with iodine, triphenylphosphine, and imidazole in a first suitable solvent so as to produce a mixture of exo and endo compounds having the structures:

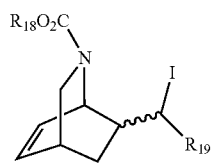

(c) reacting the product of step (b) with a reducing agent in a second suitable solvent so as to produce a mixture of exo and endo compounds

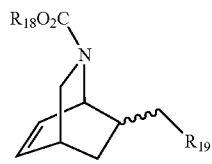

(d) separating the endo and exo products of step (c) to produce compounds having the structures:

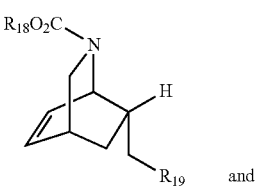 and 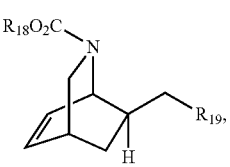, or (iv) (a) contacting a compound having the structure:

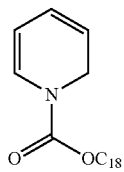

with acrolein in the presence of trifluoroacetic acid and

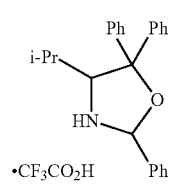

so as to produce a compound having the structure

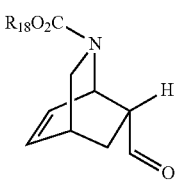

(b) reacting the product of step (a) with sodium methoxide in methanol followed by a reducing agent in a second suitable solvent so as produce a mixture of exo and endo compounds having the structure

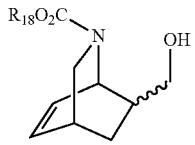

(c) separating the endo and exo products of step (b) to produce compounds having the structures:

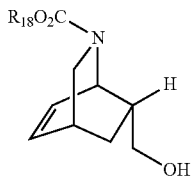 and 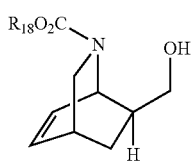

(d) reacting either product of step (c) with an alkyl halide or substituted alkyl halide to produce a compound having the structure

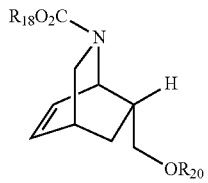 or 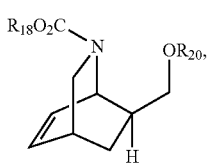

(v) (a) reacting either of the following compounds:

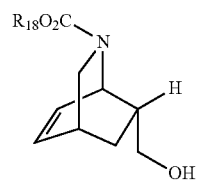 or 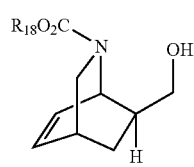

with trifluoromethanesulfonic anhydride in a basic solvent to produce either of the following compounds:

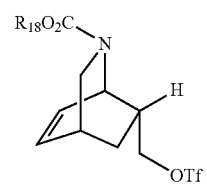 or 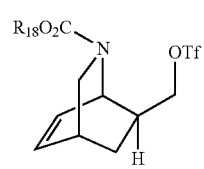

b) reacting the product of step (a) with $Li_2CuCl_4$ and $R_{21}MgBr$ in a ethereal solvent so as to either of the following compounds:

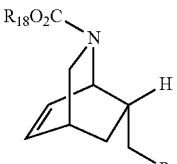 or 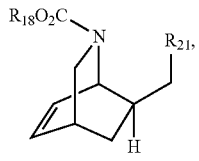, wherein $R_{21}$ is alkyl, aryl or heteroaryl, or (vi) (a) contacting a compound having the structure:

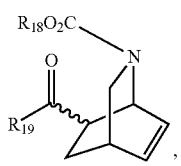, wherein $R_{19}$ is alkyl, with hydrogen in the presence of palladium on carbon in a first suitable solvent to produce a mixture of exo and endo compounds having the structure

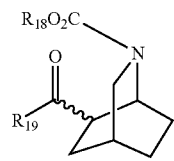

(b) reacting the product of step (a) with 3-chloroperoxybenzoic acid and $Sc(OTf)_3$ in a second suitable solvent so as to produce a mixture of exo and endo compounds having the structures:

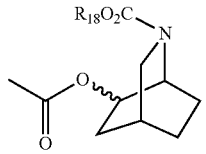

(c) reacting the product of step (b) with lithium hydroxide followed by an oxidizing agent so as to produce a compound having the structure

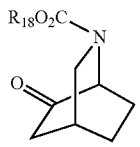

(d) reacting the product of step (c) with Lithium bis(trimethylsilyl)amide followed by Ph-N(OTf)$_2$ so as to produce a compound having the structure

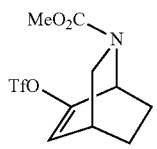

(e) reacting the product of step (d) with CuBr.SMe$_2$ and R$_{21}$MgBr in a ethereal solvent so as to produce a compound having the structure

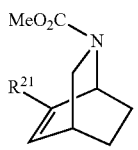

wherein R$_{21}$ is alkyl, aryl or heteroaryl; or (vii) (a) contacting a compound having the structure:

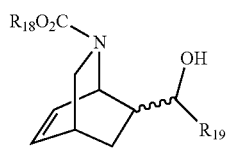

with p-toluoyl chloride in the presence of tetramethylethylenediamine in a first suitable solvent so as to produce a mixture of exo and endo compounds having the structure:

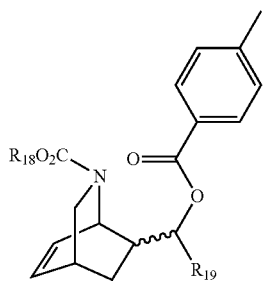

(b) reacting the product of step (a) with a samarium iodide in the presence of hexamethylphosphoramide in a second suitable solvent so as to produce a mixture of exo and endo compounds having the structure:

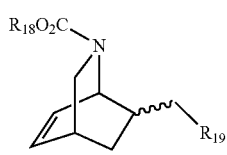

(c) separating the endo and exo products of step (b) by chromatography to produce compounds having the structures:

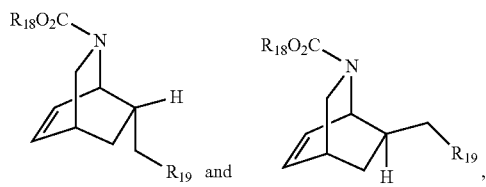

and (viii) deprotecting the carbonate of the product of any of steps (i)-(vii) with TMSI or HBr/AcOH followed by reacting the deprotected amine with:
a compound having the structure

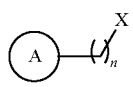

wherein X is a halide or leaving group,
in the presence of a base, or

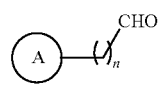

in the presence of a reducing agent and an acid,
wherein A is a ring structure, with or without substitution; and n is 0, 1, 2, 3, or 4;
so as to thereby produce the compound of the present invention.

A method of producing the compound of the present invention, further comprising reacting the product of (viii) with hydrogen in the presence of palladium on carbon in a first suitable solvent to produce a compound of the present invention wherein bond α is absent.

The present invention provides a compound having the structure:

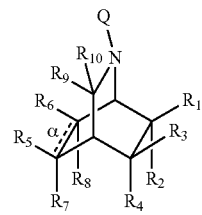

wherein
Q is H or —OC(O)OR$_{22}$
 wherein R$_{22}$ is alkyl, —CH$_2$-aryl or aryl
R$_1$, R$_2$, R$_3$, R$_4$, R$_5$ and R$_6$ are independently H, substituted or unsubstituted alkyl, substituted or unsubstituted aryl, substituted or unsubstituted heteroalkyl, substituted or unsubstituted heteroaryl, hydroxyl, amino, ester or amide;
α represents a bond, which is present or absent and when α is present, then R$_7$ and R$_8$ are absent;
R$_7$ and R$_8$ are present when α is absent and are independently H, substituted or unsubstituted alkyl, substituted or unsubstituted aryl, substituted or unsubstituted heteroalkyl, substituted or unsubstituted heteroaryl, hydroxyl, amino, ester, amide or $R_5$ and $R_7$ combine to form a carbonyl or $R_6$ and $R_8$ combine to form a carbonyl; and $R_9$ and $R_{10}$ are each hydrogen or combine to form a carbonyl;

or a salt, diastereomer, or enantiomer thereof.

In some embodiments, a method for use in treating injury or degeneration of neurons in a mammal.

In some embodiments, a method for use in reducing one or more symptoms of disease in a mammal.

In some embodiments, a method for use in inducing a neural cell to release Glial cell-derived neurotrophic factor (GDNF) comprising contacting the cell with a compound having the structure:

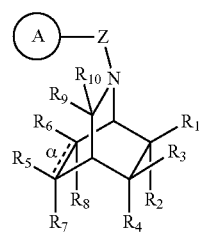

wherein
A is a ring structure, with or without substitution;
Z is present or absent and when present is

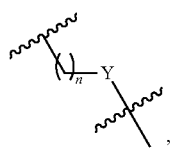

wherein
n is 0, 1, 2, 3, or 4;
Y is —(CR$_{11}$R$_{12}$)—, —NH(CR$_{11}$R$_{12}$)—, or —O(CR$_{11}$R$_{12}$)—,
wherein $R_{11}$ and $R_{12}$ are each hydrogen or combine to form a carbonyl;
$R_1$, $R_2$, $R_3$, $R_4$, $R_5$ and $R_6$ are independently H, substituted or unsubstituted alkyl, substituted or unsubstituted aryl, substituted or unsubstituted heteroalkyl, substituted or unsubstituted heteroaryl, hydroxyl, amino, ester or amide;
α represents a bond, which is present or absent;
α represents a bond, which is present or absent and when α is present, then $R_7$ and $R_8$ are absent;
$R_7$ and $R_8$ are present when α is absent and are independently H, substituted or unsubstituted alkyl, substituted or unsubstituted aryl, substituted or unsubstituted heteroalkyl, substituted or unsubstituted heteroaryl, hydroxyl, amino, ester, amide or $R_5$ and $R_7$ combine to form a carbonyl or $R_6$ and $R_8$ combine to form a carbonyl;
$R_9$ and $R_{10}$ are each hydrogen;

when (i) α is present, Z is

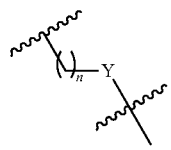

where n=1, Y is —(CR$_{11}$R$_{12}$)— where $R_{11}$ and $R_{12}$ are H, A is unsubstituted indole attached at the 3-position of the indole, $R_3$, $R_4$, $R_5$, $R_6$, $R_9$ and $R_{10}$ are each H, and one of $R_1$ or $R_2$ is H, then (ii) the other one of $R_1$ or $R_2$ is other than ethyl ester; and
when (i) α is present, Z is

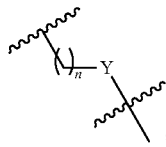

Y is —(CR$_{11}$R$_{12}$)—, one of $R_1$ or $R_2$ is ethyl, n=1 and $R_3$, $R_4$, $R_5$, $R_6$, $R_9$, $R_{10}$, $R_{11}$ and $R_{12}$ are each H, then (ii) A is other than unsubstituted thiophene attached at the 3-position of the thiophene or phenyl;

or a pharmaceutically acceptable salt, diastereomer, or enantiomer thereof.

The term "GDNF inducer" is intended to mean any compound or substance that promotes the release or expression of Glial cell line-Derived Neurotrophic Factor.

The term "neural cell" is intended to mean a cell of the nervous system, both central nervous system and peripheral nervous system, and includes a neuron, neuroglia cell, glial cell or glia cell.

Except where otherwise specified, the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1$H, $^2$H, or $^3$H. Furthermore, any compounds containing $^2$H or $^3$H may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" includes cyclic, branched and straight-chain saturated aliphatic hydrocarbons, and unless otherwise specified contains one to ten carbons. Examples include, but are not limited to, methyl, ethyl, n-propyl, isopropyl, n-butyl, t-butyl, pentyl, hexyl, and octyl. Alkyl groups can be unsubstituted or substituted with one or more substituents, including but not limited to halogen, alkoxy, alkylthio, trifluoromethyl, difluoromethyl, methoxy, and hydroxyl.

As used herein, "heteroalkyl" includes both branched and straight-chain saturated aliphatic hydrocarbon groups having the specified number of carbon atoms and at least 1 heteroatom within the chain or branch.

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "heteroaryl" or "heterocycle", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include but are not limited to phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "ester" is intended to a mean an organic compound containing the R—O—CO—R' group.

The term "amide" is intended to a mean an organic compound containing the R—CO—NH—R' or R—CO—N—R'R" group.

The term "phenyl" is intended to mean an aromatic six membered ring containing six carbons.

The term "biphenyl" is intended to mean an aryl comprising two benzene rings linked together, and any substituted derivative thereof.

The term "pyrrole" is intended to mean a heteroaryl having a five-membered ring containing four carbon atoms and one nitrogen atom.

The term "furan" is intended to mean a heteroaryl having a five-membered ring containing four carbon atoms and one oxygen atom.

The term "thiophene" is intended to mean a heteroaryl having a five-membered ring containing four carbon atoms and one sulfur atom.

The term "tolyl" refers to one of the three $CH_3C_6H_4$— isomeric groups derived from toluene.

The term "pyridyl" refers to one of the three $NC_5H_4$— isomeric groups derived from pyridine.

The term "indole" is intended to mean a fully aromatic heteroaryl having a five-membered ring fused to a phenyl ring with the five-membered ring containing one nitrogen atom which is directly attached to the phenyl ring.

The term "benzimidazole" is intended to mean a fully aromatic heteroaryl having a five-membered ring fused to a phenyl ring with the five-membered ring containing two nitrogen atoms directly attached to the phenyl ring.

The term "benzofuran" is intended to mean a fully aromatic heteroaryl having a five-membered ring fused to a phenyl ring with the five-membered ring containing one oxygen atom directly attached to the phenyl ring.

The term "benzothiophene" is intended to mean a fully aromatic heteroaryl having a five-membered ring fused to a phenyl ring with the five-membered ring containing one sulfur atom directly attached to the phenyl ring.

The term "azaindole" is intended to mean a fully aromatic heteroaryl having a five-membered ring fused to a pyridine ring with the five-membered ring containing one nitrogen atom which is directly attached to the phenyl ring.

The term "benzothiazole" is intended to mean a fully aromatic heteroaryl having a five-membered ring fused to a phenyl ring with the five-membered ring containing one nitrogen atom directly attached to the phenyl ring and one sulfur atom directly attached to the phenyl ring.

The term "benzoxazole" is intended to mean a fully aromatic heteroaryl having a five-membered ring fused to a phenyl ring with the five-membered ring containing one nitrogen atom directly attached to the phenyl ring and one oxygen atom directly attached to the phenyl ring.

The term "isoquinuclidine" is intended to mean a bicyclo [2.2.2]octane having one nitrogen adjacent to the bridgehead position. The bicycle may contain 1 or 2 double bonds in the ring system.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally.

By independently substituted, it is meant that the (two or more) substituents can be the same or different.

The compounds used in the method of the present invention may be prepared by techniques well know in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) $5^{th}$ Edition (1996), March's Advanced Organic Chemistry: Reactions, Mechanisms, and Structure, Michael B. Smith, Jerry March, (Wiley-Interscience) $5^{th}$ Edition (2007), and references therein, which are incorporated by reference herein. However, these may not be the only means by which to synthesize or obtain the desired compounds.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

Another aspect of the invention comprises a compound used in the method of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein, "treating" means preventing, slowing, halting, or reversing the progression of a disease or infection. Treating may also mean improving one or more symptoms of a disease or infection.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antibacterial agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

Reagents and solvents were obtained from Sigma-Aldrich (St. Louis, Mo.), Alfa Aesar (Ward Hill, Mass.), or Fisher Scientific (Hampton, N.H.) and used without further purification unless otherwise stated. All compounds were prepared in racemic form. Nuclear magnetic resonance spectra were recorded on Bruker 300, 400, or 500 MHz instruments as indicated. Chemical shifts are reported as δ values in ppm referenced to $CDCl_3$ ($^1$H NMR=7.26 and $^{13}$C NMR=77.0). Multiplicity is indicated as follows: s (singlet); d (doublet); t (triplet); q (quartet); dd (doublet of doublets); ddd (doublet of doublet of doublets); dt (doublet of triplets); td (triplet of doublets); m (multiplet); br (broad). Low-resolution mass spectra were recorded on a JEOL LCmate (Ionization mode: APCI+). High-resolution mass spectra (HRMS) were acquired from Columbia University Mass Spectral Core facility on a JMS HX110 spectrometer.

Nuclear magnetic resonance spectra were recorded on Bruker 300 or 400 MHz instruments as indicated. Chemical shifts are reported as δ values in ppm referenced to $CDCl_3$ ($^1$H NMR=7.26 and $^{13}$C NMR=77.0). Multiplicity is indicated as follows: s (singlet); d (doublet); t (triplet); q (quartet); dd (doublet of doublets); ddd (doublet of doublet of doublets); m (multiplet); bs (broad singlet). Mass spectra were recorded on a JEOL LCmate (Ionization mode: APCI+). High-resolution mass spectra (HRMS) were acquired from Columbia University Mass Spectral Core facility on a JMS HX110 spectrometer.

For those described compounds containing a carbamate group, complex spectra with split peaks are observed. This effect can be ascribed to the presence of rotomers about the carbamate group. Likewise, the spectra of compounds which are reported as a mixture of exo/endo epimers are further complicated. Furthermore, compounds containing fluorine are subject to F—C coupling, resulting in splitting of some carbon peaks. As a result of these effects, multiple peaks may correspond to the same proton group or carbon atom. When possible, this is indicated by an "and" joining two peaks or spectral regions. Alternatively, certain carbon peaks represent two carbons (indicated by (2C) designation). In all cases the assignments of these complex peaks were determined by COSY, HSQC, and/or DEPT-135. All carbon peaks are rounded to one decimal place unless such rounding would cause two close peaks to become identical. In these cases, two decimal places are retained. For key intermediates and final products, exo or endo stereochemistry was determined using coupling constants and COSY spectra in combination with NOESY data.

For compounds where low-resolution mass is given, the calculated mass reported is that for the actual molecular formula of the compound. However, in APCI+ ionization, [M+H]⁺ ions are formed so the found masses are expected to differ by 1 m/z. For compounds where high-resolution mass is reported, the calculated mass is shown for the [M+H]⁺ ion.

Those having ordinary skill in the art of organic synthesis will appreciate that modifications to general procedures and synthetic routes contained in this application can be used to yield additional derivatives and structurally diverse compounds. Suitable organic transformations are described in FIGS. 2-12 or in March's Advanced Organic Chemistry: Reactions, Mechanisms, and Structure (Wiley-Interscience; 6$^{th}$ edition, 2007), the content of which is hereby incorporated by reference.

EXAMPLE 1

Figure 2:
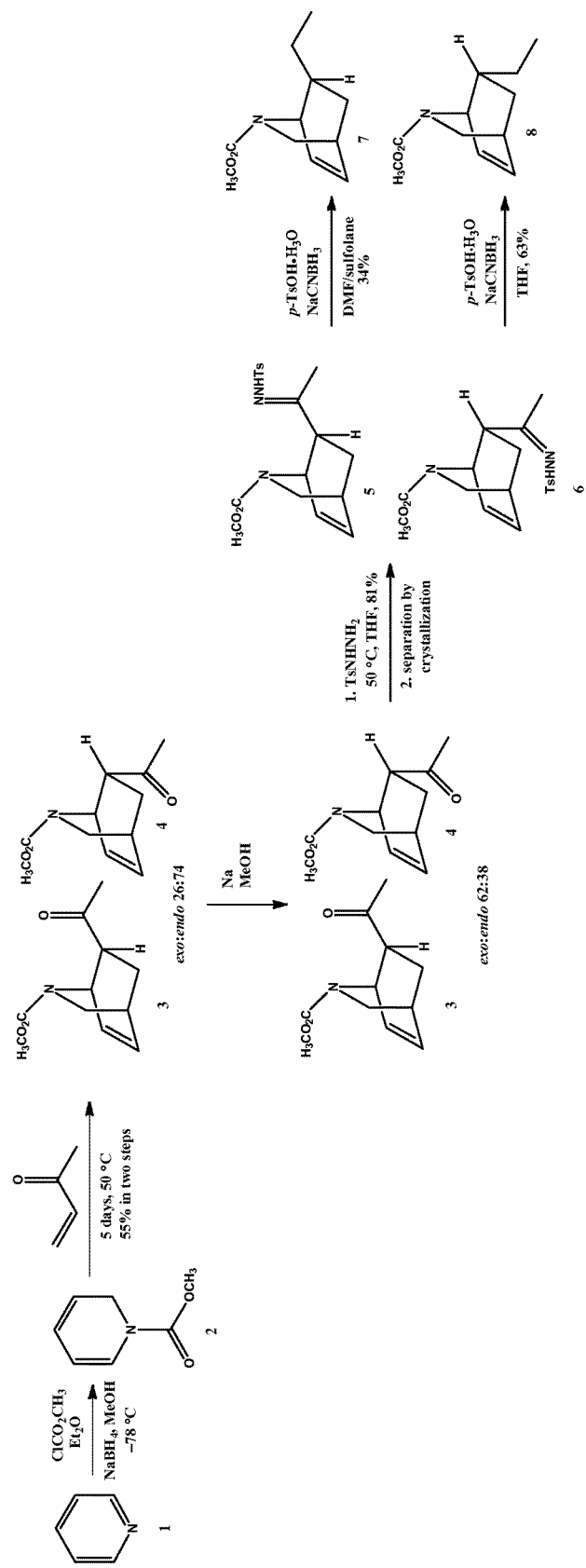
FIG. 2. Synthetic route to 7-ethyl substituted isoquinuclidine precursors.

Synthesis of Carbamate Intermediates En Route to 7-Ethyl Isoquinuclidine Derivatives The isoquinuclidine core was accessed according to the protocols shown in FIG. 2. Methyl pyridine-1(2H)-carboxylate 2 was prepared by treatment of pyridine 1 with methyl chloroformate followed by reduction with sodium borohydride. The diene was then reacted with methyl vinyl ketone at 50° C. for 5 days to form exo compound 3 and endo compound 4 in a 26:74 ratio. An epimerization occurred in the presence of Na in MeOH and a new ratio of 62:38 exo:endo was obtained (Mariano, P. S. et al. 1979; Fowler, F. K. 1972).

The mixture of exo/endo-N-(methoxycarbonyl)-7-acetyl-isoquinuclidines 3 and 4 (5.74 g, 27.4 mmol) and tosylhydrazine (5.26 g, 27.4 mmol) in 20 mL anhydrous tetrahydrofuran was stirred at 50° C. for 27 hrs to give a milky yellow solution. After cooling to r.t. and filtration, a white solid was obtained which gave 4.0 g of pure endo-epimer 6 after recrystallization from methanol. The mother liquid was concentrated and yielded 3.0 g of pure exo-epimer 5 and 1.3 g of an endo-exo mixture after two recrystallizations from methanol (Krow, G. R. et al. 1988)).

Crystalline exo-tosylhydrazone (5, 1.89 g, 5 mmol) was dissolved in 15 mL DMF and 15 mL sulfolane. Sodium cyanoborohydride (1.26 g, 20 mmol) and a catalytic amount of p-toluenesulfonic acid monohydrate (100 mg) were added and the mixture was heated at 105° C. for 41 hrs under argon. After cooling to r.t., the mixture was diluted with water (10 mL) and extracted with cyclohexane (20 mL×4). The combined organic layers were washed with water (5 mL), dried over MgSO₄, and concentrated to yield a pale yellow oil. The crude was purified by flash column chromatography (silica gel, hexane:EtOAc=5:1) to yield 7 a colorless oil.

A white suspension of crystalline endo-tosylhydrazone (6, 1.89 g, 5 mmol), sodium cyanoborohydride (1.26 g, 20 mmol), and a catalytic amount of p-toluenesulfonic acid monohydrate (80 mg) in 20 mL anhydrous tetrahydrofuran was heated at reflux for 15 hrs under argon. After cooling to r.t., the reaction mixture was poured into water (20 mL) and extracted with DCM (20 mL×3). The combined organic layers were washed with 10% sodium bicarbonate (15 mL×2) and dried over magnesium sulfate. After removing volatiles, the crude was purified by flash column chromatography (silica gel, hexane:EtOAc=4:1) to give 8 a colorless oil.

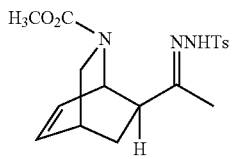

exo-N-(methoxycarbonyl)-7-(1-(2-tosylhydrazono) ethyl)-2-azabicyclo[2.2.2]-oct-5-ene (5): White solid. ¹H NMR (400 MHz, CDCl₃) δ 7.85 and 7.79 (2H, d, J=8.3 Hz), 7.45 and 7.39 (1H, s), 7.31 (2H, d, J=7.9 Hz), 6.42 (2H, m), 4.71 and 4.59 (1H, m), 3.52 and 3.48 (3H, s), 3.02 and 2.94 (1H, dd, J=9.7, 1.9 Hz), 2.87 and 2.78 (1H, ddd, J=9.8, 2.5, 2.5 Hz), 2.70 (1H, m), 2.44 (3H, s), 2.42 (1H, m), 2.30 and 2.09 (1H, ddd, 13.1, 4.4, 2.3 Hz), 1.90 and 1.80 (3H, s), 1.32 (1H, m); m/z calcd for C₁₈H₂₃N₃O₄S 377.14, found 377.8.

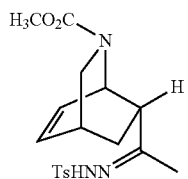

endo-N-(methoxycarbonyl)-7-(1-(2-tosylhydrazono) ethyl)-2-azabicyclo[2.2.2]-oct-5-ene (6): White solid. ¹H NMR (400 MHz, CDCl₃) δ 7.80 (2H, dd, J=7.9 Hz), 7.61 (1H, d, J=5.2 Hz), 7.30 (2H, d, J=7.9 Hz), 6.14 (1H, dd, J=14.9, 7.5 Hz), 5.99 (1H, dd, J=13.1, 6.8 Hz), 4.84 and 4.75 (1H, d, J=3.6 Hz), 3.66 and 3.65 (3H, s), 3.21 (1H, d, J=10.2 Hz), 2.92 (2H, m), 2.72 (1H, s), 2.43 and 2.42 (3H, s), 1.79 (1H, m), 1.71 and 1.69 (3H, s); m/z calcd for C₁₈H₂₃N₃O₄S 377.14, found 377.8.

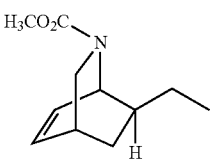

exo-N-(methoxycarbonyl)-7-ethyl-2-azabicyclo[2.2.2]-oct-5-ene (7): Colorless oil (0.33 g, 34% yield). ¹H NMR (400 MHz, CDCl₃) δ 6.47 and 6.42 (1H, br dd, J=7 Hz), 6.34 and 6.30 (1H, br dd, J=8 Hz), 4.59 and 4.44 (1H, d, J=6 Hz), 3.67 and 3.66 (3H, s), 3.20 (1H, td, J=10, 2 Hz), 2.98 and 2.94 (1H, dt, J=10, 3 Hz), 2.65 (1H, m), 1.64 and 1.61 (1H, dt, J=10, 3 Hz), 1.38 (3H, m), 1.00 (1H, m), 0.95 and 0.92 (3H, t, J=7 Hz); ¹³C NMR (100 MHz, CDCl₃) δ 156.7 and 156.3 (NCO2), 133.8 and 133.7 (CH═), 133.3 and 133.1 (CH═), 52.2 and 52.1 (OMe), 49.1 and 48.8 (C1), 48.4 and 48.1 (C3), 40.7 (C4), 30.8 and 30.6 (C7), 29.9 (C8), 27.5 and 27.4 (CH₂), 12.1 and 12.0 (CH₃) m/z calcd for C₁₁H₁₇NO₂ 195.13, found 195.9.

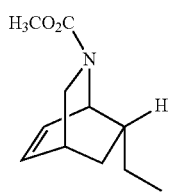

endo-N-(methoxycarbonyl)-7-ethyl-2-azabicyclo[2.2.2]-oct-5-ene (8): Colorless oil (0.97 g, 63% yield). $^1$H NMR (400 MHz, CDCl$_3$) δ 6.31 (2H, m), 4.66 and 4.48 (1H, s), 3.69 and 3.66 (3H, s), 3.21 (1H, m), 2.94 (1H, m), 2.69 (1H, m), 1.96 (1H, m), 1.81 (1H, m), 1.19 (1H, m), 1.01-0.84 (5H, m); $^{13}$C NMR (100 MHz, CDCl$_3$) δ 155.6 and 155.2 (NCO2), 134.4 and 134.0 (CH=), 130.6 and 130.0 (CH=), 52.0 and 51.9 (OMe), 49.3 and 48.9 (C1), 46.9 and 46.5 (C3), 40.7 and 40.5 (C4), 31.0 and 30.8 (C7), 30.0 (C8), 28.3 and 28.2 (CH$_2$), 11.2 (CH$_3$); m/z calcd for C$_{11}$H$_{17}$NO$_2$ 195.13, found 195.9.

EXAMPLE 2

General Procedure and Synthesis of 7-Ethyl Isoquinuclidine Derivatives

Figure 3:
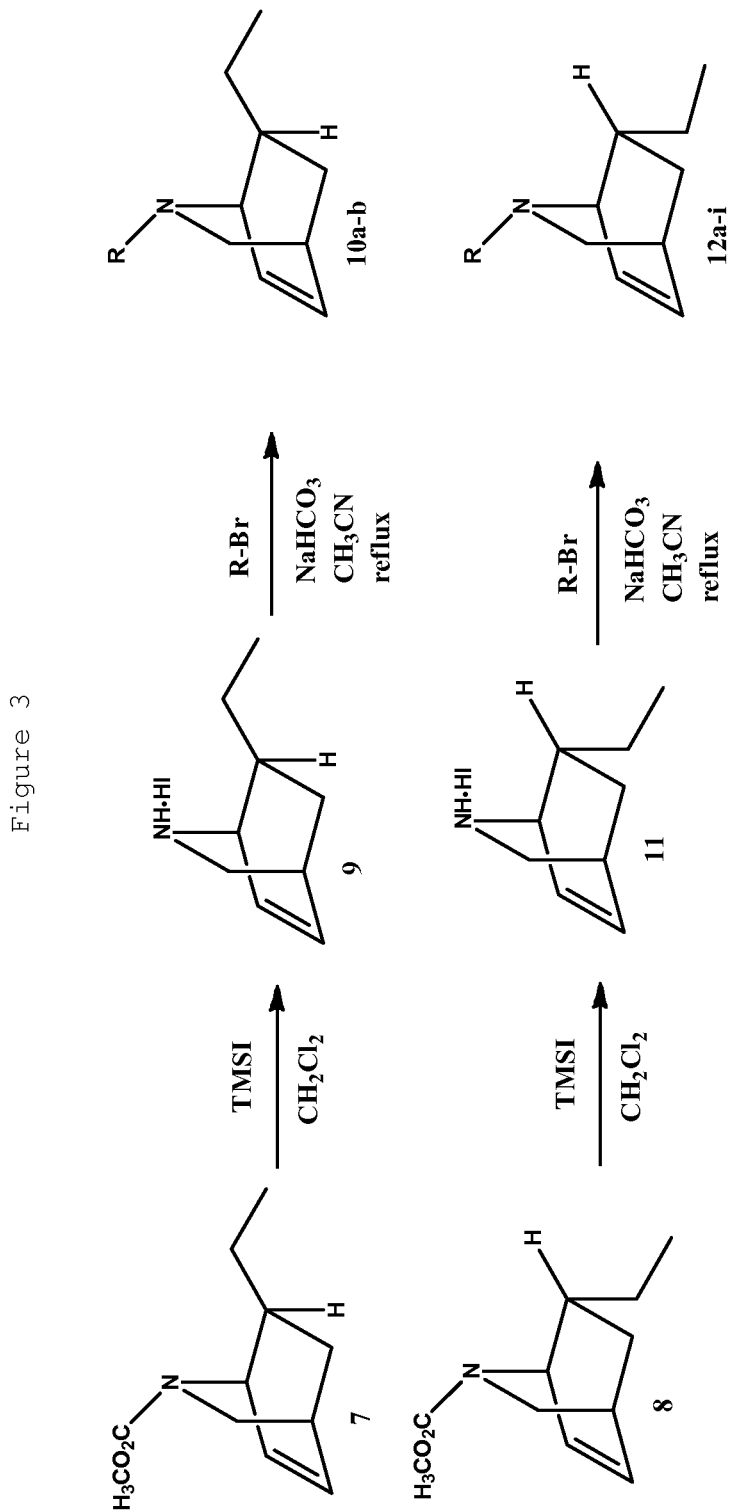
FIG. 3. General synthetic route to 7-substituted isoquinuclidine derivatives.

A variety of 7-ethyl derivatives were prepared, unless otherwise indicated, according to general procedure A (see FIG. 3).

General procedure A for preparation of N-arylalkyl-isoquinuclidines: Iodotrimethylsilane (4 equiv.) was added to a solution of the corresponding N-(methoxycarbonyl)-isoquinuclidine (1 equiv., 0.125 M) in anhydrous DCM at 0° C. under argon. After 5 min, the mixture was allowed to warm to r.t and left to stir until TLC indicated that no starting material remained (1-2 h). The reaction was then quenched with MeOH and concentrated in vacuo to give the crude decarboxylated isoquinuclidine as the hydroiodide salt, which was used for the next step without further purification. A suspension of sodium bicarbonate (4 equiv.) in anhydrous acetonitrile containing the isoquinuclidine HI salt (0.21 M) and the corresponding alkyl halide (1 equiv.) was stirred at reflux under argon until TLC showed complete consumption of alkyl halide (1-3 days). After cooling to room temperature, the reaction mixture was diluted with water, basified with NaOH, and extracted with CHCl$_3$ (three portions). The combined organic layers were washed with 10% NaHCO$_3$, dried over Na$_2$SO$_4$ or MgSO$_4$, concentrated in vacuo, and purified by flash column chromatography on silica gel.

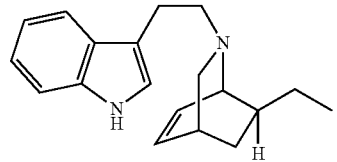 [SMILES: CCC1CC2C=CC1N(CCc1c[nH]c3ccccc13)C2]

exo-2-[2-(1H-indol-3-yl)ethyl]-7-ethyl-2-azabicyclo[2.2.2]oct-5-ene (10a): Purified by flash column chromatography (silica gel, DCM:MeOH=20:1). Brown oil, 62% yield. $^1$H NMR (400 MHz, CDCl$_3$) δ 8.04 (1H, br s), 7.59 (1H, d, J=7.8 Hz), 7.32 (1H, d, J=8.0 Hz), 7.16 (1H, t, J=7.0 Hz), 7.09 (1H, t, J=7.1 Hz), 7.00 (1H, d, J=1.5 Hz), 6.36 (1H, t, J=7.5 Hz), 6.29 (1H, t, J=7.5 Hz), 3.36 (1H, d, J=9.2 Hz), 3.21 (1H, d, J=9.2 Hz), 2.95-2.77 (3H, m), 2.60 (1H, m), 2.46 (1H, s), 1.98 (1H, ddd, J==9.8, 2.4, 2.4 Hz), 1.65 (2H, m), 1.52 (1H, m), 1.33 (1H, m), 0.97 (1H, dd, J=12.0, 3.0 Hz), 0.91 (3H, t, J=7.0 Hz); $^{13}$C NMR (100 MHz, CDCl$_3$) δ 136.1, 133.2, 132.4, 127.6, 121.8, 121.7, 119.1, 114.5, 111.1, 58.9, 56.2, 55.9, 40.1, 31.4, 29.8, 27.2, 24.1, 12.6.

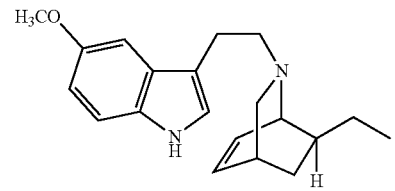 [SMILES: CCC1CC2C=CC1N(CCc1c[nH]c3ccc(OC)cc13)C2]

exo-7-ethyl-2-[2-(5-methoxy-1H-indol-3-yl)ethyl]-2-azabicyclo[2.2.2]oct-5-ene (10b): Pale yellow oil, 65% yield. $^1$H NMR (400 MHz, CDCl$_3$) δ 8.90 (1H, s), 7.28 (2H, m), 6.98 (1H, d, J=2.1 Hz), 6.76 (1H, dd, J=8.8, 2.2 Hz), 6.56 (1H, t, J=7.5 Hz), 6.30 (1H, t, J=6.7 Hz), 4.07 (1H, d, J=5.7 Hz), 3.87 (3H, s), 3.81 (1H, d, J=10.1 Hz), 3.28 (1H, m), 3.13 (2H, m), 2.73 (2H, m), 2.09 (1H, m), 1.92 (1H, d, J=7.7 Hz), 1.83 (1H, d, J=7.0 Hz), 1.59 (2H, m), 1.10 (1H, d, J=11.8 Hz), 0.91 (3H, t, J=7.3 Hz); $^{13}$C NMR (100 MHz, CDCl$_3$) δ 153.8, 137.5, 131.0, 127.6, 127.0, 123.5, 112.2, 112.1, 108.9, 100.7, 57.1, 56.5, 55.5, 37.9, 28.7, 26.8, 26.7, 21.3, 12.1; m/z calcd for C$_{20}$H$_{26}$N$_2$O 310.20, found 311.0.

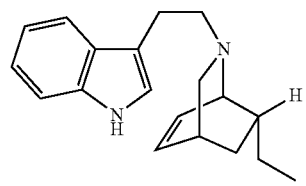 [SMILES: CCC1CC2C=CC1N(CCc1c[nH]c3ccccc13)C2]

endo-2-[2-(1H-indol-3-yl)ethyl]-7-ethyl-2-azabicyclo[2.2.2]oct-5-ene (12a): Purified by flash column chromatography (silica gel, DCM:MeOH=10:1). Pale yellow solid, 75% yield. $^1$H NMR (400 MHz, CDCl$_3$) δ 8.36 (1H, s), 7.61 (1H, d, J=7.8 Hz), 7.40 (1H, ddd, J=8.1, 0.8, 0.8 Hz), 7.20 (1H, ddd, J=7.1, 7.1, 1.1 Hz), 7.16 (1H, d, J=2.5 Hz), 7.12 (1H, ddd, J=7.2, 7.2, 1.2 Hz), 6.71 (1H, t, J=7.6 Hz), 6.15 (1H, br s), 4.14 (1H, m), 3.8 (1H, br s), 3.51 (1H, m), 3.39 (1H, m), 3.18 (1H, m), 3.08 (1H, m), 2.88 (2H, m), 2.28 (1H, br s), 2.03 (1H, ddd, 2.9, 7.8, 12.6 Hz), 1.21 (1H, m), 1.05 (1H, m), 0.9 (1H, m), 0.85 (3H, t, J=7.4 Hz); $^{13}$C NMR (100 MHz, CDCl$_3$) δ 138.7, 135.9, 126.4, 124.7, 122.8, 121.8, 119.3, 118.3, 111.6, 109.1, 57.4, 56.5, 52.1, 35.3, 28.9, 27.6, 27.4, 20.5, 10.7.

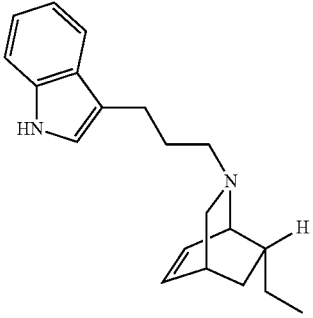 [SMILES: CCC1CC2C=CC1N(CCCc1c[nH]c3ccccc13)C2]

endo-2-[3-(1H-indol-3-yl)propyl]-7-ethyl-2-azabicyclo[2.2.2] oct-5-ene (12b): Pale yellow oil, 65% yield. $^1$H NMR (400 MHz, CDCl$_3$) δ 7.94 (1H, s), 7.60 (1H, d, J=7.9 Hz), 7.35 (1H, ddd, J=8.1, 0.9, 0.9 Hz), 7.18 (1H, ddd, J=7.9, 7.0, 1.1 Hz), 7.10 (1H, ddd, J=7.9, 7.0, 1.1 Hz), 6.98 (1H, d, J=2.2 Hz), 6.36 (1H, dd, J=7.6, 7, 6 Hz), 6.10 (1H, dd, J=7.4, 5.4 Hz), 3.33 (1H, s), 2.97 (1H, d, J=9.4 Hz), 2.74 (2H, t, J=7.7 Hz), 2.61 (1H, m), 2.46 (1H, s), 2.35 (1H, td, 10.4, 5.2 Hz), 1.91 (4H, m), 1.76 (1H, ddd, J=12.1, 9.2, 2.8 Hz), 1.14 (1H, m), 0.98 (1H, m), 0.83 (3H, t, J=7.3 Hz), 0.75 (1H, dddd, J=7.5, 5.5, 4.9, 2.8 Hz); m/z calcd for C$_{20}$H$_{26}$N$_2$ 294.21, found 295.09.

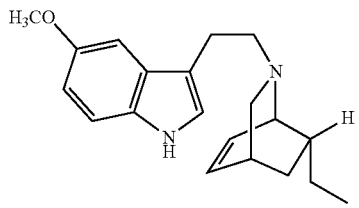 [SMILES: CCC1CC2C=CC1N(CCc1c[nH]c3ccc(OC)cc13)C2]

endo-7-ethyl-2-[2-(5-methoxy-1H-indol-3-yl)ethyl]-2-azabicyclo [2.2.2]oct-5-ene (12c): 50% yield. $^1$H NMR (400 MHz, CDCl$_3$) δ 8.11 (1H, s), 7.27 (1H, d, J=8.8 Hz), 7.23 (1H, s), 7.10 (1H, d, J=1.5 Hz), 6.87 (1H, dd, J=8.8, 2.4 Hz), 6.73 (1H, m), 6.15 (1H, m), 4.17 (1H, d, J=4.9 Hz), 3.92 (3H, s), 3.86 (1H, d, J=10.4 Hz), 3.44 (2H, m), 3.10 (2H, m), 2.93 (2H, m), 2.25 (1H, d, J=10.1 Hz), 2.05 (1H, m), 1.24 (1H, m), 1.06 (1H, m), 0.92 (1H, d, J=11.8 Hz), 0.86 (3H, t, J=7.3 Hz); $^{13}$C NMR (100 MHz, CDCl$_3$) δ 154.7, 139.1, 131.6, 127.5, 124.7, 123.3, 112.6, 112.2, 110.0, 100.6, 60.8, 57.4, 56.6, 52.7, 29.2, 28.1, 21.3, 10.8; m/z calcd for C$_{20}$H$_{26}$N$_2$O 310.20, found 311.1.

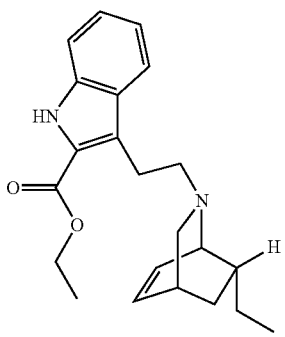 [SMILES: CCOC(=O)c1[nH]c2ccccc2c1CCN1CC2C=CC1C(CC)C2]

endo-ethyl-3-[2-(7-ethyl-2-azabicyclo[2.2.2]oct-5-en-2-yl)ethyl]-1H-indole-2-carboxylate (12d): endo-7-ethyl-2-azabicyclo[2.2.2]oct-5-ene hydroiodide (106 mg, 0.40 mmol) and triethylamine (111 μL, 81 mg, 0.80 mmol) were combined in dry dichloroethane (4 mL) under argon. ethyl 3-(2-oxoethyl)-1H-indole-2-carboxylate (92 mg, 0.40 mmol) and sodium triacetoxyborohydride (170 mg, 0.80 mmol) were then added and the mixture was stirred at room temperature until TLC indicated that no starting material remained. The reaction was then quenched with H$_2$O (20 mL) and extracted with CHCl$_3$ (3×10 mL). The combined organics were washed with H$_2$O (10 mL) and brine (10 mL), dried over Na$_2$SO$_4$, and concentrated to yield the crude product. This was purified by flash column chromatography (silica gel, EtOAc+1% Et$_3$N) to yield a yellow solid (90 mg, 64% yield). $^1$H NMR (400 MHz, CDCl$_3$) δ 8.74 (1H, s), 7.72 (1H, d, J=8.2 Hz), 7.36 (1H, d, J=8.2 Hz), 7.30 (1H, ddd, J=6.7, 6.7, 1.0 Hz), 7.13 (1H, ddd, J=7.9, 6.7, 1.0 Hz), 6.36 (1H, dd, J=7.3, 7.3 Hz), 6.12 (1H, dd, J=7.4, 5.5 Hz), 4.42 (2H, q, J=7.0 Hz), 3.40 (1H, m), 3.26 (2H, m), 3.07 (1H, dd, J=9.7, 1.9 Hz), 2.80 (1H, m), 2.47 (2H, m), 2.22 (1H, ddd, J=9.6, 2.5, 2.5 Hz), 2.04 (1H, m), 1.79 (1H, ddd, J=12.1, 9.2, 2.8 Hz), 1.43 (3H, t, J=7.1 Hz), 1.17 (1H, m), 1.00 (1H, m), 0.85 (3H, t, J=7.3 Hz), 0.78 (1H, dddd, J=7.4, 5.2, 3.0, 2.8 Hz); $^{13}$C NMR (100 MHz, CDCl$_3$) δ 162.2, 135.8, 133.3, 130.3, 128.0, 125.5, 123.3, 122.6, 120.8, 120.0, 111.6, 60.7, 58.9, 57.4, 54.0, 40.4, 31.4, 30.6, 28.7, 24.1, 14.5, 11.6.

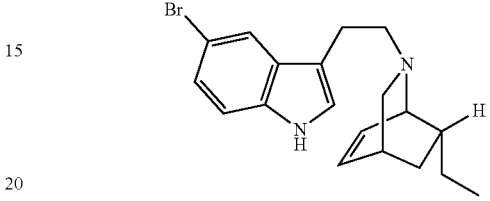

endo-7-ethyl-2-[2-(5-bromo-1H-indol-3-yl)ethyl]-2-azabicyclo[2.2.2]oct-5-ene (12e): White solid, 53% yield. $^1$H NMR (400 MHz, CDCl$_3$) δ 8.03 (1H, s), 7.72 (1H, d, J=0.8 Hz), 7.25 (1H, dd, J=8.7 1.8 Hz), 7.20 (1H, dd, J=8.6, 0.5 Hz), 7.00 (1H, d, J=2.3 Hz), 6.38 (1H, ddd, J=7.8, 6.4, 1.0 Hz), 6.14 (1H, ddd, J=6.5, 5.6, 0.9 Hz), 3.39 (1H, m), 3.03 (1H, ddd, J=9.7, 2.0 Hz), 2.87 (3H, m), 2.52 (2H, m), 2.09 (1H, ddd, J=9.8, 2.8, 2.8 Hz), 2.02 (1H, m), 1.79 (1H, ddd, J=12.2, 9.3, 2.8 Hz), 1.17 (1H, m), 1.00 (1H, m), 0.86 (3H, t, J=7.3 Hz), 0.78 (1H, ddd, J=7.4, 5.2, 3.0, 2.8 Hz); $^{13}$C NMR (100 MHz, CDCl$_3$) δ 135.2, 134.0, 130.5, 129.8, 125.0, 123.1, 122.0, 115.0, 112.8, 112.8, 59.2, 57.5, 54.7, 40.9, 31.8, 30.9, 29.0, 24.7, 12.0; m/z calcd for C$_{19}$H$_{23}$BrN$_2$ 358.10 and 360.10, found 359.33 and 361.33.

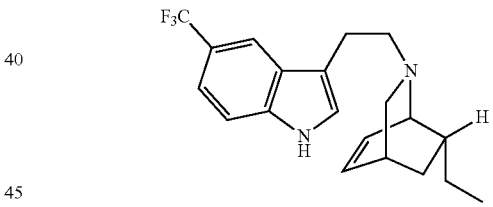

endo-7-ethyl-2-[2-(5-trifluoromethyl-1H-indol-3-yl)ethyl]-2-azabicyclo[2.2.2]oct-5-ene (12f): Pale yellow oil, 65% yield. $^1$H NMR (400 MHz, CDCl$_3$) δ 8.20 (1H, s), 7.89 (1H, s), 7.40 (2H, s), 7.11 (1H, s), 6.40 (1H, dd, J=7.3, 7.3 Hz), 6.14 (1H, dd, J=7.3, 5.6 Hz), 3.42 (1H, s), 3.06 (1H, dd, J=9.7, 1.7 Hz), 2.89 (3H, m), 2.55 (2H, m), 2.10 (1H, ddd, J=9.5, 2.6, 2.6 Hz), 2.04 (1H, m), 1.79 (1H, ddd, J=12.0, 9.2, 2.7 Hz), 1.20 (1H, m), 1.00 (1H, m), 0.85 (3H, t, J=7.3 Hz), 0.79 (1H, m); m/z calcd for C$_{20}$H$_{23}$F$_3$N$_2$ 348.18, found 349.31.

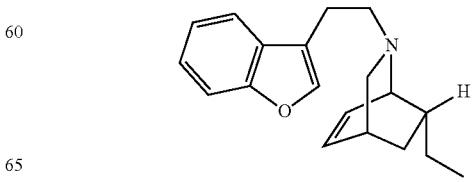

endo-2-[2-(benzofuran-3-yl)ethyl]-7-ethyl-2-azabicyclo[2.2.2]oct-5-ene (12g): Dark brown oil, 50% yield. $^1$H NMR (400 MHz, CDCl$_3$) δ 7.48 (1H, d, J=8.0 Hz), 7.37 (1H, s), 7.17 (2H, m), 6.31 (1H, dd, J=7.3, 7.3 Hz), 6.06 (1H, dd, J=7.3, 6.3 Hz), 3.29 (1H, m), 2.95 (1H, dd, J=9.5, 1.0 Hz), 2.76 (3H, m), 2.46 (2H, m), 2.00 (1H, ddd, J=9.7, 2.3, 2.3 Hz), 1.94 (1H, m), 1.71 (1H, ddd, J=12.1, 9.4, 2.8 Hz), 1.10 (1H, m), 0.93 (1H, m), 0.78 (3H, t, 7.3 Hz), 0.71 (1H, m); $^{13}$C NMR (100 MHz, CDCl$_3$) δ 155.2, 141.3, 133.5, 130.1, 128.3, 124.0, 122.1, 119.6, 118.7, 111.4, 57.8, 57.3, 54.3, 40.7, 31.4, 30.6, 28.7, 23.1, 11.6.

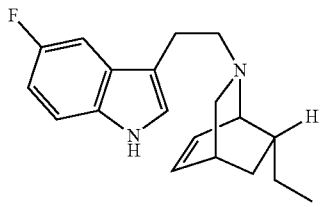 [SMILES: CCC1CC2C=CC1N(CCc1c[nH]c3ccc(F)cc13)C2]

endo-7-ethyl-2-[2-(5-fluoro-1H-indol-3-yl)ethyl]-2-azabicyclo[2.2.2]oct-5-ene (12h): Purified by flash column chromatography (silica gel, hexane:EtOAc=1:1→DCM: MeOH=6:1). Pale brown solid, 51% yield. $^1$H NMR (400 MHz, CDCl$_3$) δ 8.10 (1H, s), 7.21 (2H, m), 7.00 (1H, s), 6.89 (1H, dd, J=9.0 9.0 Hz), 6.38 (1H, dd, J=7.0, 7.0 Hz), 6.14 (1H, dd, J=6.7, 6.7 Hz), 3.41 (1H, s), 3.03 (1H, d, J=9.4 Hz), 2.85 (3H, m), 2.53 (2H, m), 2.08 (2H, m), 1.78 (1H, dd, J=10.4, 10.4 Hz), 1.17 (1H, m), 1.01 (1H, m), 0.82 (4H, m); $^{13}$C NMR (100 MHz, CDCl$_3$) δ 159.1, 156.0, 133.5, 132.7, 130.1, 127.9, 127.8, 123.4, 114.8, 114.7, 111.6, 111.5, 110.2, 109.9, 103.8, 103.5, 58.7, 57.1, 54.2, 40.3, 31.4, 30.6, 28.6, 24.4, 11.6; m/z calcd for C$_{19}$H$_{23}$FN$_2$ 298.18, found 298.61.

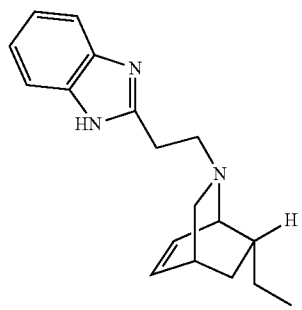 [SMILES: CCC1CC2C=CC1N(CCc1nc3ccccc3[nH]1)C2]

endo-2-[2-(1H-benzo[d]imidazol-2-yl)ethyl]-7-ethyl-2-azabicyclo[2.2.2]oct-5-ene (12i): The crude isoquinuclidine hydroiodide (106 mg, 0.40 mmol), obtained by TMSI deprotection of 8 and triethylamine (0.17 mL, 121 mg, 1.2 mmol) in anhydrous DMF (1.5 mL) was stirred under argon at room temperature for 10 min. 2-(2'-chloroethyl)benzimidazole (72 mg, 0.40 mmol) was then added to the above mixture and the resulting solution was allowed to stir at room temperature overnight. After the workup, the crude mixture was purified by RP-HPLC to afford a pale yellow oil (48 mg, 43% yield). $^1$H NMR (300 MHz, CD$_3$OD) δ 7.68 (2H, dd, J=6.2, 3.2 Hz), 7.48 (2H, dd, J=6.2, 3.1 Hz), 6.75 (1H, dd, J=7.7, 7.7 Hz), 6.25 (1H, dd, J=7.7, 7.7 Hz), 4.25 (1H, d, J=5.2 Hz), 3.60 (3H, m), 3.45 (2H, m), 2.93 (1H, m), 2.80 (1H, d, J=10.5 Hz), 2.14 (1H, m), 1.94 (1H, ddd, J=12.6, 9.1, 2.9 Hz), 1.25 (1H, m), 1.04 (1H, m), 0.94 (1H, dddd, J=7.9, 5.2, 2.6, 2.6 Hz), 0.85 (3H, t, J=7.4 Hz); $^{13}$C NMR (75 MHz, CD$_3$OD) δ 150.5, 140.4, 133.5, 133.5, 127.1, 127.1, 126.0, 115.1, 115.1, 59.9, 53.6, 53.3, 37.1, 30.8, 29.1, 28.9, 23.5, 11.3; m/z calcd for C$_{18}$H$_{23}$N$_3$ 281.19, found 281.73.

EXAMPLE 3

General Procedure and Synthesis of Saturated Derivatives

Figure 4:
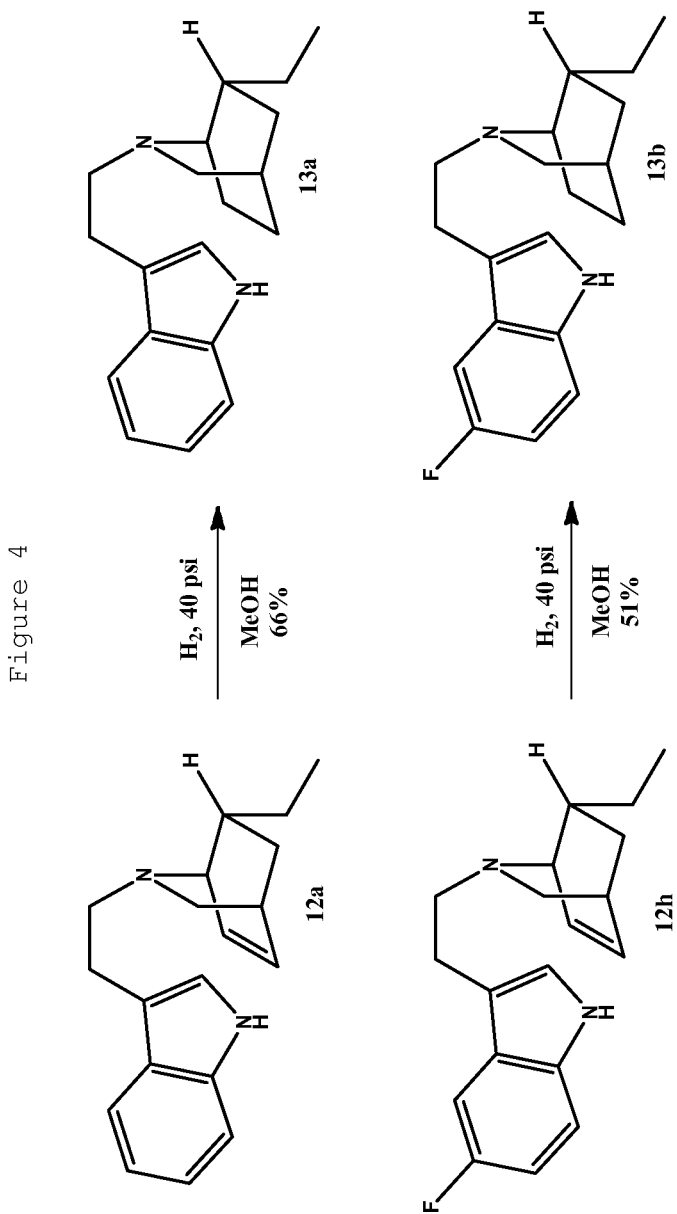
FIG. 4. Synthetic route to unsaturated isoquinuclidine derivatives.

Saturated derivatives were prepared according to the protocols shown in FIG. 4. The alkene starting material 12a or 12h (100 mg) was hydrogenated (H$_2$, 40 psi) over 10% Pd/C (10 mg) catalyst in 15 mL of anhydrous methanol at r.t overnight. The mixture was filtered, concentrated and purified by flash column chromatography (silica gel, EtOAc) to give the pure product.

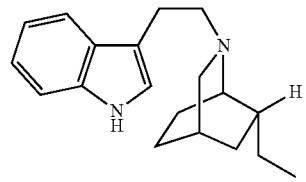 [SMILES: CCC1CC2CCC1N(CCc1c[nH]c3ccccc13)C2]

endo-2-[2-(1H-indol-3-yl)ethyl]-7-ethyl-2-azabicyclo[2.2.2]octane (13a): pale yellow oil (66 mg, 66% yield). $^1$H NMR (400 MHz, CDCl$_3$) δ 7.99 (1H, s), 7.65 (1H, d, J=7.8 Hz), 7.36 (1H, ddd, J=8.1, 0.9, 0.9 Hz), 7.19 (1H, ddd, J=7.1, 7.1, 1.2 Hz), 7.11 (1H, ddd, J=8.0, 7.2, 1.1 Hz), 7.04 (1H, d, J=2.2 Hz), 2.94 (3H, m), 2.85 (2H, m), 2.72 (1H, ddd, J=9.7, 2.2, 2.2 Hz), 2.51 (1H, m), 1.86 (3H, m), 1.63 (3H, m), 1.46 (1H, m), 1.29 (2H, m), 1.03 (1H, m), 0.88 (3H, t, J=7.3 Hz); $^{13}$C NMR (100 MHz, CDCl$_3$) δ 136.6, 128.0, 122.3, 121.8, 119.5, 119.4, 115.5, 119.4, 115.5, 111.4, 57.6, 56.5, 54.1, 35.9, 33.3, 27.9, 27.0, 25.6, 24.8, 20.5, 12.4.

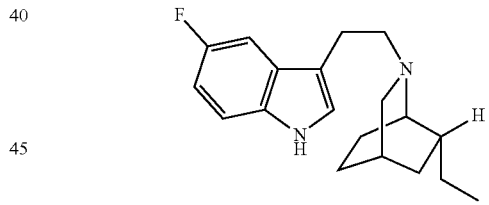

endo-7-ethyl-2-[2-(5-fluoro-1H-indol-3-yl)ethyl]-2-azabicyclo [2.2.2]octane (13b): Pale yellow oil, 70% yield. $^1$H NMR (400 MHz, CDCl$_3$) δ 8.20 (1H, s), 7.26 (2H, m), 7.09 (1H, s), 6.93 (1H, dd, J=8.7 8.7 Hz), 2.88 (4H, m), 2.72 (1H, d, J=9.8 Hz), 2.52 (1H, s), 1.86 (3H, m), 1.66 (3H, m), 1.47 (1H, m), 1.31 (3H, m), 1.03 (1H, m), 0.89 (3H, t, 7.3 Hz); $^{13}$C NMR (100 MHz, CDCl$_3$) δ 159.6, 133.1, 128.4, 123.7, 115.7, 112.0 and 111.9, 110.8 and 110.4, 104.5 and 104.2, 57.4, 56.5, 54.2, 35.9, 33.2, 27.9, 27.0, 25.6, 24.7, 20.5, 12.4; m/z calcd for C$_{19}$H$_{23}$FN$_2$ 300.20, found 301.08.

EXAMPLE 4

Synthesis of Unsubstituted Isoquinuclidines

Figure 5:
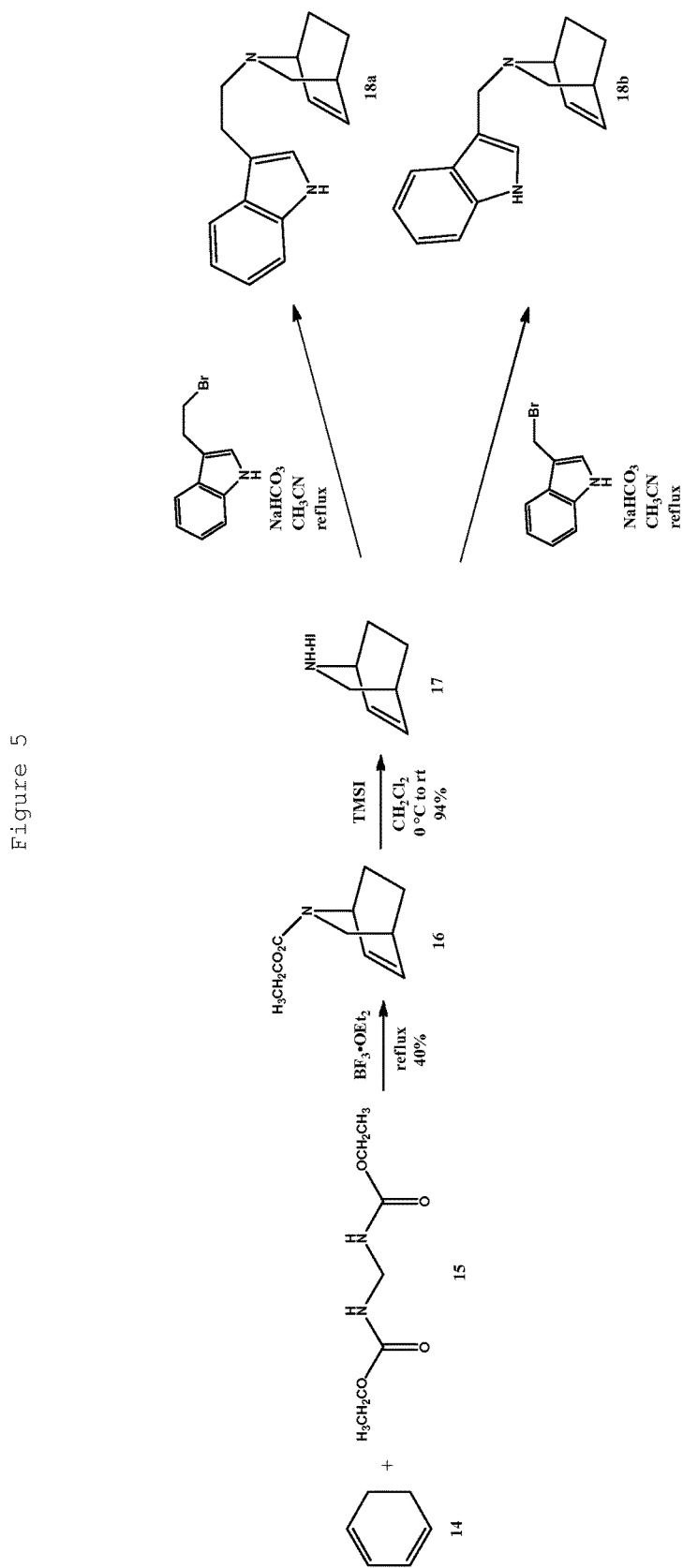
FIG. 5. Synthetic route to unsubstituted isoquinuclidine derivatives.

Unsubstituted Isoquinuclidine derivatives were prepared according to the protocols shown in FIG. 5. A solution of BF$_3$-etherate (1.60 mL, 13.0 mmol) and methylene bisurethane (9.89 g, 52 mmol) in 70 mL of benzene was brought to reflux. A solution of 1,3-hexadiene in 10 mL of benzene was then added dropwise and the mixture was refluxed for 1 hr. After cooling, the mixture was washed with saturated NaHCO₃ and water, dried over MgSO₄, and concentrated in vacuo to yield an oily residue. This was distilled under vacuum to yield the product (16, 45% yield) (Borne, R. F. et al, 1973)). Deprotection with iodotrimethylsilane to salt 17 (94% yield) and coupling with 3-(2-bromoethyl)-1H-indole or 3-(bromomethyl)-1H-indole using the general procedures as described in Example 2 gave unsubstituted derivatives 18a and 18b.

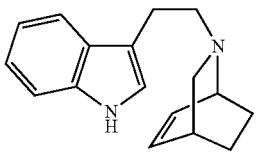 [SMILES: C1=CC2CCC1CN2CCc1c[nH]c2ccccc12]

2-[2-(1H-indol-3-yl)ethyl]-2-azabicyclo[2.2.2]oct-5-ene (18a): Purified by flash column chromatography (silica gel, EtOAc→DCM: MeOH=6:1) afforded the product (64% yield). ¹H NMR (400 MHz, CDCl₃) δ 7.97 (1H, s), 7.58 (1H, d, J=8.0 Hz), 7.33 (1H, d, J=8.0 Hz), 7.16 (1H, ddd, J=8.2, 7.2, 1.3 Hz), 7.09 (1H, ddd, J=7.0, 7.0, 1.0 Hz), 7.01 (1H, d, J=2.0 Hz), 6.44 (1H, t, J=7.0 Hz), 6.25 (1H, t, J=5.6 Hz), 3.65 (1H, s), 3.22 (1H, d, J=9.3 Hz), 2.96 (3H, m), 2.62 (2H, m), 2.19 (2H, d, J=9.8 Hz), 1.64 (1H, dd, J=10.9, 10.9 Hz), 1.29 (2H, m); m/z calcd for C₁₇H₂₀N₂ 252.16, found 253.22.

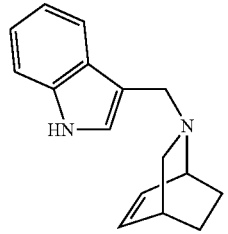 [SMILES: C1=CC2CCC1CN2Cc1c[nH]c2ccccc12]

2-[(1H-indol-3-yl)methyl]-2-azabicyclo[2.2.2]oct-5-ene (18b): Purified by flash column chromatography (silica gel, EtOAc→DCM:MeOH=6:1). Pale yellow solid, 66% yield. ¹H NMR (400 MHz, CDCl₃) δ 8.21 (1H, s), 7.70 (1H, d, J=7.9 Hz), 7.33 (1H, ddd, J=8.1, 0.9, 0.9 Hz), 7.17 (2H, m), 7.10 (1H, ddd, J=7.9, 7.0, 1.2 Hz), 6.44 (1H, t, J=7.3 Hz), 6.29 (1H, ddd, J=8.1, 5.4, 1.2 Hz), 3.76 (1H, d, J=13.3 Hz), 3.62 (1H, d, J=13.4 Hz), 3.49 (1H, m), 3.09 (1H, dd, J=9.8, 1.9 Hz), 2.51 (1H, m), 2.10 (1H, ddd, J=9.9, 2.7, 2.7 Hz), 1.98 (1H, m), 1.57 (1H, m), 1.22 (2H, m); ¹³C NMR (100 MHz, CDCl₃) δ 136.1, 133.8, 131.4, 127.8, 123.7, 121.8, 119.3, 119.1, 113.3, 111.1, 55.2, 52.4, 51.0, 30.8, 26.4, 22.0; m/z calcd for C₁₆H₈N₂ 238.15, found 238.86.

EXAMPLE 5

Synthesis of Ethyl Ester Derivatives

Figure 6:
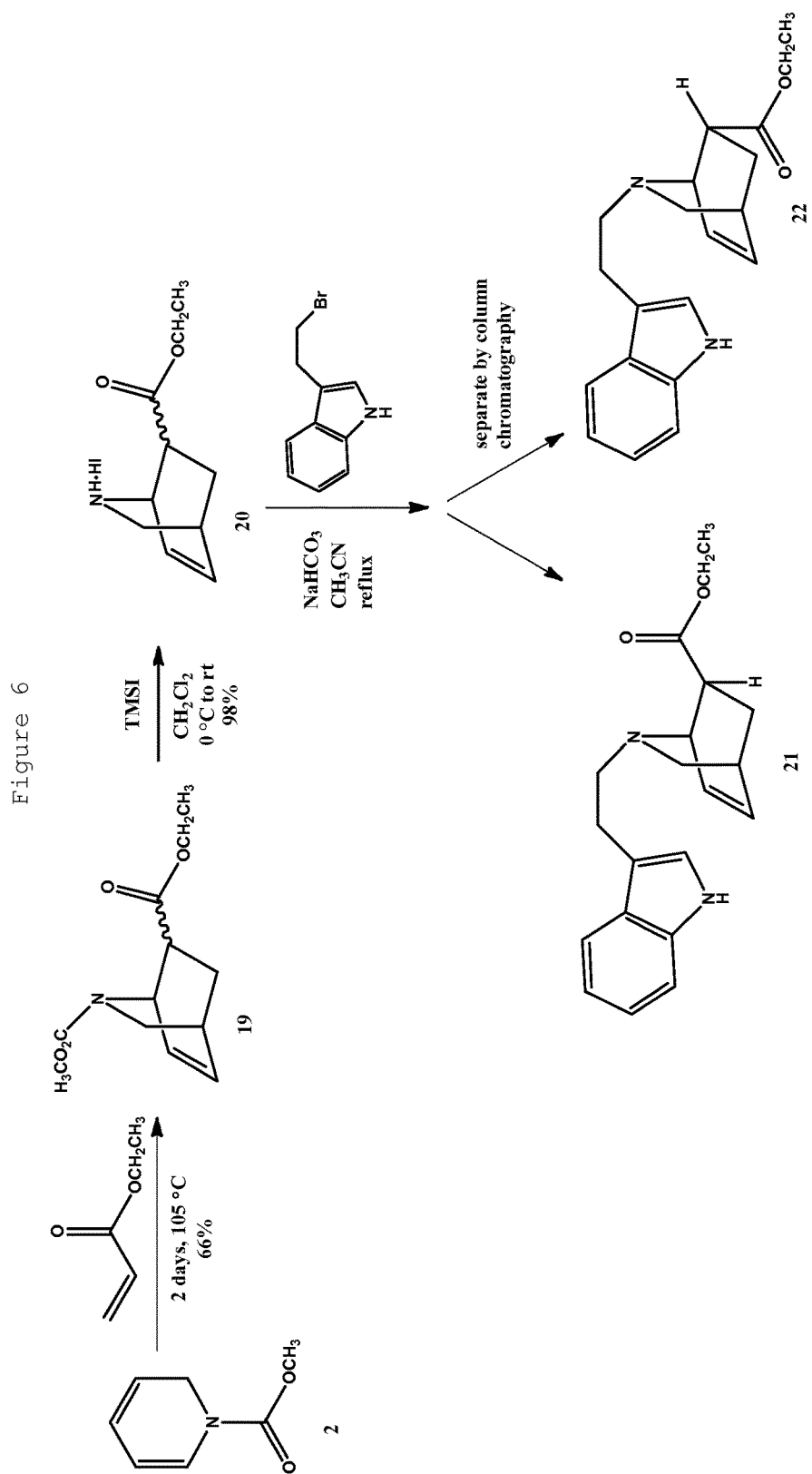
FIG. 6. Synthetic route to ethyl ester derivatives.

Ethyl ester derivatives were prepared according to the protocols shown in FIG. 6. N-methoxycarbonyldihydropyridine 2 (1.12 g, 8.00 mmol) and ethyl acrylate (4.34 mL, 40.0 mmol) were combined and heated at 105° C. for two days under argon. After removing the volatiles in vacuo, the mixture was purified by flash column chromatography (silica gel, hexane:EtOAc=3:1) to yield a colorless oil (C-074, 1.26 g, 66% yield). Deprotection with iodotrimethylsilane to salt 20 (98% yield) and coupling with 3-(2-bromoethyl)-indole using the general procedures described in Example 2, followed by separation and purification by flash column chromatography (silica gel, 1% Et3N in EtOAc) afforded the pure exo-product 21 and pure endo-product 22.

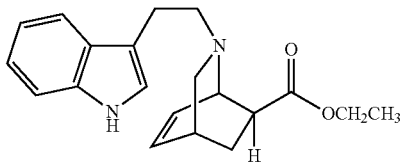 [SMILES: CCOC(=O)C1CC2C=CC1N(CCc1c[nH]c3ccccc13)C2]

7-exo-ethoxycarbonyl-2-[2-(1H-indol-3-yl)ethyl]-2-azabicyclo[2.2.2]oct-5-ene (21): Pale yellow oil, 135.2 mg, 21% yield). ¹H NMR (400 MHz, CDCl₃) δ 7.92 (1H, s), 7.55 (1H, d, J=7.9 Hz), 7.33 (1H, d, J=8.1 Hz), 7.16 (1H, ddd, J=8.2, 7.2, 1.4 Hz), 7.09 (1H, ddd, J=8.0, 7.9, 1.1 Hz), 7.02 (1H, d, J=2.0 Hz), 6.47 (1H, ddd, J=7.9, 6.6, 1.0 Hz), 6.26 (1H, ddd, J=7.9, 5.5, 1.2 Hz), 4.07 (2H, m), 3.91 (1H, m), 3.23 (1H, dd, J=9.2, 2.1 Hz), 2.78 (3H, m), 2.57 (1H, m), 2.44 (2H, m), 2.19 (1H, ddd, J=12.8, 4.3, 2.6 Hz), 1.39 (1H, m), 1.18 (3H, t, J=7.1 Hz); ¹³C NMR (100 MHz, CDCl₃) δ 175.0, 136.5, 135.5, 130.3, 128.0, 122.0, 122.0, 119.4, 199.1, 115.1, 111.4, 60.7, 58.7, 55.4, 55.3, 45.8, 31.4, 24.6, 24.4, 14.6; m/z calcd for C₁₆H₁₈N₂ 324.18, found 324.69.

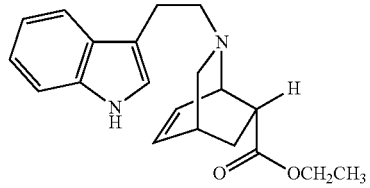 [SMILES: CCOC(=O)C1CC2C=CC1N(CCc1c[nH]c3ccccc13)C2]

7-endo-ethoxycarbonyl-2-[2-(1H-indol-3-yl)ethyl]-2-azabicyclo[2.2.2]oct-5-ene (22): Pale brown oil, 224.5 mg, 35% yield). ¹H NMR (400 MHz, CDCl₃) δ 8.02 (1H, s), 7.61 (1H, d, J=8.0 Hz), 7.35 (1H, d, J=8.0 Hz), 7.19 (1H, ddd, J=8.1, 7.1, 1.2 Hz), 7.11 (1H, ddd, J=7.9, 7.0, 1.1 Hz), 7.00 (1H, d, J=2.2 Hz), 6.45 (1H, dd, J=7.4, 7.4 Hz), 6.19 (1H, ddd, J=8.0, 5.4, 1.2 Hz), 4.10 (2H, m), 3.91 (1H, m), 3.13 (1H, ddd, J=8.3, 5.1, 3.2 Hz), 3.03 (1H, dd, J=9.6, 2.1 Hz), 2.90 (3H, m), 2.60 (2H, m), 2.14 (1H, ddd, J=9.5, 2.5, 2.5 Hz), 1.77 (2H, m), 1.24 (3H, t, J=7.1 Hz); ¹³C NMR (100 MHz, CDCl₃) δ 174.0, 136.1, 134.6, 129.7, 127.5, 121.8, 121.4, 119.1, 118.8, 114.5, 111.0, 60.4, 58.7, 54.7, 54.4, 43.7, 30.7, 26.0, 24.4, 14.3; m/z calcd for C₁₆H₁₈N₂ 324.18, found 324.92.

EXAMPLE 6

Figure 7:
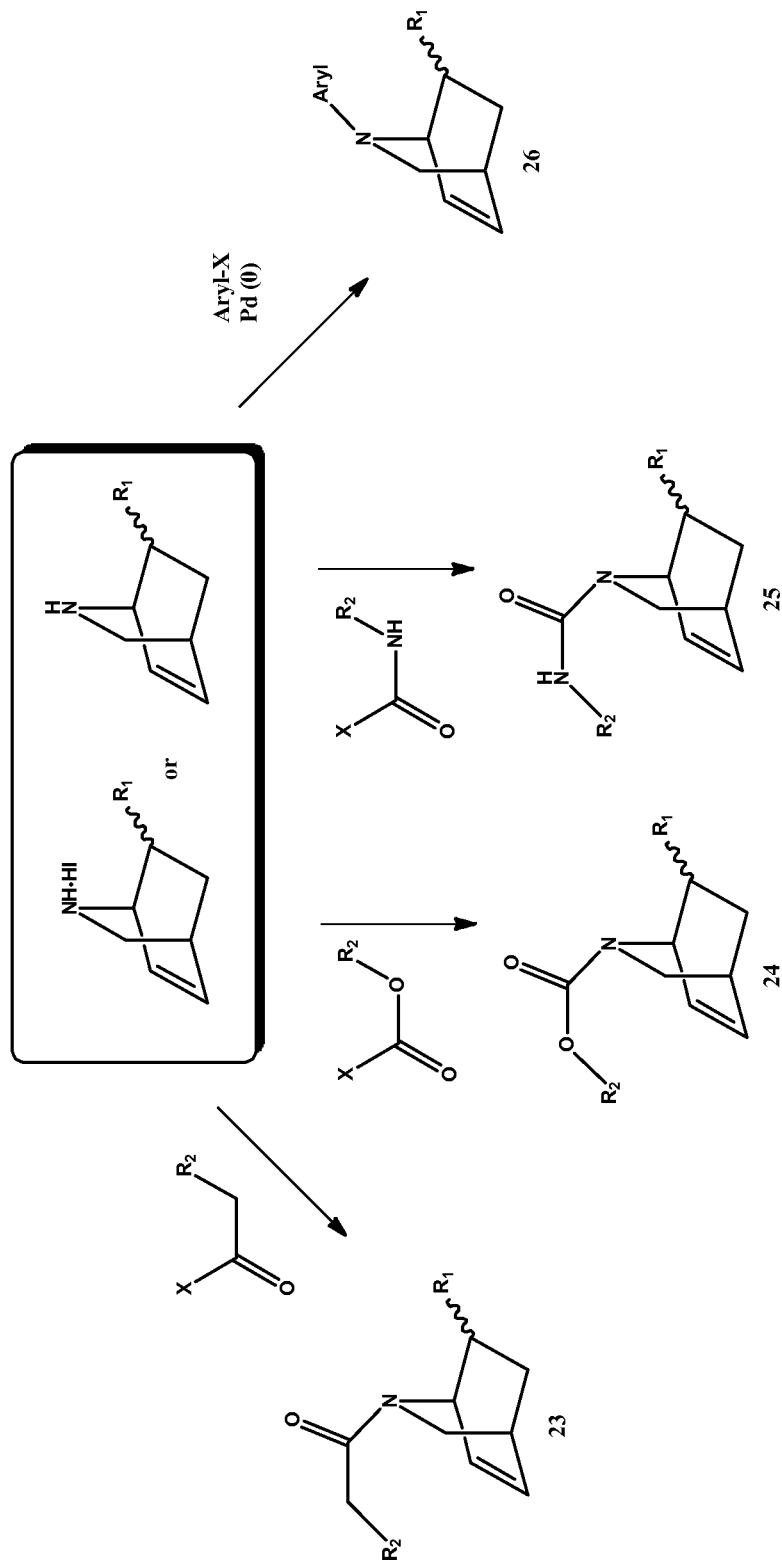
FIG. 7. Synthesis of isoquinuclidines with various linkers or direct attachment to aryl group.

General Procedure for Synthesis of Isoquinuclidines with Various Linkers or Direct Attachment to Aryl Group Additional isoquinuclidine derivatives are synthesized according to the scheme in FIG. 7. Reaction of the intermediate HI salt or free amine with acid chlorides gives amide derivative 23. Reaction of the HI salt or the free amine with chloroformate esters gives isoquinuclidine derivative 24 with a carbamate linker. Reaction of the HI salt or the free amine with phosgene or a phosgene equivalent allows for access to a carbamoyl chloride intermediate, which is trapped with the isoquinulidine free amine to give isoquinuclidine derivative 25 with a urea linker. Reaction of the HI salt or free amine with aryl or heteroaryl halides via a metal-catalyzed coupling reaction gives isoquinuclidine derivative 26 with a direct aryl-amine connection.

EXAMPLE 7

General Procedure for Synthesis of Ketone Derivatives

Figure 8:
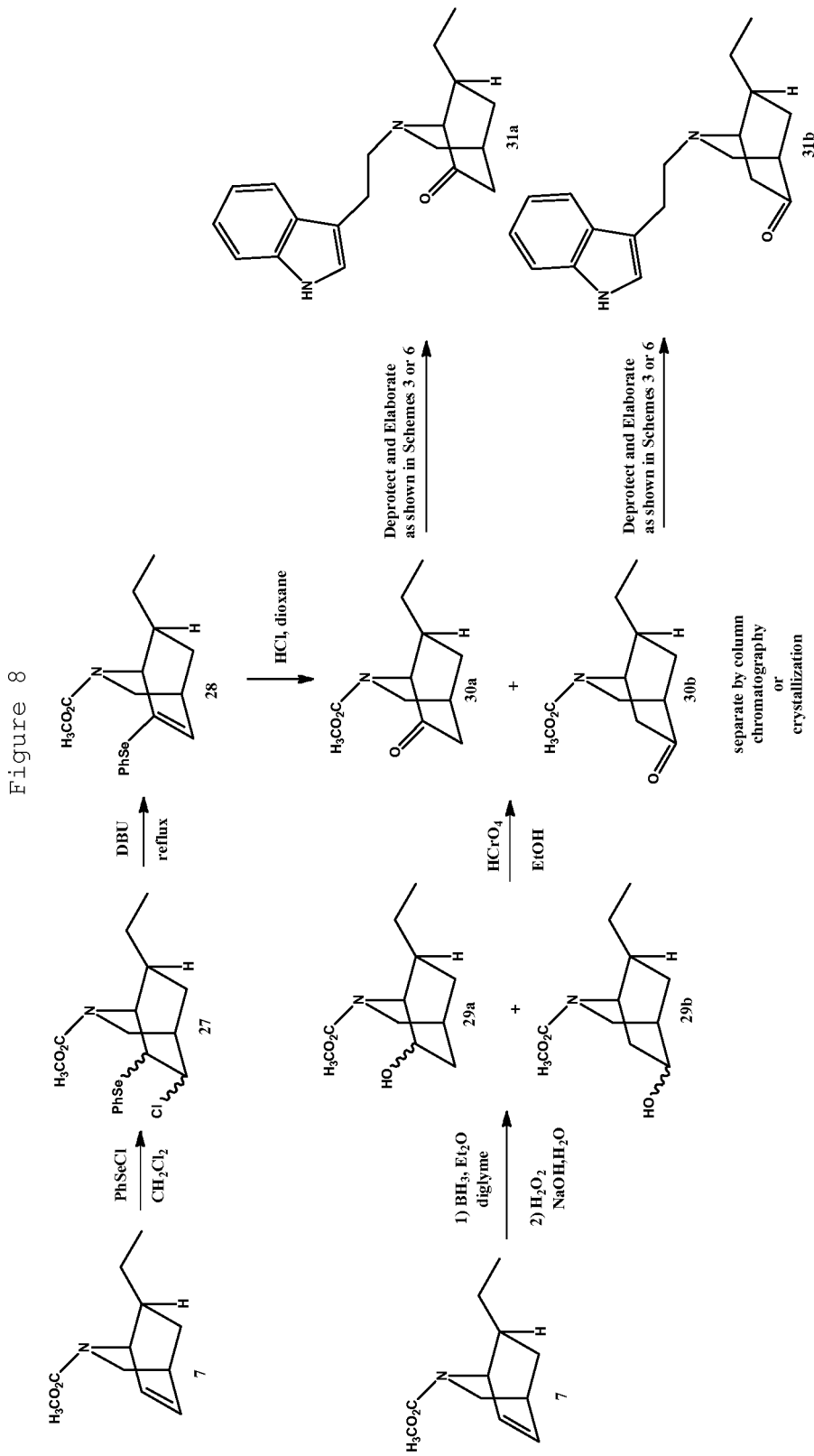
FIG. 8. Synthetic route to ketone derivatives.
Figure 9:
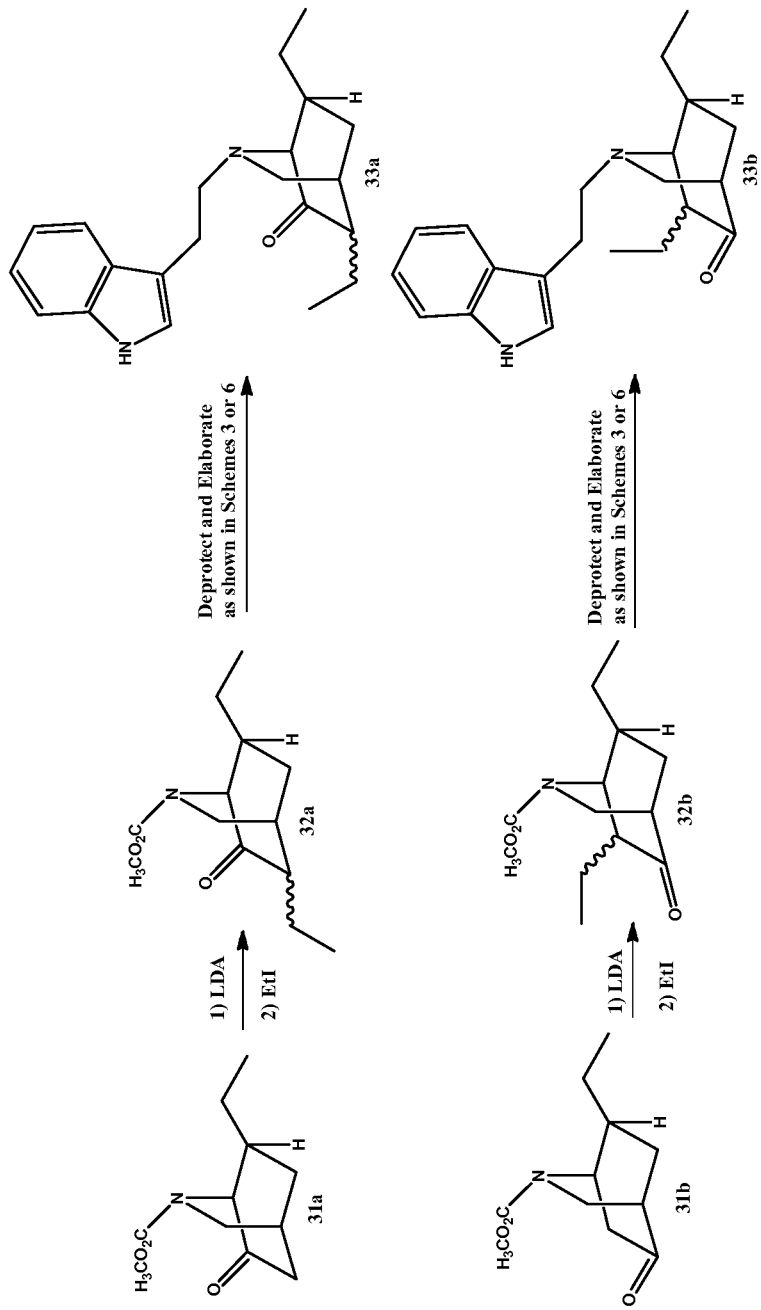
FIG. 9. Synthetic route to α-substituted ketone derivatives.

Ketone and α-substituted ketone derivatives are synthesized according to the schemes in FIGS. 8 and 9. Alkene selenenylation of alkene 7 and elimination the resulting alkyl chloride 27 gives selenide 28, which under acidic conditions is converted to ketone 30a (13). Alternatively, sequential oxidations of intermediate 7 generates ketones 30a and 30b, which are separated by chromatography or crystallization (Cava, M. P. et al. 1965). Deprotection with iodotrimethylsilane to the iodide salt and coupling with 3-(2-bromoethyl)-1H-indole using the general procedures described in Example 2 gives ketone derivatives 31a or 31b (FIG. 8). Ketones 30a and 30b are also deprotonated by lithium diisopropylamide (LDA) in the presence of an alkyl iodide which generates α-substituted ketones 32a and 32b. Deprotection with iodotrimethylsilane to the iodide salt and coupling with 3-(2-bromoethyl)-1H-indole using the general procedures described in Example 2 gives α-substituted ketone derivatives 33a or 33b (FIG. 9).

EXAMPLE 8

General Procedure for Synthesis of Substituted Alkene Derivatives

Figure 10:
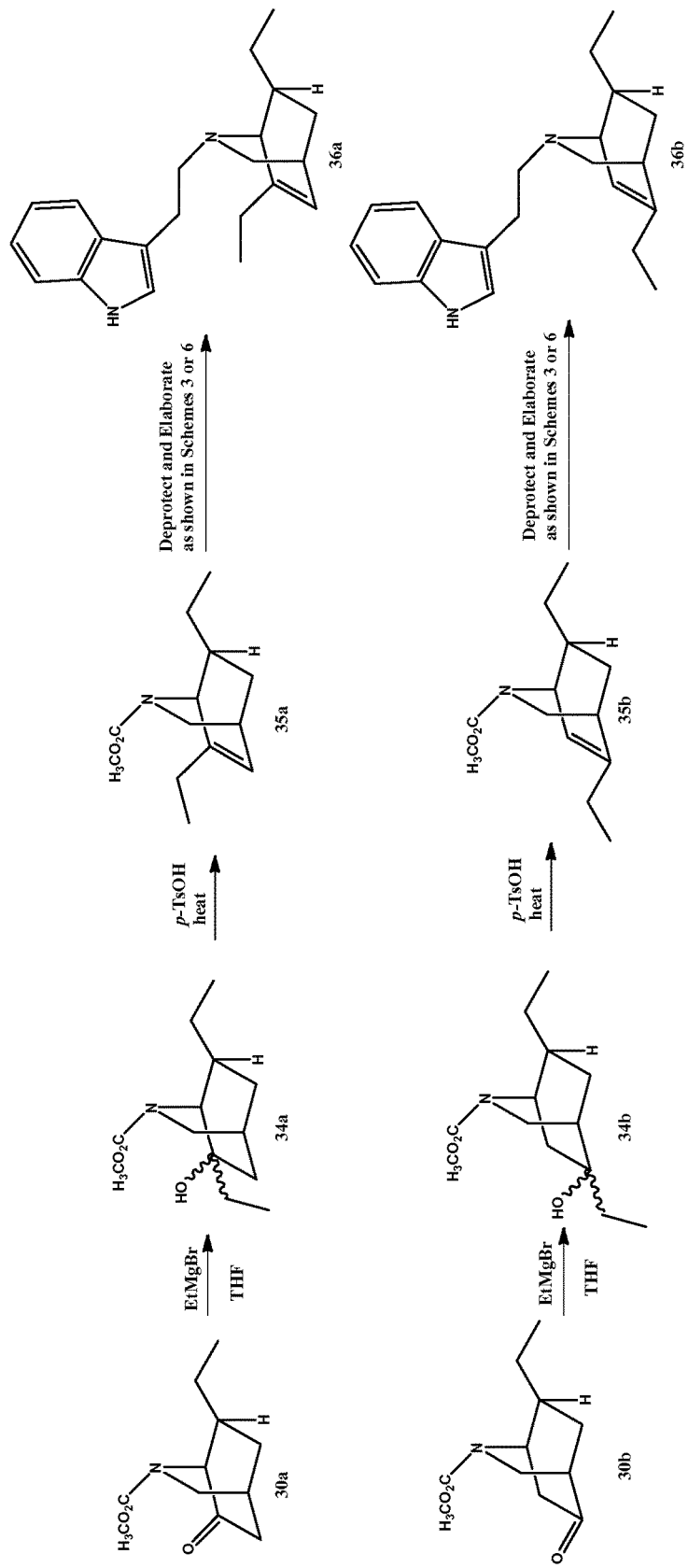
FIG. 10. Synthetic route to substituted alkene derivatives.

Substituted alkene derivatives are synthesized according to the scheme in FIG. 10. Ketones 30a and 30b are treated with a Grignard reagent in THF which generates alcohols 34a and 34b. Elimination under acidic conditions gives alkenes 35a and 35b. Deprotection with iodotrimethylsilane to the iodide salt and coupling with 3-(2-bromoethyl)-1H-indole using the general procedures described in Example 2 gives substituted alkene derivatives 36a or 36b.

EXAMPLE 9

General Procedure for Synthesis of 8-Substituted Derivatives

Figure 11:
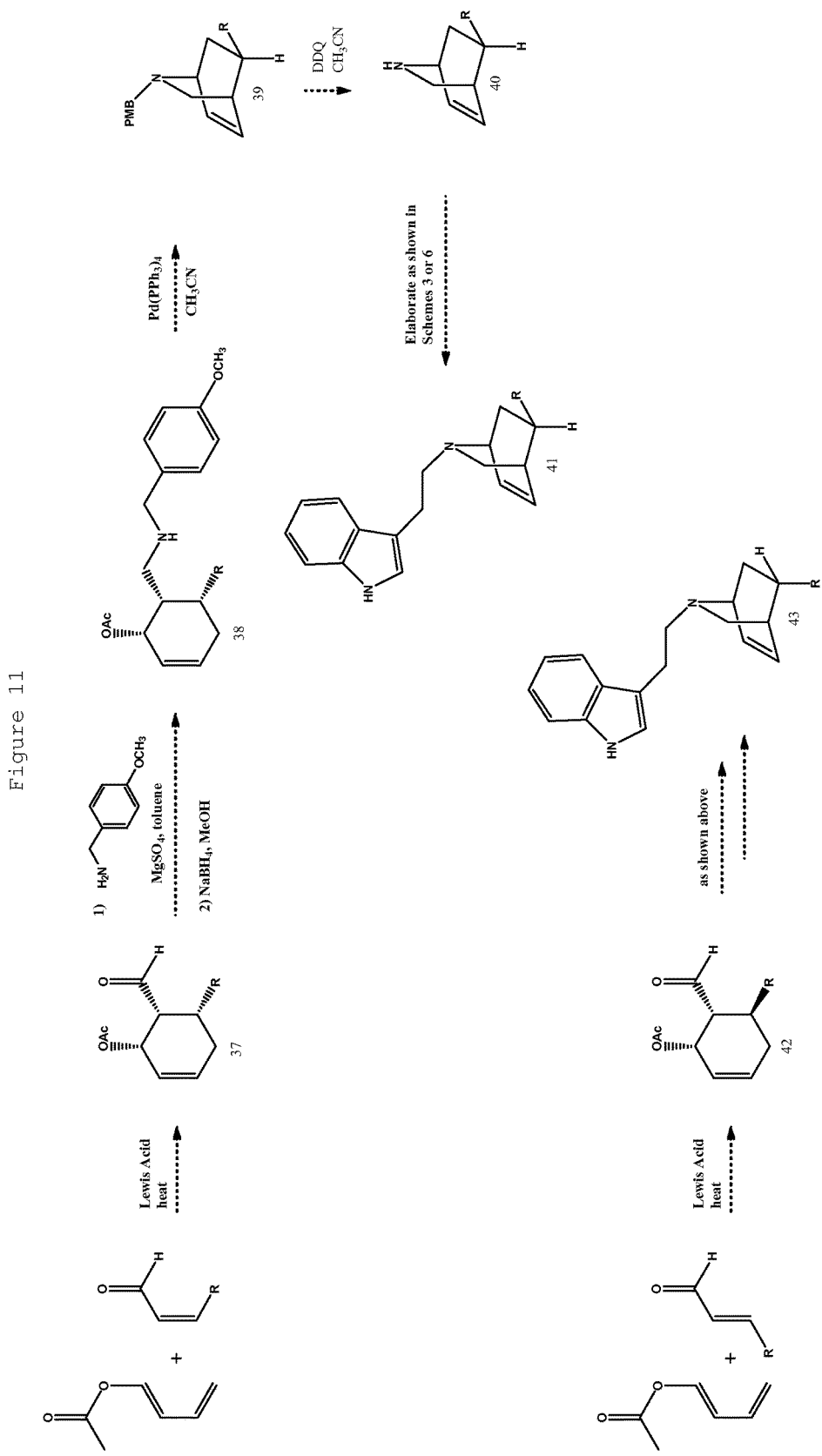
FIG. 11. General synthetic route towards 5-substituted isoquinuclidine derivatives.

5-Substituted derivatives are synthesized according to the scheme in FIG. 11. Reductive amination of aldehyde 37 gives 38, which is primed for a palladium-catalyzed cyclization to isoquinuclidine core 39 (Trost, B. et al. 1976). Deprotection with 2,3-Dichloro-5,6-dicyano-1,4-benzoquinone (DDQ) to the free amine and coupling with 3-(2-bromoethyl)-1H-indole using the general procedure described in Example 2 gives 5-substituted exo derivative 41. The endo derivative 43 is prepared by a similar sequence.

EXAMPLE 10

General Procedure for Synthesis of 7-Non-Ethyl Substituted Derivatives

Figure 12:
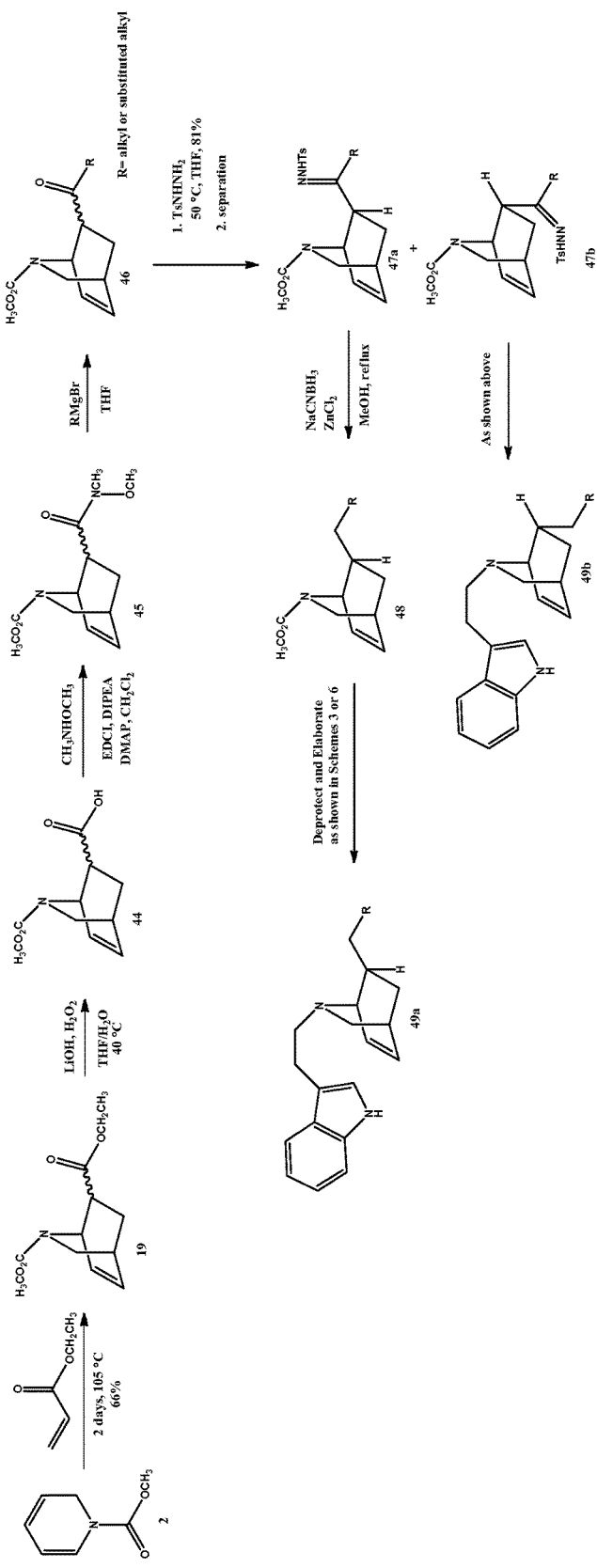
FIG. 12. General synthetic route to 7-non-ethyl substituted isoquinuclidine derivatives.

7-Non-ethyl substituted derivatives are synthesized according to the scheme in FIG. 12. Ethyl ester 19 is hydrozlyzed under basic conditions to acid 44, which is coupled to N,O-dimethylhydroxylamine. Weinreb amide 45 is treated with a Grignard reagent in THF which generates ketone 46. Formation and separation of the tosylhydrazones followed by reduction gives compound 48. Deprotection with iodotrimethylsilane to the iodide salt and coupling with 3-(2-bromoethyl)-1H-indole using the general procedures described in Example 1 and 2 gives 7-non-ethyl substituted derivative 49a. The endo derivative 49b is prepared by a similar sequence.

EXAMPLE 11

Figure 13:
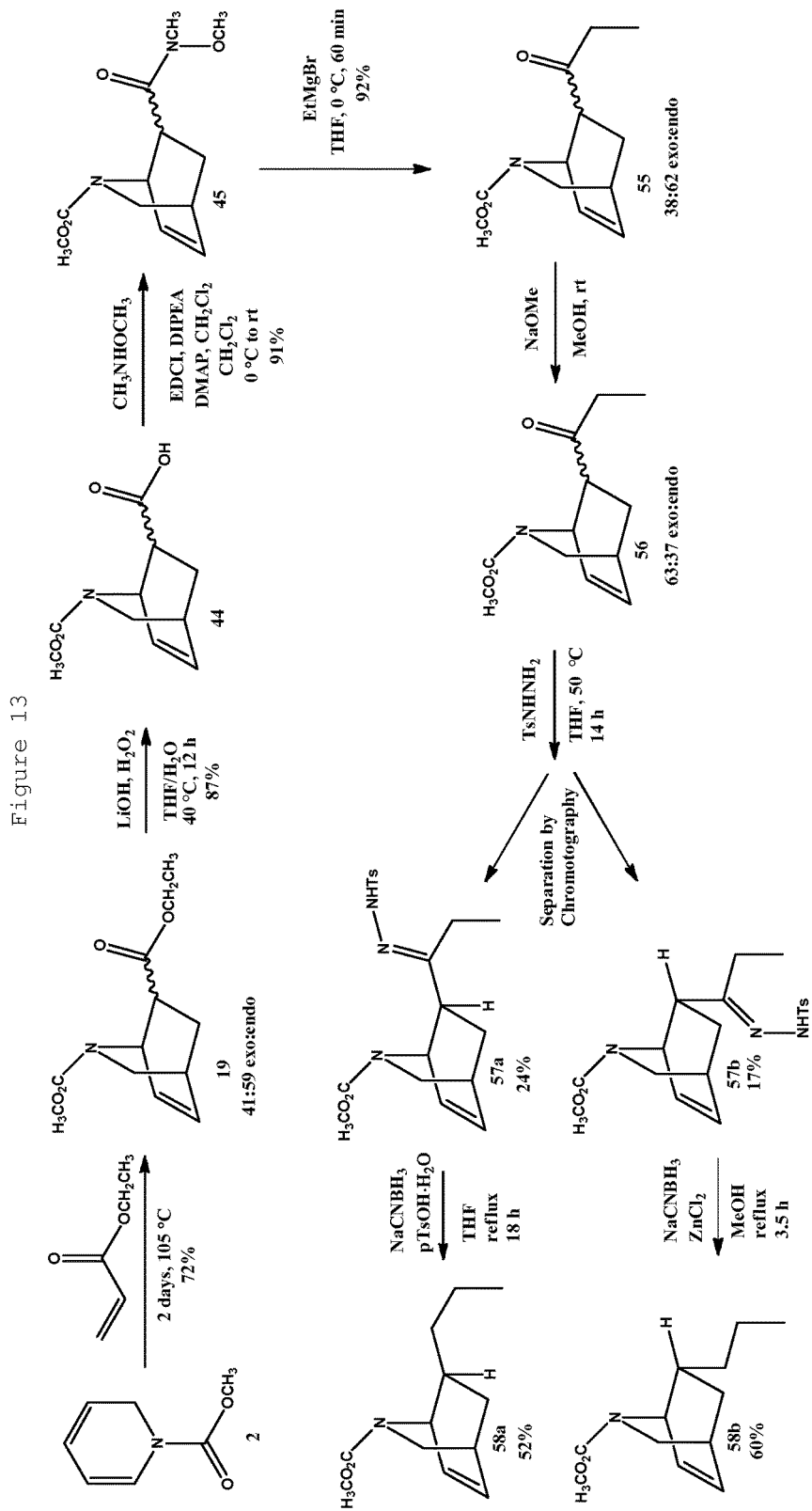
FIG. 13. Synthesis of 7-propyl isoquinuclidine intermediates.
Figure 14:
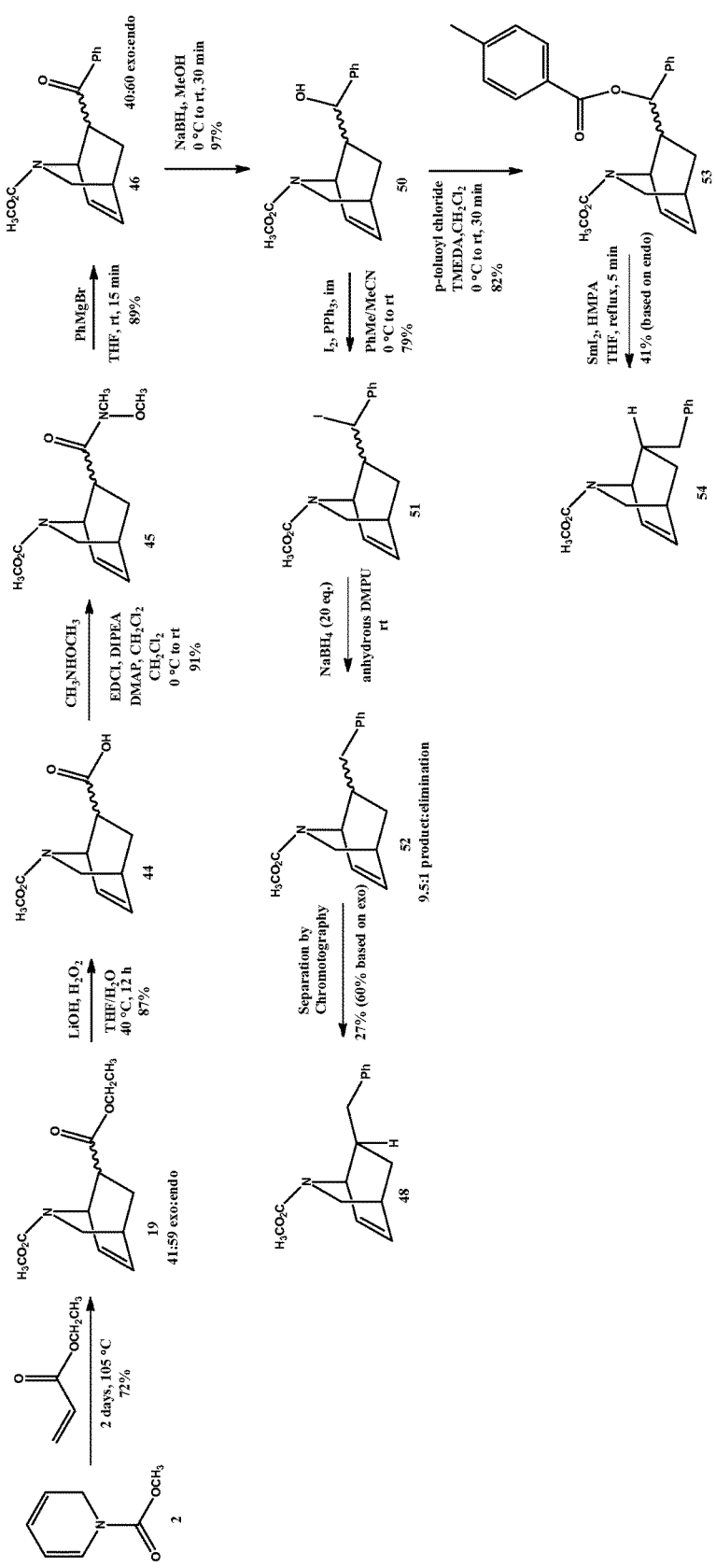
FIG. 14. Synthesis of 7-benzyl isoquinuclidine intermediates.

Preparation of Intermediates for the Synthesis of Isoquinuclidines Derivatives Key intermediates 58a, 58b, 48 and 54 were synthesized according to the scheme in FIGS. 13 and 14. Weinreb amide 45 was treated with a Grignard reagent in THF which generated ketone 55. Formation and separation of the tosylhydrazones followed by reduction gave key intermediates 58a and 58b (FIG. 13). Alternatively, ketone 46 was reduced to alcohol 50, which was converted to key intermediates 48 and 54.

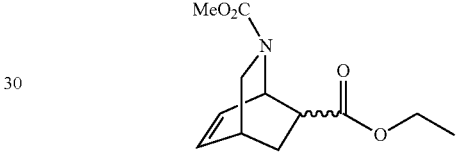

exo/endo-7-ethyl 2-methyl 2-azabicyclo[2.2.2]oct-5-ene-2,7-dicarboxylate (19): N-(methoxycarbonyl)-1,2-dihydropyridine (22.9 g, 165 mmol) was combined with ethyl acrylate (82.6 g, 825 mmol) and the mixture was heated under argon at 105° C. for 4 days. After removing the volatiles in vacuo the resulting yellow oil was purified by flash column chromatography (silica gel, 3:1 hexanes:EtOAc) to yield a colorless oil (28.6 g, 41:59 exo:endo determined by $^1$H NMR, 72% yield). $^1$H NMR (400 MHz, CDCl$_3$) (some partial integrals due to rotomers about carbamate and exo/endo mixture) δ 6.54-6.24 (m, 2H), 5.22-4.88 (m, 1H), 4.22-4.02 (m, 2H), 3.67 (m, 3H), 3.41-3.19 (m, 1H), 3.11-3.00 (m, 1H), 3.00-2.88 (m, 1.6H), 2.88-2.74 (m, 1H), 2.53 (tdd, J=10.9, 4.3, 2.1 Hz, 0.4H), 2.10 (tdd, J=6.8, 4.3, 2.5 Hz, 0.4H), 1.92-1.76 (m, 1.2H), 1.58-1.50 (m, 0.4H), 1.26 (m, 3H).

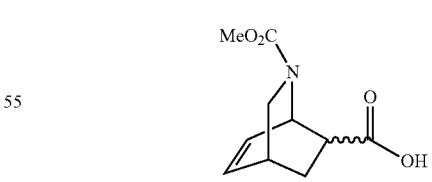

exo/endo-2-(methoxycarbonyl)-2-azabicyclo[2.2.2]oct-5-ene-7-carboxylic acid (44): 19 (28.0 g, 117 mmol) was dissolved in THF (440 mL) and H$_2$O (147 mL) under argon and the solution was cooled to 0° C. H$_2$O$_2$ (34.3 mL of 30% aq. soln., 336 mmol) and LiOH.H$_2$O (9.82 g, 234 mmol) were then added and the mixture was warmed to 40° C. and left to stir for 12 h. After this time, the reaction was cooled to room temperature and the THF was removed in vacuo.

The mixture was then diluted with H2O (100 mL) and washed with DCM (3×50 mL). The aqueous phase was then acidified with 10% HCl and extracted with DCM (4×50 mL). The combined organic extracts were washed with H$_2$O (2×50 mL), dried over Na$_2$SO$_4$, filtered, and concentrated to yield a colorless oil which slowly crystallized into a white, waxy solid (21.5 g, 87% yield). $^1$H NMR (300 MHz, CDCl$_3$) (some partial integrals due to rotomers about carbamate and exo/endo mixture, OH not observed) δ 6.56-6.27 (m, 2H), 5.25-4.91 (m, 1H), 3.79-3.60 (m, 3H), 3.37 (d, J=10.1 Hz, 0.4H), 3.26 (d, J=10.0 Hz, 0.6H), 3.13 (s, 0.6H), 2.95 (t, J=11.5 Hz, 1H), 2.84 (s, 1H), 2.59 (d, J=8.6 Hz, 0.4H), 2.07 (d, J=12.7 Hz, 0.4H), 1.94-1.78 (m, 1.2H), 1.60 (t, J=11.8 Hz, 0.4H); m/z calcd. for C$_{10}$H$_{13}$NO$_4$=211.08, found=212.23.

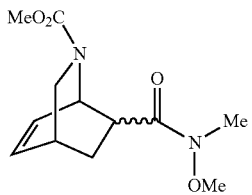 [SMILES: COC(=O)N1CC2C=CC1C(C(=O)N(C)OC)C2]

exo/endo-methyl 7-(methoxy(methyl)carbamoyl)-2-azabicyclo[2.2.2]oct-5-ene-2-carboxylate (45): 44 (15.0 g, 71.0 mmol) was dissolved in DCM (1.0 L) and cooled to 0° C. under argon. DIPEA (14.8 mL, 11.0 g, 85.2 mmol), 1-ethyl-3-(3-dimethylaminopropyl)carbodiimide hydrochloride (14.3 g, 74.6 mmol), N,O-dimethylhydroxylamine hydrochloride (8.31 g, 85.2 mmol), and DMAP (867 mg, 7.10 mmol) were then added and the mixture was stirred for 2 h at 0° C. and 2 h at room temperature before quenching with H$_2$O (700 mL). The organic layer was separated and washed with 1% NaOH (2×150 mL), 2% HCl (3×100 mL), and H$_2$O (150 mL), dried over Na$_2$SO$_4$, filtered through celite, and concentrated to yield a yellow oil (16.5 g, 41:59 exo:endo determined by $^1$H NMR, 91% yield). $^1$H NMR (300 MHz, CDCl$_3$) (some partial integrals due to rotomers about carbamate and exo/endo mixture) δ 6.52-6.32 (m, 2H), 5.10-4.77 (m, 1H), 3.77-3.58 (m, 6H), 3.44-3.23 (m, 2H), 3.20-3.10 (m, 3H), 3.05-2.86 (m, 1H), 2.86-2.71 (m, 1H), 2.25-2.10 (m, 0.4H), 2.01-1.82 (m, 0.6H), 1.79-1.58 (m, 0.6H), 1.52-1.35 (m, 0.4H); $^{13}$C NMR (126 MHz, CDCl$_3$) (very complex due to rotomers and exo/endo mixture) δ 156.3, 155.8, 135.6, 135.3, 134.2, 134.0, 132.3, 131.8, 131.1, 130.9, 61.5, 61.4, 61.2, 52.5, 52.4, 52.3, 47.6, 47.4, 47.11, 47.09, 47.06, 47.0, 46.82, 46.81, 42.4, 41.9, 41.5, 41.2, 33.1 (br), 32.9 (br), 32.5 (br), 30.9, 30.7, 30.3, 30.1, 27.9, 27.4, 24.9, 24.7; m/z calcd. for C$_{12}$H$_{18}$N$_2$O$_4$=254.13, found=255.23.

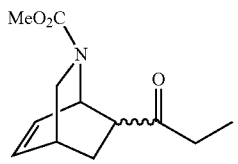 [SMILES: CCC(=O)C1CC2C=CC1N(C(=O)OC)C2]

exo/endo-methyl 7-propionyl-2-azabicyclo[2.2.2]oct-5-ene-2-carboxylate (synthesis and epimerization, 55 and 56): 45 (5.00 g, 19.7 mmol) was dissolved in dry THF (200 mL) under argon and the solution was cooled to 0° C. EtMgBr (13.1 mL of 3.0 M soln. in Et$_2$O, 39.4 mmol) was then added and the reaction was left to stir at 0° C. for 1 h. After quenching with ice-cold 5% HCl in 6:1 EtOH:H$_2$O (200 mL), the mixture was diluted with H$_2$O (400 mL) and extracted with DCM (3×100 mL). The combined organics were washed with H$_2$O (2×150 mL), dried over Na$_2$SO$_4$, and concentrated to yield a pale yellow oil (55, 4.06 g, 38:62 exo:endo determined by $^1$H NMR, 92% yield). To enrich the exo-epimer, this material was dissolved in MeOH (140 mL) under argon, sodium methoxide (5.90 g, 109.2 mmol) was added, and the mixture was stirred at room temperature for 4 h. After removing the MeOH in vacuo, the remaining aqueous was extracted with DCM (3×50 mL). The combined organics were washed with water (50 mL) and brine (50 mL), dried over Na$_2$SO$_4$, and concentrated to yield a yellow oil (56, 4.00 g, 63:37 exo:endo determined by $^1$H NMR, 99% yield). $^1$H NMR (400 MHz, CDCl$_3$) (some partial integrals due to rotomers about carbamate and exo/endo mixture) δ 6.52-6.42 (m, 1.2H), 6.39 (t, J=7.4 Hz, 0.4H), 6.31-6.25 (m, 0.4H), 5.17-4.80 (m, 1H), 3.66 (m, 3H), 3.35-3.23 (m, 1H), 3.17-3.05 (m, 0.4H), 3.03-2.87 (m, 1H), 2.87-2.72 (m, 1H), 2.72-2.61 (m, 1H), 2.52-2.35 (m, 1.4H), 2.25-2.12 (m, 0.6H), 1.91-1.57 (m, 1H), 1.44-1.27 (m, 0.6H), 1.05 (m, 3H); m/z calcd. for C$_{12}$H$_{17}$NO$_3$=223.12, found=224.00.

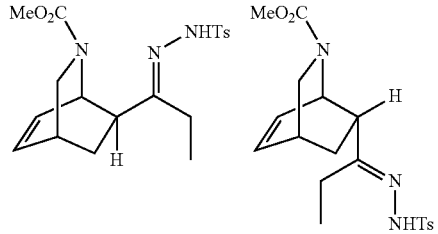

exo-methyl 7-(1-(2-tosylhydrazono)propyl)-2-azabicyclo[2.2.2]oct-5-ene-2-carboxylate (57a) and endo-methyl 7-(1-(2-tosylhydrazono)propyl)-2-azabicyclo[2.2.2]oct-5-ene-2-carboxylate (57b) (synthesis and separation): 56 (4.00 g, 17.9 mmol) and tosylhydrazine (3.33 g, 17.9 mmol) were combined in dry THF (15 mL) under argon and the mixture was stirred at 50° C. for 14 h. After removing the volatiles in vacuo, the resulting off-white solid was purified by repeated flash column chromatography (silica gel, gradients of Et$_2$O in DCM) to yield the pure exo (57a, 1.69 g, 24% yield) and endo (57b, 1.17 g, 17% yield) epimers along with several mixed exo/endo fractions (2.65 g, 38% yield).

57a. The exo-tosylhydrazone was prepared by separation of the exo/endo mixture as described above. White solid. $^1$H NMR (400 MHz, CDCl$_3$) (spectrum complicated by rotomers) δ 7.84 and 7.78 (d, J=8.3 Hz, 2H), 7.37 (br s, 1H), 7.32 (t, J=7.3 Hz, 2H), 6.47-6.36 (m, 2H), 4.67 and 4.55 (m, 1H), 3.49 and 3.36 (s, 3H), 3.09 and 2.99 (dd, J=9.8, 2.1 Hz and J=9.9, 1.9 Hz, 1H), 2.88 and 2.80 (dt, J=10.1, 2.4 Hz and J=9.8, 2.6 Hz, 1H), 2.70 (dd, J=5.1, 2.6 Hz, 1H), 2.51 and 2.45 (ddd, J=10.6, 4.4, 1.7 Hz, 1H), 2.44 (s, 3H), 2.39-2.04 (m, 3H), 1.40-1.24 (m, 1H), 1.11-0.99 (m, 3H); m/z calcd. for C$_{19}$H$_{25}$N$_3$O$_4$S=391.16, found=391.90.

57b. The endo-tosylhydrazone was prepared by separation of the exo/endo mixture as described above. White solid. $^1$H NMR (400 MHz, CDCl$_3$) (spectrum complicated by rotomers) δ 7.79 (t, J=7.2 Hz, 2H), 7.52 (br t, J=16.9 Hz, 1H), 7.30 (d, J=8.1 Hz, 2H), 6.22-6.10 (m, 1H), 6.05-5.92 (m, 1H), 4.83 and 4.72 (d, J=4.1 Hz and 4.3 Hz, 1H), 3.68 and 3.65 (s, 3H), 3.32-3.18 (m, 1H), 3.01-2.86 (m, 2H), 2.73

(br s, 1H), 2.44 and 2.43 (s, 3H), 2.23-1.96 (m, 2H), 1.83-1.62 and 1.55-1.47 (m, 2H), 1.04-0.97 (m, 3H); m/z calcd. for $C_{19}H_{25}N_3O_4S$=391.16, found=391.90.

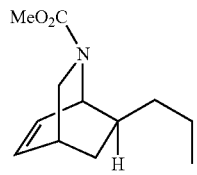

exo-methyl 7-propyl-2-azabicyclo[2.2.2]oct-5-ene-2-carboxylate (58a): 57a (1.64 g, 4.19 mmol), sodium cyanoborohydride (1.05 g, 16.8 mmol), and p-toluenesulfonic acid monohydrate (67.0 mg, 0.352 mmol) were combined in dry THF (17 mL) under argon and the mixture was refluxed for 13 h. At this time an additional portion of p-TsOH.H$_2$O (17 mg, 0.088 mmol) was added and reflux was continued for an additional 5 h. After cooling to room temperature, the reaction mixture was extracted with cyclohexane (3×20 mL). The combined organics were washed with H$_2$O (20 mL), sat. aq. NaHCO$_3$ (20 mL), and H$_2$O again (20 mL), dried over Na$_2$SO$_4$, and concentrated to yield a cloudy yellow oil. This was purified by flash column chromatography (silica gel, 7:1 hexanes:EtOAc) to yield a thin, pale-yellow oil (460 mg, 52% yield). $^1$H NMR (400 MHz, CDCl$_3$) (spectrum complicated by rotamers) δ 6.53-6.38 (m, 1H), 6.38-6.25 (m, 1H), 4.56 and 4.41 (d, J=6.1 Hz, 1H), 3.69 and 3.67 (s, 3H), 3.21 (td, J=10.0, 2.2 Hz, 1H), 2.97 (ddt, J=18.6, 10.0, 2.6 Hz, 1H), 2.72-2.59 (br m, 1H), 1.67-1.49 (m, 2H), 1.47-1.24 (m, 4H), 1.00 (dd, J=11.2, 2.8 Hz, 1H), 0.92-0.86 (m, 3H); $^{13}$C NMR (101 MHz, CDCl$_3$) δ 156.2 and 155.8 (1C), 133.4 and 133.3 (1C), 132.9 and 132.8 (1C), 51.7, 49.2 and 48.8 (1C), 48.1 and 47.8 (1C), 38.1, 36.6 and 36.5 (1C), 30.5 and 30.3 (1C), 29.7 and 29.6 (1C), 20.3 and 20.2 (1C), 13.8; m/z calcd. for $C_{12}H_{19}NO_2$=209.14, found=210.07.

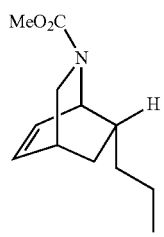

endo-methyl 7-propyl-2-azabicyclo[2.2.2]oct-5-ene-2-carboxylate (58b): Sodium cyanoborohydride (264 mg, 4.20 mmol) and ZnCl$_2$ (286 mg, 2.10 mmol) were dissolved in MeOH and this solution was added to a solution of 57b in MeOH (13 mL) under argon. After refluxing for 3.5 h the reaction was quenched with 1.0% aq. NaOH (70 mL) and extracted with cyclohexane (3×50 mL). The combined organics were washed with H$_2$O (50 mL) and brine (50 mL), dried over Na$_2$SO$_4$, and concentrated to yield a pale-yellow cloudy oil. This was purified by flash column chromatography (silica gel, 6:1 hexanes:EtOAc) to yield a thin yellow oil (372 mg, 60% yield). $^1$H NMR (400 MHz, CDCl$_3$) (spectrum complicated by rotamers) δ 6.38 (dd, J=14.3, 6.9 Hz, 1H), 6.34-6.22 (m, 1H), 4.65-4.61 and 4.48-4.43 (br m, 1H), 3.69 and 3.66 (s, 3H), 3.24-3.16 (m, 1H), 2.94 (ddt, J=19.6, 10.1, 2.5 Hz, 1H), 2.69 (br s, 1H), 2.13-1.98 (m, 1H), 1.85-1.76 (m, 1H), 1.35-1.23 (m, 2H), 1.23-1.10 (m, 1H), 0.99-0.82 (m, 5H); $^{13}$C NMR (101 MHz, CDCl$_3$) δ 155.5 and 155.1 (1C), 134.4 and 134.0 (1C), 130.6 and 130.0 (1C), 52.0 and 51.9 (1C), 49.5 and 49.0 (1C), 46.9 and 46.5 (1C), 38.6 and 38.3 (1C), 37.7, 31.1 and 30.8 (1C), 30.2, 19.72 and 19.66 (1C), 13.9; m/z calcd. for $C_{12}H_{19}NO_2$=209.14, found=210.02.

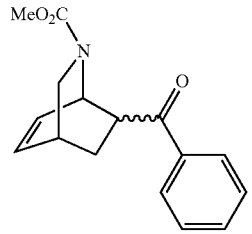 [SMILES: COC(=O)N1CC2C=CC1C(C(=O)c1ccccc1)C2]

exo/endo-methyl 7-benzoyl-2-azabicyclo[2.2.2]oct-5-ene-2-carboxylate (46): 45 (2.00 g, 7.87 mmol) was dissolved in dry THF (80 mL) under argon and PhMgBr (15.7 mL of 3.0 M soln. in Et$_2$O, 47.2 mmol) was added at room temperature. After stirring for 15 min the reaction was quenched with ice-cold 5% HCl in 6:1 EtOH:H$_2$O (160 mL), diluted with H$_2$O (250 mL), and extracted with DCM (3×80 mL). The combined organics were washed with H$_2$O (2×100 mL), dried over Na$_2$SO$_4$, and concentrated to yield a yellow oil. This was purified by flash column chromatography (silica gel, 7:3 hexanes:EtOAc) to yield an off-white waxy solid (1.91 g, 40:60 exo:endo determined by $^1$H NMR, 89% yield). $^1$H NMR (400 MHz, CDCl$_3$) (spectrum complicated by rotamers) δ 8.02-7.85 (m, 2H), 7.61-7.51 (m, 1H), 7.51-7.41 (m, 2H), 6.60-6.24 (m, 2H), 5.20 and 5.03 (br s, 0.6H), 4.97 and 4.82 (d, J=6.0 Hz, 0.4H), 4.04-3.90 (m, 0.6H), 3.74, 3.73, 3.60, and 3.37 (s, 3H), 3.65-3.54 (m, 0.4H), 3.49-3.34 (m, 1H), 3.09-2.93 (m, 1H), 2.88 (br s, 1H), 2.28 (dd, J=23.0, 12.0 Hz, 0.4H), 2.10-1.75 (m, 1.2H), 1.61-1.49 (m, 0.4H); m/z calcd. for $C_{16}H_{17}NO_3$=271.12, found=272.26.

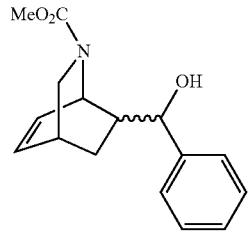 [SMILES: COC(=O)N1CC2C=CC1C(C(O)c1ccccc1)C2]

exo/endo-methyl 7-(hydroxy(phenyl)methyl)-2-azabicyclo[2.2.2]oct-5-ene-2-carboxylate (50): 46 (1.67 g, 6.16 mmol) was dissolved in MeOH (50 mL) under argon and the solution was chilled to 0° C. NaBH$_4$ (233 mg, 6.16 mmol) was then added and the solution was warmed to room temperature and stirred for 30 min. The volatiles were removed in vacuo to yield a white solid which was partitioned between DCM (25 mL) and H$_2$O (25 mL). After separating the organic layer, the aqueous was extracted with additional DCM (25 mL). The combined organics were washed with H$_2$O (25 mL) and sat. aq. NH$_4$Cl (2×25 mL), dried over Na$_2$SO$_4$, and concentrated to yield a white solid (1.63 g, 97% yield). $^1$H NMR (400 MHz, CDCl$_3$) (Due to the presence of 4 diastereomers and rotamers about the carbamate, the $^1$H NMR spectrum is significantly complicated.) δ 7.42-7.23 (m, 5H), 6.56-6.20 (m, 2H), 5.25-4.92 (m, 0.74H), 4.34-4.01 (m, 0.76H), 3.95 (dd, J=10.4, 3.9 Hz, 0.41H), 3.86 (d, J=3.2 Hz, 0.23H), 3.77, 3.73, 3.68, 3.61, and 3.55 (s, 3H), 3.35-3.15 (m, 1H), 3.08-2.88 (m, 1H), 2.83 (br s, 0.24H), 2.65 (br s, 0.74H), 2.61-2.45 (m, 0.64H), 2.43 (br s, 0.09H), 2.06-1.96 (m, 0.38H), 1.96-1.66 (m, 1H), 1.56 (br s, 0.25H), 1.45-1.34 (m, 0.45H), 1.22 (t, J=12.1 Hz, 0.41H), 0.99-0.86 (m, 0.36H), 0.82-0.70 (m, 0.44H); m/z calcd. for $C_{16}H_{19}NO_3$=273.14, found=274.06.

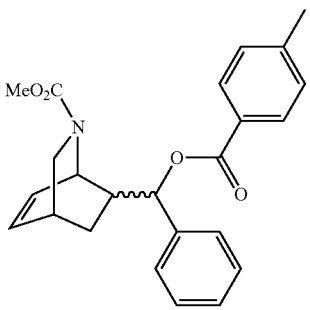 [SMILES: COC(=O)N1CC2C=CC1C(C(OC(=O)c1ccc(C)cc1)c1ccccc1)C2]

exo/endo-methyl 7-(((4-methylbenzoyl)oxy) (phenyl)methyl)-2-azabicyclo[2.2.2]oct-5-ene-2-carboxylate (53): 50 (480 mg, 1.76 mmol) was dissolved in dry DCM (22 mL) under argon and the solution was cooled to 0° C. Tetramethylethylenediamine (0.58 mL, 450 mg, 3.87 mmol) and p-toluoyl chloride (0.51 mL, 598 mg, 3.87 mmol) were then added and the mixture was warmed to room temperature and stirred for 30 min. After quenching with sat. aq. NaHCO$_3$ (20 mL), the organic layer was separated and the remaining aqueous was extracted with additional DCM (2×20 mL). The combined organics were washed with sat. aq. NaHCO$_3$ (20 mL) and brine (20 mL), dried over Na$_2$SO$_4$, and concentrated to yield and off-white oil. This was purified by flash column chromatography (silica gel, 3:1 hexanes:EtOAc) to yield a white solid (567 mg, 82% yield). $^1$H NMR (400 MHz, CDCl$_3$) (Due to the presence of 4 diastereomers and rotamers about the carbamate, the $^1$H NMR spectrum is significantly complicated.) δ 8.03-7.87 (m, 2H), 7.51-7.18 (m, 7H), 6.60-6.22 (m, 2H), 5.83 (t, J=11.3 Hz, 0.02H), 5.70-5.58 (m 0.30H), 5.44 (d, J=10.0 Hz, 0.20H), 5.36-5.29 (m, 0.40H), 5.14-5.03 (m, 0.32H), 4.94-4.86 (m, 0.37H), 4.34 (br s, 0.09H), 4.15 (br s, 0.11H), 3.73, 3.71, 3.66, 3.63, 3.61, 3.58 and 3.34 (s, 3H), 3.40-3.33 (m, 0.43H), 3.33-3.19 (m, 0.68H), 3.08-2.78 (m, 1.87H), 2.72 (s, 0.78H), 2.42 and 2.40 (s, 3H), 2.34 (dd, J=11.0, 5.0 Hz, 0.30H), 1.94 (t, J=11.1 Hz, 0.20H), 1.79 (br s, 0.05H), 1.70 (br s, 0.21H), 1.58-1.37 (m, 0.70H), 1.37-1.23 (m, 0.36H), 1.15-1.01 (m, 0.33H), 0.99-0.89 (m, 0.50H); m/z calcd. for $C_{24}H_{25}NO_4$=391.18, found=392.20.

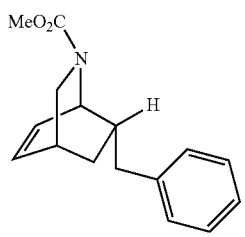 [SMILES: COC(=O)N1CC2C=CC1C(Cc1ccccc1)C2]

endo-methyl 7-benzyl-2-azabicyclo[2.2.2]oct-5-ene-2-carboxylate (54): SmI$_2$ solution (16.6 mL of 0.1 M in THF, 1.66 mmol) was brought to reflux under argon. HMPA (1.15 mL, 1.19 g, 6.62 mmol) was then added followed by a solution of 53 (108 mg, 0.276 mmol) in dry THF (2.4 mL, freshly distilled from Na/benzophenone ketyl) and the dark purple mixture was refluxed for 5 min. After removing from heat the reaction was immediately quenched with sat. aq. NH$_4$Cl (20 mL) and the resulting mixture was extracted with DCM (3×20 mL). The combined organics were washed with brine (2×20 mL), dried over Na$_2$SO$_4$, and concentrated to yield a cloudy white oil. This was purified by flash column chromatography (8:2 hexanes:EtOAc) to yield a clear colorless oil (29 mg, 41% yield, pure endo epimer). The corresponding exo epimer is unstable under the reaction conditions and was not recovered from the reaction mixture. $^1$H NMR (400 MHz, CDCl$_3$) (spectrum complicated by rotomers) δ 7.32-7.09 (m, 5H), 6.51-6.29 (m, 2H), 4.63 and 4.41 (d, J=5.4 and J=5.3 Hz, 1H), 3.65 and 3.64 (s, 3H), 3.20 (dd, J=15.7, 5.6 Hz, 1H), 2.94 (ddd, J=12.0, 10.1, 6.4 Hz, 1H), 2.72 (br s, 1H), 2.57-2.41 (m, 2H), 2.37-2.22 (m, 1H), 1.83-1.69 (m, 1H), 1.02 (ddd, J=12.8, 7.1, 3.0 Hz, 1H); $^{13}$C NMR (101 MHz, CDCl$_3$) δ 155.9 and 155.6 (1C), 139.8 and 139.7 (1C), 135.0 and 134.6 (1C), 130.9 and 130.3 and 130.2 (1C), 129.0 and 128.9 (2C), 128.5 (2C), 126.2, 52.4 and 52.3 (1C), 49.4 and 49.1 (1C), 47.2 and 46.9 (1C), 41.7, 40.3 and 40.2 (1C), 31.3 and 31.1 (1C), 30.0 and 29.9 (1C); m/z calcd. for $C_{16}H_{19}NO_2$=257.14, found=258.28.

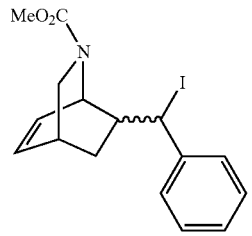 [SMILES: COC(=O)N1CC2C=CC1C(C(I)c1ccccc1)C2]

exo/endo-methyl 7-(iodo(phenyl)methyl)-2-azabicyclo[2.2.2]oct-5-ene-2-carboxylate (51): 50 (137 mg, 0.50 mmol) was dissolved in dry toluene (2.3 mL) and dry CH$_3$CN (1.1 mL) and the solution was cooled to 0° C. Triphenylphosphine (386 mg, 1.47 mmol), imidazole (202 mg, 2.96 mmol), and iodine (386 mg, 1.52 mmol) were then added and the mixture was allowed to warm to room temperature and stirred for 1 h. At this time the reaction was quenched with H$_2$O (5 mL) and extracted with DCM (3×5 mL). The combined organics were washed with sat. aq. Na$_2$S$_2$O$_3$ (5 mL) and brine (5 mL), dried over Na$_2$SO$_4$, and concentrated to yield an off-white solid. This was purified by flash column chromatography (silica gel, 6:4 hexanes:Et$_2$O) to yield a pale-yellow oil (151 mg, 79% yield). $^1$H NMR (400 MHz, CDCl$_3$) (Due to the presence of 4 diastereomers and rotomers about the carbamate, the NMR spectrum is significantly complicated.) δ 7.48-7.12 (m, 5H), 6.65-5.97 (m, 2H), 5.42-5.07 (m, 0.19H), 5.03-4.85 (m, 0.40H), 4.52-4.34 (m, 0.69H), 4.29-4.10 (m, 0.44H), 3.78, 3.74, 3.72, 3.68, 3.63, 3.59, and 3.41 (s, 3H), 3.36-3.05 (m, 1.41H), 3.04-2.67 (m, 2H), 2.64-2.41 (m, 0.61H), 2.04 (br s, 0.36H), 1.93 (br s, 0.36H), 1.77-1.57 (m, 0.27H), 1.50 (br d, J=11.5 Hz, 0.36H), 1.45-1.34 (m, 0.11H), 1.33-1.21 (m, 0.66H), 1.15 (br s, 0.04H), 0.97 (br d, J=6.6 Hz, 0.04H), 0.89 (br s, 0.13H), 0.80 (br d, J=9.3 Hz, 0.20H); m/z calcd. for $C_{16}H_{18}INO_2$=383.04, found=384.17.

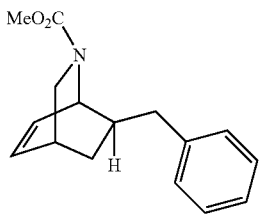 [SMILES: COC(=O)N1CC2C=CC1C(Cc1ccccc1)C2]

endo-methyl 7-benzyl-2-azabicyclo[2.2.2]oct-5-ene-2-carboxylate (48): 51 (474 mg, 1.24 mmol) and an excess of NaBH$_4$ (938 mg, 24.8 mmol) were dissolved in dry DMPU (12 mL, freshly distilled from CaH$_2$) under argon and stirred for 15 h at room temp. The reaction was quenched with H$_2$O (100 mL) and extracted with Et$_2$O (3×40 mL). The combined organics were washed with H$_2$O (3×25 mL) and brine (25 mL), dried over Na$_2$SO$_4$, and concentrated to yield a clear colorless oil (319 mg, mixture of exo/endo epimers, 9.5:1 reduction:elimination). The exo epimer was separated from this mixture by flash column chromatography (32 g silica gel, 8% to 14% EtOAc in hexanes in 1% steps, 32 mL for each step, 16 mL fractions) to yield a nearly colorless oil (87 mg, 88:12 exo:endo, 27% yield). The endo epimer could not be separated from a close eluting impurity of the styrene elimination product. $^1$H NMR (400 MHz, CDCl$_3$) (spectrum complicated by rotomers, peaks for endo epimer impurity not listed δ 7.32-7.10 (m, 5H), 6.48-6.27 (m, 2H), 4.58 and 4.35 (d, J=6.1 Hz and J=5.8 Hz, 1H), 3.73 and 3.70 (s, 3H), 3.30 (ddd, J=9.7, 7.7, 2.1 Hz, 1H), 3.03 (ddt, J=19.1, 9.9, 2.6 Hz, 1H), 2.79-2.55 (m, 3H), 1.97-1.83 (m, 1H), 1.67-1.57 (m, 1H), 1.17-1.07 (m, 1H); $^{13}$C NMR (126 MHz, CDCl$_3$) δ 157.0 and 156.6 (1C), 140.8 and 140.7 (1C), 133.90 and 133.86 (1C), 133.34 and 133.29 (1C), 129.3 and 129.2 (2C), 128.4 and 128.3 (2C), 126.1 and 126.0 (1C), 52.5 and 52.3 (1C), 49.3 and 49.1 (1C), 48.72 and 48.68 (1C), 41.1 and 40.8 (1C), 40.5, 31.0 and 30.8 (1C), 29.8 and 29.7 (1C); m/z calcd. for C$_{16}$H$_{19}$NO$_2$=257.14, found=258.24.

Figure 15:
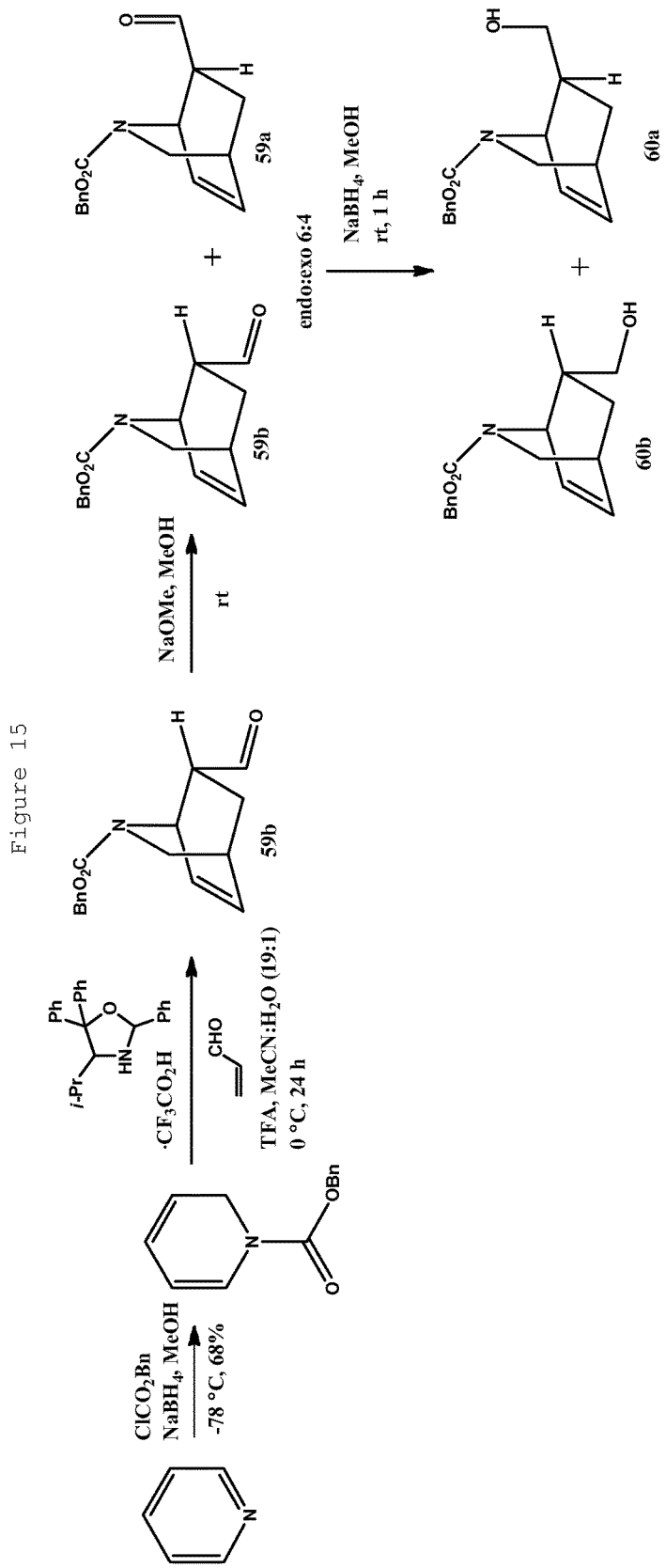
FIG. 15. Synthesis of 7-hydroxymethyl isoquinuclidine intermediates.
Figure 16:
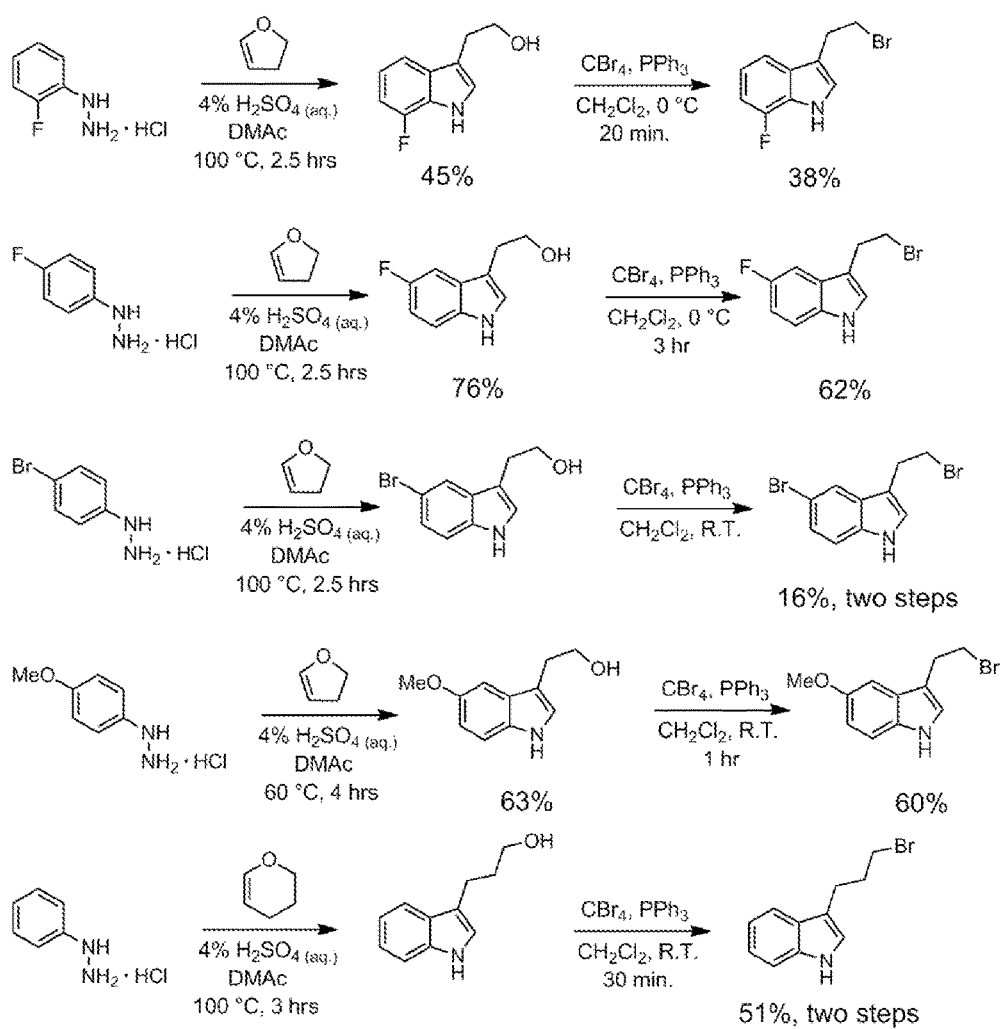
FIG. 16. Synthesis of 3-(2-bromoethyl)indoles and 3-(3-bromopropyl)indoles.
Figure 17:
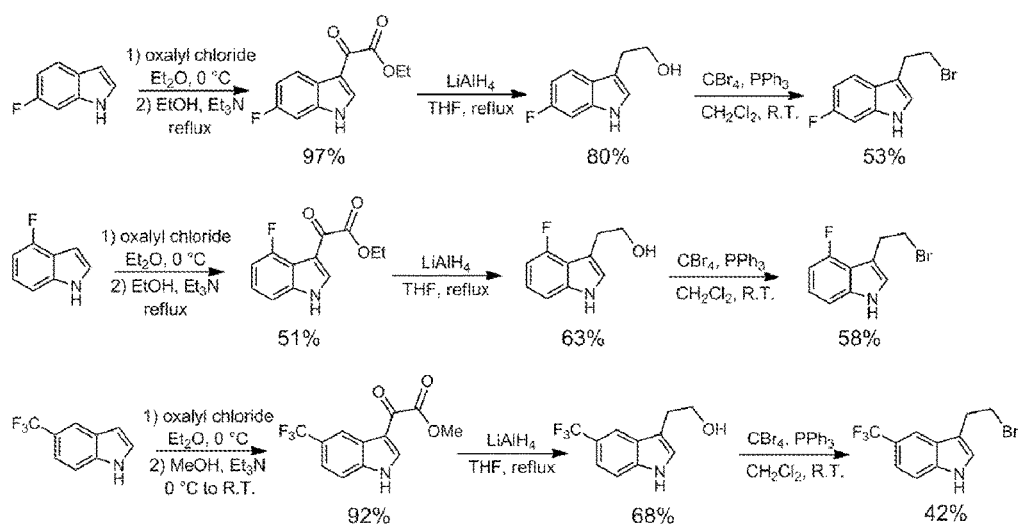
FIG. 17. Synthesis of 3-(2-bromoethyl)indoles.
Figure 18:
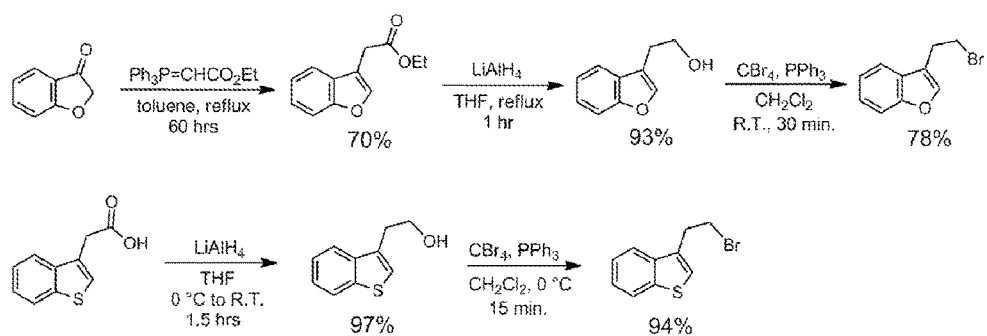
FIG. 18. Synthesis of 3-(2-bromoethyl)benzofurans and 3-(2-bromoethyl)benzothiophenes.
Figure 19:
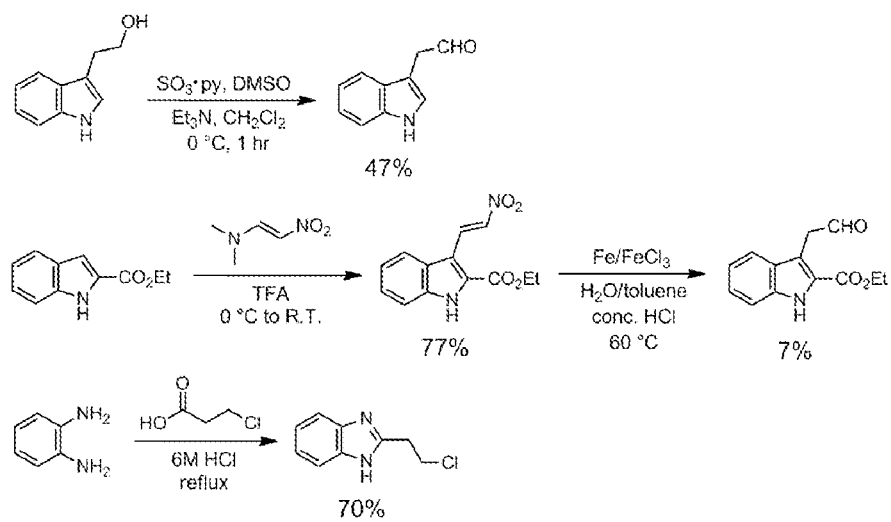
FIG. 19. Synthesis of various heteroaryl fragments.

Key intermediates 60a and 60b were synthesized according to the organocatalytic method depicted in the scheme in FIG. 15. An organocatalytic Diels-Alder reaction followed by the epimerization produced aldehydes 59a and 59b followed by reduction to intermediate alcohols 60a and 60b (Nakano, H. et al. 2010).

Preparation of exo- and endo-benzyl 7-(hydroxymethyl)-2-azabicyclo[2.2.2]oct-5-ene-2-carboxylate: To a CH$_3$CN (50 mL) solution of organocatalyst (273 mg, 0.6 mmol), cold water (0.5 mL), trifluoroacetic acid (0.14 mL, 1.8 mmol), and distilled acrolein (0.42 mL, 6.0 mmol) were added at 0° C. and the solution was stirred. After 1 min, N-(benzyloxycarbonyl)-1,2-dihydropyridine (1.42 g, 6.6 mmol) was added and the solution was stirred at 0° C. for 24 h. The reaction was quenched with water (30 mL) and extracted with Et$_2$O (30 mL×3). The combined organic extracts were washed with brine (30 mL), dried over Na$_2$SO$_4$, and concentrated under reduced pressure to give the crude endo-DA adduct (59b, 1.82 g), which was used in the next reaction without purification.

To a stirred solution of crude 59b (1.82 g) in MeOH (10 mL), NaOMe (1.0 g) was added and the mixture was stirred at room temperature for 12 hr. The reaction was quenched with water (30 mL) and extracted with EtOAc (30 mL×3). The combined organic extracts were washed with brine (20 mL), dried over Na$_2$SO$_4$, and concentrated under reduced pressure to give the crude endo/exo mixture (endo:exo=6:4) of DA adduct (1.71 g), which was used in the next reaction without purification.

To a stirred solution of the crude endo/exo-DA adduct (1.71 g) in ethanol (5.0 mL), NaBH$_4$ (122 mg, 3.0 mmol) was added and the mixture was stirred at room temperature for 1 h. The solvent was evaporated under reduced pressure and the reaction mixture was diluted with water (10 mL) and extracted with EtOAc (30 mL×3). The combined organic extracts were washed with brine (10 mL), dried over Na$_2$SO$_4$, and concentrated under reduced pressure. The epimers were separated by flash column chromatography (silica gel, hexanes:EtOAc=7:3) to give 31% endo-60b and 27% exo-60a product over three steps.

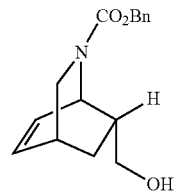 [SMILES: O=C(OCc1ccccc1)N1CC2C=CC1C(CO)C2]

endo-benzyl 7-(hydroxymethyl)-2-azabicyclo[2.2.2]oct-5-ene-2-carboxylate (60b): Prepared and separated as described above. Purified by flash column chromatography (silica gel, hexanes:EtOAc=7:3). Colorless oil, 31% yield. $^1$H NMR (400 MHz, CDCl$_3$) (spectrum complicated by rotomers) δ 7.35-7.27 (m, 5H), 6.42-6.28 (m, 2H), 5.19-5.09 (m, 2H), 4.90-4.83 (m, 1H), 3.30-3.24 (m, 2H), 3.20-3.14 (m, 1H), 3.03-2.99 (m, 1H), 2.74 (br s, 1H), 2.45-2.31 (m, 1H), 1.84-1.74 (m, 1H), 0.92-0.81 (m, 1H) [OH not seen]; $^{13}$C NMR (100 MHz, CDCl$_3$) δ 155.2 and 154.8 (1C), 136.9 and 136.8 (1C), 134.9 and 134.6 (1C), 130.4 and 130.0 (1C), 128.4, 127.8, 127.6, 66.7, 65.5 and 65.4 (1C), 47.3 and 47.2 (1C), 46.9 and 46.8 (1C), 41.5, 30.8 and 30.5 (1C), 26.1; m/z calcd. for C$_{16}$H$_{19}$NO$_3$=273.13, found=274.20.

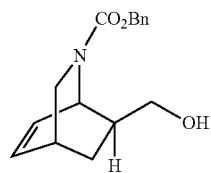 [SMILES: O=C(OCc1ccccc1)N1CC2C=CC1C(CO)C2]

exo-benzyl 7-(hydroxymethyl)-2-azabicyclo[2.2.2]oct-5-ene-2-carboxylate (60a): Prepared and separated as described above. Purified by flash column chromatography (silica gel, hexanes:EtOAc=7:3). Colorless oil, 27% yield. $^1$H NMR (400 MHz, CDCl$_3$) (spectrum complicated by rotomers) δ 7.38-7.30 (m, 5H), 6.47-6.42 (m, 2H), 5.22-5.07 (m, 2H), 4.87-4.68 (m, 1H), 3.69-3.57 (m, 1H), 3.27-3.17 (m, 2H), 3.04-3.00 (m, 1H), 2.72-2.65 (m, 1H), 1.95-1.79 (m, 1H), 1.57-1.49 (m, 1H), 0.92-0.80 (m, 1H) [OH not seen]; $^{13}$C NMR (100 MHz, CDCl$_3$) δ 156.9, 136.7, 135.0 and 134.7 (1C), 132.2 and 132.1 (1C), 128.6 and 128.5 (1C), 127.9, 127.7, 67.1, 64.9 and 64.7 (1C), 48.5 and 48.3 (1C), 46.6 and 46.1 (1C), 41.2 and 40.8 (1C), 30.4 and 30.2 (1C), 25.7; m/z calcd. for C$_{16}$H$_{19}$NO$_3$=273.13, found=274.28.

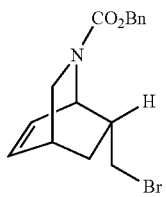 [SMILES: O=C(OCc1ccccc1)N1CC2C=CC1C(CBr)C2]

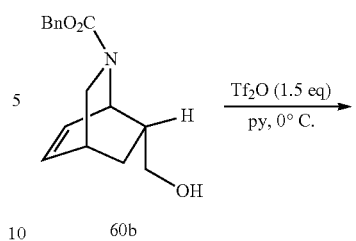

endo-benzyl 7-(bromomethyl)-2-azabicyclo[2.2.2]oct-5-ene-2-carboxylate (61b): To a stirred solution of 60b (3.25 g, 12.0 mmol) in dry DCM (30 mL), carbon tetrabromide (4.78 g, 14.4 mmol) and triphenylphosphine (3.78 g, 14.4 mmol) were added in three portions at 0° C. and the mixture was stirred for 16 h at room temperature. The reaction mixture was then concentrated under reduced pressure and purified by flash column chromatography (silica gel, hexanes:EtOAc=8:2) to afford the pure product (2.93 g, 8.73 mmol) in 73% yield. Colorless oil; $^1$H NMR (400 MHz, CDCl$_3$) (spectrum complicated by rotamers) δ 7.40-7.28 (m, 5H), 6.50-6.44 (m, 1H), 6.37-6.29 (m, 1H), 5.22-5.12 (m, 2H), 4.95-4.92 (m, 1H), 3.29 (d, J=10.0 Hz, 1H), 3.12-2.95 (m, 3H), 2.78 (br s, 1H), 2.62-2.48 (m, 1H), 1.92 (dtd, J=11.8, 9.2, 2.3 Hz, 1H), 0.99 (ddd, J=15.6, 7.1, 3.5 Hz, 1H); $^{13}$C NMR (100 MHz, CDCl$_3$) δ 155.1 and 154.6 (1C), 136.9, 135.8 and 135.3 (1C), 129.9 and 129.3 (1C), 128.4, 127.9 and 127.8 (1C), 127.6, 66.8, 48.5 and 48.3 (1C), 46.8 and 46.5 (1C), 41.7 and 41.5 (1C), 36.0 and 35.9 (1C), 31.2 and 31.0 (1C), 30.0; m/z calcd. for $C_{16}H_{18}BrNO_2$=335.05 and 337.05, found=335.77 and 337.77.

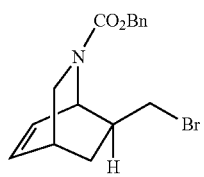 [SMILES: O=C(OCc1ccccc1)N1CC2C=CC1C(CBr)C2]

exo-benzyl 7-(bromomethyl)-2-azabicyclo[2.2.2]oct-5-ene-2-carboxylate (61a): To a stirred solution of 60a (3.25 g, 12.0 mmol) in dry DCM (30 mL), carbon tetrabromide (4.78 g, 14.4 mmol) and triphenylphosphine (3.78 g, 14.4 mmol) were added in three portions at 0° C. and the mixture was stirred for 16 h at room temperature. The reaction mixture was then concentrated under reduced pressure and purified by flash column chromatography (silica gel, hexanes:EtOAc=9:1) to afford the pure product (2.70 g, 8.03 mmol) in 67% yield. Colorless oil; $^1$H NMR (400 MHz, CDCl$_3$) (spectrum complicated by rotamers) δ 7.42-7.29 (m, 5H), 6.50-6.35 (m, 2H), 5.19-5.09 (m, 2H), 4.81 (dd, J=7.5, 6.4 Hz, 1H), 3.46-3.23 (m, 3H), 3.07-3.00 (m, 1H), 2.79-2.69 (m, 1H), 2.10-1.95 (m, 1H), 1.77-1.71 (m, 1H), 1.12 (dddd, J=26.8, 13.1, 4.7, 2.0 Hz, 1H); $^{13}$C NMR (100 MHz, CDCl$_3$) δ 156.1 and 155.8 (1C), 136.9 and 136.7 (1C), 134.2 and 133.9 (1C), 133.1 and 132.6 (1C), 128.4, 127.94 and 127.9 (1C), 127.7, 67.0 and 66.9 (1C), 48.7 and 48.6 (1C), 48.4 and 48.2 (1C), 42.0, 36.4 and 35.9 (1C), 30.7 and 30.6 (1C), 29.5; m/z calcd. for $C_{16}H_{18}BrNO_2$=335.05 and 337.05, found=335.81 and 337.81.

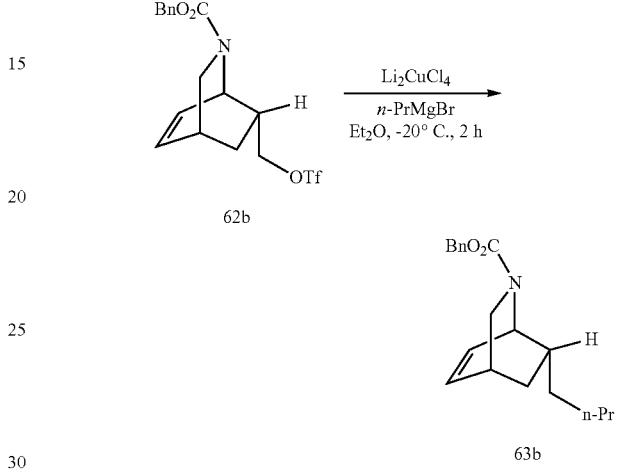

endo-benzyl 7-butyl-2-azabicyclo[2.2.2]oct-5-ene-2-carboxylate (63b): A solution of trifluoromethanesulfonic anhydride (1M in DCM) (5.0 mL, 5.0 mmol) in DCM (10 mL) was added dropwise to a solution of 60b (920 mg, 3.4 mmol) and pyridine (3.0 mL) in DCM (20 mL) with stirring at 0° C. over a period of 10 min, and the reaction mixture was then further stirred at 0° C. for 2 h. The mixture was diluted with DCM (30 mL), washed with 10% HCl and 5% aq. NaHCO$_3$, and dried (Na$_2$SO$_4$). The solvent was removed under reduced pressure to afford essentially pure triflate product (1.32 g) as a colorless oil which was used for the next step without further purification.

To freshly prepared crude triflate (162 mg, 0.40 mmol) and Li$_2$CuCl$_4$ (0.12 mL; 0.012 mmol, 0.1 M in THF) solution in anhydrous Et$_2$O (2 mL) was added "PrMgCl (0.60 mL, 1.2 mmol, 2.0 M in THF) at −20° C. and the reaction mixture was stirred for 6 hr. The reaction was quenched with H$_2$O (2 mL), warmed to room temperature, and then acidified with 2N HCl (5 mL). The organic layer was separated, and the aqueous layer was extracted with DCM (10 mL×3). The combined organic layers were washed with water and brine, dried (Na$_2$SO$_4$), and concentrated to afford the crude product which was purified by flash column chromatography (silica gel, hexanes:EtOAc=9:1) to afford the pure product (95 mg, 0.31 mmol) in 79% yield for 2 steps. Colorless oil; $^1$H NMR (400 MHz, CDCl$_3$) (spectrum complicated by rotamers) δ 7.43-7.27 (m, 5H), 6.43-6.23 (m, 2H), 5.19-5.09 (m, 2H), 4.69-4.53 (m, 1H), 3.25 (dd, J=10.2, 2.1 Hz, 1H), 2.99 (dt, J=10.1, 2.6 Hz, 1H), 2.70 (d, J=14.4 Hz, 1H), 2.07-2.05 (br m, 1H), 1.87-1.77 (m, 1H), 1.30-1.12 (m, 5H), 0.99-0.84 (m, 5H); m/z calcd. for $C_{19}H_{25}NO_2$=299.19, found=299.90.

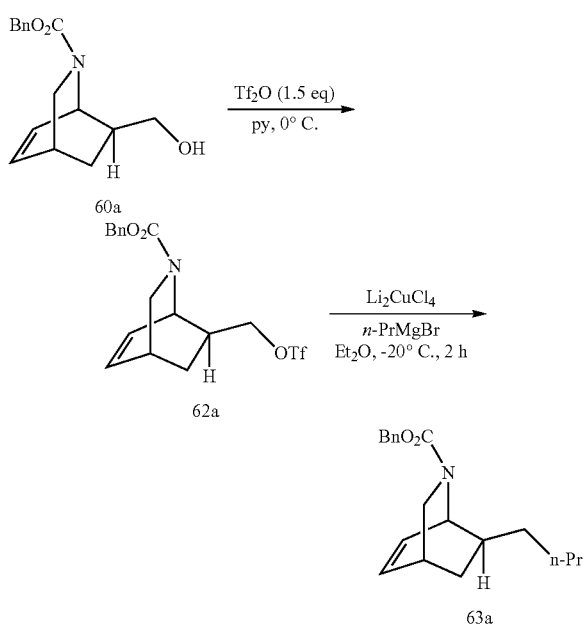

exo-benzyl 7-benzyl-2-azabicyclo[2.2.2]oct-5-ene-2-carboxylate (64a): To a mixture of 61a (200 mg, 0.60 mmol) and anhydrous FeCl$_3$ (5.0 mg, 5.0 mol %) in anhydrous THF (2 mL) at −78° C. was added a mixture of PhMgBr (0.80 mL of a 3.0 M THF solution, 2.4 mmol) and TMEDA (0.11 mL, 0.78 mmol) in THF (2 mL) via syringe pump at a rate which maintains the reaction mixture as a pale yellow solution. After completion of the addition of PhMgBr/TMEDA, the reaction mixture was stirred at room temperature for 8 hr. The reaction mixture was quenched with a saturated solution of NH$_4$Cl (2 mL) and extracted with Et$_2$O (3×4 mL). The combined organic extracts were dried over Na$_2$SO$_4$ and concentrated to afford the crude product which was purified by flash column chromatography (silica gel, hexanes:EtOAc=9:1) to afford the pure product (105 mg, 0.31 mmol) in 52% yield. Colorless oil; $^1$H NMR (400 MHz, CDCl$_3$) (spectrum complicated by rotomers) δ 7.37-7.08 (m, 10H), 6.48-6.27 (m, 2H), 5.21-5.08 (m, 2H), 4.60-4.44 (br m, 1H), 3.39-3.29 (m, 1H), 3.12-3.03 (m, 1H), 2.79-2.54 (m, 3H), 1.89-1.86 (m, 1H), 1.62-1.61 (m, 1H), 1.17-1.00 (m, 1H); m/z calcd. for C$_{22}$H$_{23}$NO$_2$=333.17, found=333.35.

exo-benzyl 7-butyl-2-azabicyclo[2.2.2]oct-5-ene-2-carboxylate (63a): A solution of trifluoromethanesulfonic anhydride (1M in DCM) (5.0 mL, 5.0 mmol) in DCM (10 mL) was added dropwise to a solution of 60a (920 mg, 3.4 mmol) and pyridine (3.0 mL) in DCM (20 mL) with stirring at 0° C. over a period of 10 min, and the reaction mixture was then further stirred at 0° C. for 2 h. The mixture was diluted with DCM (30 mL), washed with 10% HCl and 5% NaHCO$_3$, and dried (Na$_2$SO$_4$). The solvent was removed under reduced pressure to afford essentially pure triflate product (1.41 g) as a colorless oil which was used for the next step without further purification.

To freshly prepared crude triflate (162 mg, 0.40 mmol) and Li$_2$CuCl$_4$ (0.12 mL; 0.012 mmol, 0.1 M in THF) solution in anhydrous Et$_2$O (2 mL) was added "PrMgCl (0.6 mL, 1.2 mmol, 2.0 M in THF) at −20° C. The reaction mixture was stirred for 6 h and the reaction was quenched with H$_2$O (2 mL), warmed to room temperature, and then acidified with 2N HCl (5 mL). The organic layer was separated, and the aqueous layer was extracted with DCM (10 mL×3). The combined organic layers were washed with water and brine, dried (Na$_2$SO$_4$), and concentrated to afford the crude product which was purified by flash column chromatography (silica gel, hexanes:EtOAc=9:1) to afford the pure product (85 mg, 0.28 mmol) in 70% yield for steps. Colorless oil; $^1$H NMR (400 MHz, CDCl$_3$) (spectrum complicated by rotomers) δ 7.36-7.28 (m, 5H), 6.49-6.40 (m, 1H), 6.33 (dt, J=8.4, 7.0 Hz, 1H), 5.24-5.03 (m, 2H), 4.55 (d, J=6.1 Hz, 1H), 3.27 (ddd, J=10.2, 5.7, 2.2 Hz, 1H), 3.02 (ddd, J=9.9, 5.9, 2.8 Hz, 1H), 2.73-2.60 (m, 1H), 1.67-1.21 (m, 8H), 1.04-0.98 (m, 1H), 0.86 (dt, J=23.0, 7.1 Hz, 3H); m/z calcd. for C$_{19}$H$_{25}$NO$_2$=299.19, found=299.94.

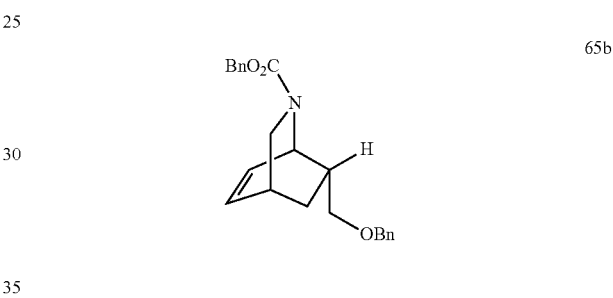

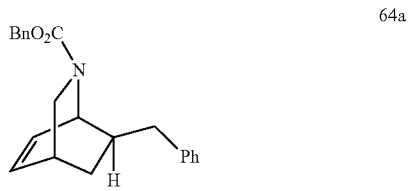

endo-benzyl 7-(benzyloxymethyl)-2-azabicyclo[2.2.2]oct-5-ene-2-carboxylate (65b): To a solution of 60b (546 mg, 2.0 mmol) in anhydrous THF (5 mL) was added NaH (96 mg of 60%, 4.0 mmol) at 0° C. The reaction mixture was stirred for 30 min at 0° C. and benzylbromide (0.30 mL, 2.4 mmol) was added at 0° C. The reaction mixture was warmed to room temperature and stirred for 16 h. The reaction mixture was then quenched with water (10 mL) and extracted with Et$_2$O (30 mL×3). The combined organic extracts were washed with brine (20 mL), dried over Na$_2$SO$_4$, and concentrated. Purification by flash column chromatography (silica gel, hexanes:EtOAc=9:1) gave the pure product (680 mg, 94%) as a colorless oil. $^1$H NMR (400 MHz, CDCl$_3$) (spectrum complicated by rotomers) δ 7.39-7.26 (m, 10H), 6.41-6.20 (m, 2H), 5.14 (d, J=15.7 Hz, 2H), 4.89 (ddd, J=17.8, 4.7, 2.9 Hz, 1H), 4.60-4.44 (m, 2H), 3.29 (d, J=10.3 Hz, 1H), 3.13-2.98 (m, 3H), 2.72 (d, J=16.1 Hz, 1H), 2.58-2.47 (m, 1H), 1.83-1.72 (m, 1H), 0.90-0.75 (m, 1H); m/z calcd. for C$_{23}$H$_{25}$NO$_3$=363.18, found=364.69.

Preparation of exo/endo-N-(methoxycarbonyl)-7-(pyridin-3-ylmethyl) substituted isoquinuclidines These compounds were prepared using a Ni-catalyzed aryl-alkyl coupling reaction reported by Molander (Molander, G. A. et al. 2010).

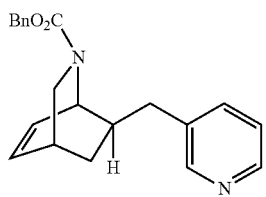

exo-benzyl 7-(pyridin-3-ylmethyl)-2-azabicyclo[2.2.2]oct-5-ene-2-carboxylate (66a): Potassium pyridine-3-trifluoroborate (157 mg, 0.85 mmol) and bathophenanthroline (27.7 mg, 0.0833 mmol) were combined under argon. NiBr$_2$·glyme (25.7 mg, 0.0833 mmol) and LiHMDS (418 mg, 2.50 mmol) were then added followed by dry sec-butanol (1.66 mL) in a glovebox and the mixture was sealed, removed from the glovebox, and stirred for 30 min. at room temperature. At this time, 61a (280 mg, 0.833 mmol) was added by syringe and the dark brown mixture was stirred at 60° C. for 18 h. During this period the mixture turned light brown. After cooling to room temperature, the reaction mixture was passed directly through a short silica plug and the plug was washed thoroughly with EtOAc (50 mL). The filtrate and washings were concentrated to yield a yellow-orange oil which was purified by flash column chromatography (silica gel, 60 to 70 to 80% gradient of EtOAc in hexanes) to yield a yellow oil (136 mg, 49% yield). $^1$H NMR (500 MHz, CDCl$_3$) (spectrum complicated by rotomers) δ 8.45 (d, J=5.6 Hz, 1H), 8.40 (d, J=5.7 Hz, 1H), 7.60 and 7.40-7.29 (d, J=7.8 Hz and buried peak, 1H), 7.40-7.29 (m, 5H), 7.22 and 6.99 (dd, J=7.7, 4.9 Hz, 1H), 6.47-6.30 (m, 2H), 5.21-5.10 (m, 2H), 4.56 and 4.41 (d, J=6.1 Hz, and J=5.7 Hz, 1H), 3.35 (ddd, J=14.9, 10.3, 2.0 Hz, 1H), 3.12-3.05 (m, 1H), 2.78-2.59 (m, 3H), 1.93-1.83 (br m, 1H), 1.68-1.60 (m, 1H), 1.16-1.07 (m, 1H). m/z calcd. for C$_{21}$H$_{22}$N$_2$O$_2$=334.17, found=335.18.

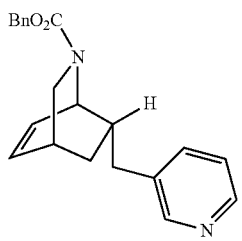

endo-benzyl 7-(pyridin-3-ylmethyl)-2-azabicyclo[2.2.2]oct-5-ene-2-carboxylate (66b): Prepared from 61b and potassium pyridine-3-trifluoroborate according to the procedure reported for 66a Purified by flash column chromatography (silica gel, 60 to 70 to 80% gradient of EtOAc in hexanes). Yellow oil, 50% yield. $^1$H NMR (400 MHz, CDCl$_3$) (spectrum complicated by rotomers) δ 8.46 (t, J=5.3 Hz, 1H), 8.39 (s, 1H), 7.53-7.41 (m, 1H), 7.37-7.27 (m, 4H), 7.24-7.15 (m, 2H), 6.55-6.44 (m, 1H), 6.44-6.29 (m, 1H), 5.15-4.98 (m, 2H), 4.64 and 4.45 (d, J=4.8 Hz and 5.5 Hz, 1H), 3.26 (dd, J=10.3, 1.9 Hz, 1H), 3.03-2.97 (m, 1H), 2.79 and 2.74 (br s, 1H), 2.59-2.34 (m, 2.4H), 2.27 (dd, J=13.1, 8.2 Hz, 0.6H), 1.90-1.82 and 1.79-1.71 (m, 1H), 1.01 (d, J=12.9 Hz, 1H). m/z calcd. for C$_{21}$H$_{22}$N$_2$O$_2$=334.17, found 334.98.

Preparation of sp$^2$ Series Isoquinuclidines

The 7-ethyl-isoquinuclidine with sp$^2$ hybridization at the 7-position was prepared as an example of the stereochemical series intermediate between exo and endo.

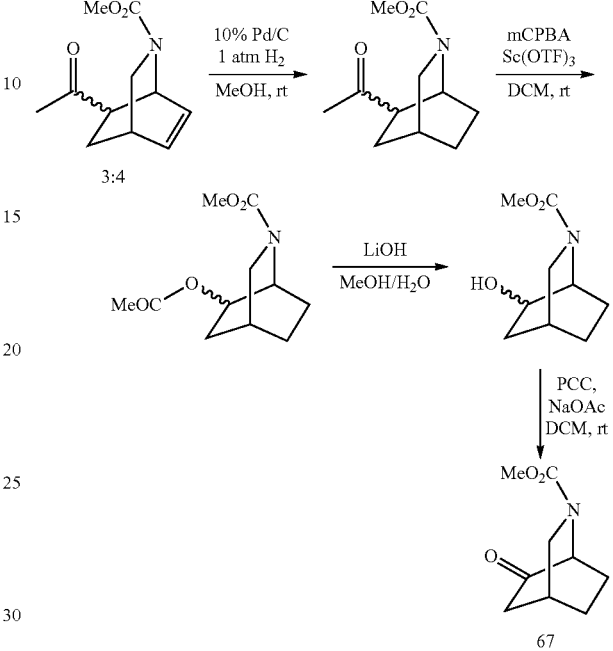

An exo:endo mixture of methyl 7-acetyl-2-azabicyclo[2.2.2]oct-5-ene-2-carboxylate (3:4) (7.00 g, 33.5 mmol) and 10% Pd/C (300 mg) were stirred in MeOH (60 mL) under 1 atm H$_2$ at room temperature until $^1$H NMR showed complete conversion. The reaction mixture was then concentrated in vacuo, diluted with 20% EtOAc in hexanes, and filtered through a short silica plug. The plug was washed with 30% EtOAc in hexanes and the combined filtrate and washings were concentrated to yield the hydrogenated product (~7.0 g) which was used in the next step without further purification.

The crude hydrogenated product (6.33 g, 30.0 mmol) was dissolved in dry DCM (600 mL) at room temperature under argon. Scandium triflate (2.95 g, 6.00 mmol) was then added followed by 75% m-chloroperoxybenzoic acid (110 g of 75%, 478 mmol) and the mixture was left to stir at room temperature for 24 h. The reaction was quenched with aqueous Na$_2$S$_2$O$_3$ and the organic layer was separated, washed with sat. aq. NaHCO$_3$ and H$_2$O, dried over Na$_2$SO$_4$, and concentrated to yield the crude ester product. This was dissolved in 1:1 MeOH:H$_2$O (750 mL), LiOH (20 g) was added, and the mixture was stirred at room temperature for 1.5 h. The methanol was then removed in vacuo and the aqueous mixture was extracted with DCM. The combined organics were washed with H$_2$O, dried over Na$_2$SO$_4$, and concentrated to yield the crude product. This was purified by flash column chromatography (silica gel, 30 to 60 to 100% EtOAc in hexanes) to yield the mixed exo/endo-alcohol (2.9 g) which was used directly in the next step.

Pyridinium chlorochromate (6.00 g, 27.8 mmol) and sodium acetate (6.00 g, 73.1 mmol) were suspended in dry DCM (120 mL) at room temperature under argon. After stirring for 10 min. the exo/endo-alcohol (2.9 g, 15.7 mmol) was added and the resulting mixture was stirred for 3 h. Et$_2$O was then added and the mixture was stirred vigorously for an additional 1 h before filtering through celite. After washing the filter cake with Et$_2$O, the combined filtrate and washings were concentrated to yield the crude product which was purified by flash column chromatography (silica gel, 20 to 40% EtOAc in hexanes) to yield 67 as a light-brown waxy solid (2.79 g, 48% yield for 4 steps). $^1$H NMR (400 MHz, CDCl$_3$) (spectrum complicated by rotamers) δ 4.38-4.23 (m, 1H), 3.71-3.69 (m, 3H), 3.54-3.40 (m, 2H), 2.45-2.34 (m, 3H), 2.22-2.09 (m, 1H), 1.98-1.87 (m, 1H), 1.74 (t, J=11.9 Hz, 1H), 1.68-1.57 (m, 1H); $^{13}$C NMR (101 MHz, CDCl$_3$) δ 207.5, 155.8, 55.4 and 54.7 (1C), 52.8, 48.2, 43.2 and 43.1 (1C), 28.5 and 28.3 (1C), 24.8, 23.0; m/z calcd. for C$_9$H$_{13}$NO$_3$=183.09, found=184.12.

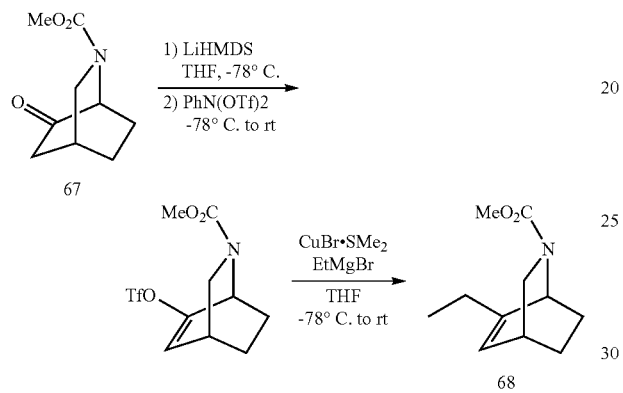

Methyl 6-ethyl-2-azabicyclo[2.2.2]oct-5-ene-2-carboxylate (68): To a solution of 67 (550 mg, 3.00 mmol) in dry THF (20 mL) at −78° C. under argon, was slowly added 1M LiHMDS in THF (4.50 mL, 4.50 mmol) and the mixture was stirred for 20 min. N-Phenyl-bis(trifluoromethanesulfonimide) (1.60 g, 4.50 mmol) was then added and the mixture was allowed to warm to room temperature and stirred overnight. After cooling to 0° C., the reaction was quenched with sat. aq. NH$_4$Cl, diluted with water, and extracted with Et$_2$O. The combined organic extracts were washed with H$_2$O, dried over Na$_2$SO$_4$, and concentrated to yield the crude vinyl triflate. This was purified by flash column chromatography (silica gel, 6 to 11 to 20% EtOAc in hexanes) to yield the pure vinyl triflate (0.80 g) which was used directly in the next step.

To a stirred suspension of copper(I) bromide dimethyl sulfide complex (1.57 g, 7.64 mmol) in dry THF (30 mL) at −78° C. under argon, was slowly added 3M EtMgBr in Et$_2$O (4.60 mL, 13.8 mmol). The cooling bath was then temporarily removed and the solution warmed until a black color developed (10-15 min). After cooling back to −78° C., a solution of the vinyl triflate (0.80 g, 2.54 mmol) in dry THF was added dropwise and the reaction mixture was warmed to room temperature and stirred for 17 h. The reaction was then quenched with sat. aqueous NH$_4$Cl at −20° C., diluted with H$_2$O, and extracted with DCM. The combined organic extracts were dried over Na$_2$SO$_4$ and concentrated to yield the crude product which was purified by flash column chromatography (silica gel, 6% to 12% EtOAc in hexanes) to yield 68 as a colorless oil (410 mg, 70% yield for 2 steps). $^1$H NMR (400 MHz, CDCl$_3$) (spectrum complicated by rotamers) δ 5.90 (br t, J=5.3 Hz, 1H), 4.60 and 4.44 (br s, 1H), 3.69 and 3.66 (s, 3H), 3.27-3.20 (m, 1H), 3.00-2.89 (m, 1H), 2.71-2.63 (m, 1H), 2.23-2.10 (m, 2H), 1.99-1.88 (m, 1H), 1.62-1.54 (m, 1H), 1.39-1.31 (m, 2H), 1.03 (td, J=7.4, 3.4 Hz, 3H); m/z calcd. for C$_{11}$H$_{17}$NO$_2$=195.13, found=196.26.

Preparation of Aryl Fragments 3-(2-bromoethyl)indole was commercially available from Sigma-Aldrich (St. Louis, Mo.). Other bromoethylarenes were prepared according to literature procedures as shown in the schemes below.

Additional bromoethylindoles were prepared by Fischer-type indole synthesis followed by bromination (Campos, K. R. et al. 2004; Mewshaw, R. R. et al. 2004) (Scheme 16), acylation of substituted indoles with oxalyl chloride (Woodward, R. B. et al. 1958) followed by reduction (Feldman, et al. 1986) and bromination (Scheme 17). 3-(2-bromoethyl) benzofuran (Kozikowski, A. P. et al. 2007; Tomaszewski, Z. et al. 1992) and 3-(2-bromoethyl)benzothiophene were prepared according to the protocols in Scheme 18. 3-indolylacetaldehyde was prepared by Parikh-Doering oxidation of tryptophol (Sugawara, S. et al. 2009), 3-(2-oxoethyl)-1H-indole-2-carboxylate was prepared from 2-(carboethoxy)indole via literature procedures (Buechi, G. et al. 1977; Vega, A. M. et al. 1981), and 2-(2-chloroethyl)benzimidazole was prepared by condensation of o-phenylenediamine and 3-chloropropionic acid (Cowart, M. et al. 2004)(Scheme 19).

EXAMPLE 12

Preparation of Additional Isoquinuclidine Derivatives

General Procedure A for Preparation of N-arylalkyl-isoquinuclidines:

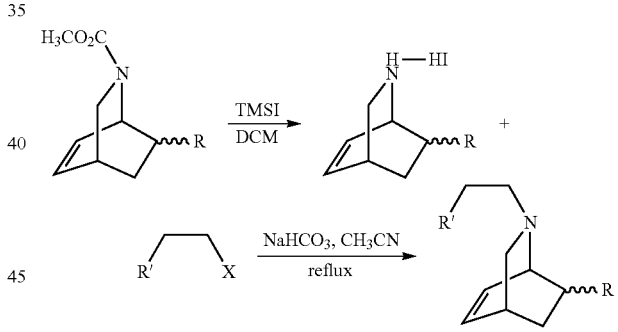

Iodotrimethylsilane (4 equiv.) was added to a solution of the corresponding N-(methoxycarbonyl)-isoquinuclidine (1 equiv., 0.125 M) in anhydrous DCM at 0° C. under argon. After 5 min, the mixture was allowed to warm to r.t and left to stir until TLC indicated that no starting material remained (1-2 h). The reaction was then quenched with MeOH and concentrated in vacuo to give the crude decarboxylated isoquinuclidine as the hydroiodide salt, which was used for the next step without further purification. A suspension of sodium bicarbonate (4 equiv.) in anhydrous acetonitrile containing the isoquinuclidine HI salt (0.21 M) and the corresponding alkyl halide (1 equiv.) was stirred at reflux under argon until TLC showed complete consumption of alkyl halide (1-3 days). After cooling to room temperature, the reaction mixture was diluted with water, basified with NaOH, and extracted with CHCl$_3$ (three portions). The combined organic layers were washed with 10% NaHCO$_3$, dried over Na$_2$SO$_4$ or MgSO$_4$, concentrated in vacuo, and purified by flash column chromatography on silica gel.

General Procedure B for Preparation of N-aryalkyl-isoquinuclidines

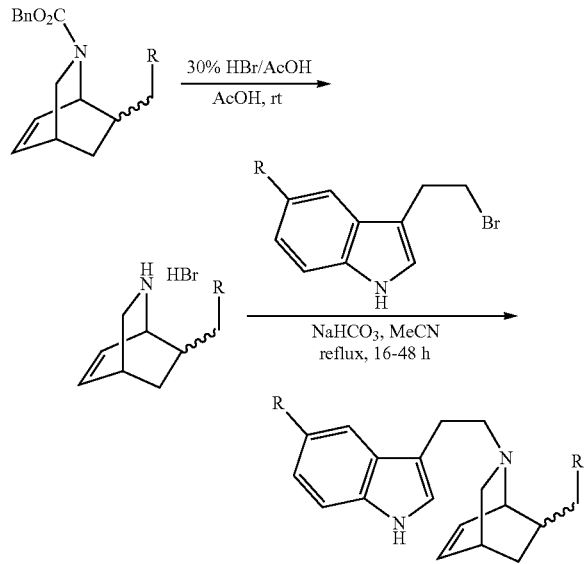

To a stirred solution of the N-(benzyloxycarbonyl)-isoquinuclidine in AcOH, HBr (33%) in AcOH was added dropwise at room temperature. The reaction was stirred for 3 h and evaporated under high vacuum for a longer time (usually 3 hr) to remove all trace of AcOH. The resulting mixture containing deprotected isoquinuclidine hydrobromide was used in the next step without purification. The isoquinuclidine HBr salt was treated with the required amount of bromoalkylheteroarene (1 eq.) and NaHCO$_3$ (4 eq.) and refluxed in CH$_3$CN until the starting material was consumed. After quenching with water the mixture was extracted with CHCl$_3$ (10 mL×3). The combined organic layers were washed with water, brine, dried (Na$_2$SO$_4$), and concentrated to afford the crude product which was purified by flash column chromatography.

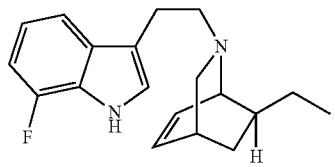 [SMILES: CCC1CC2C=CC1N(CCc1c[nH]c3c(F)cccc13)C2]

exo-7-ethyl-2-(2-(7-fluoro-1H-indol-3-yl)ethyl)-2-azabicyclo [2.2.2]oct-5-ene (69): Prepared from 7 and 3-(2-bromoethyl)-7-fluoroindole according to general procedure A. Purified by repeated flash column chromatography (silica gel, hexanes:EtOAc mixtures +/−1-2% Et$_3$N). Pale-yellow oil, 42% yield. $^1$H NMR (500 MHz, CDCl$_3$) δ 8.08 (br s, 1H), 7.35 (d, J=7.9 Hz, 1H), 7.07 (s, 1H), 7.01 (td, J=7.9, 4.8 Hz, 1H), 6.88 (dd, J=11.2, 7.8 Hz, 1H), 6.33 (dt, J=12.5, 7.1 Hz, 2H), 3.26 (d, J=5.2 Hz, 1H), 3.11 (dd, J=9.1, 2.1 Hz, 1H), 2.92-2.75 (m, 3H), 2.57-2.49 (m, 1H), 2.47-2.42 (br m, 1H), 1.97 (dt, J=9.1, 2.4 Hz, 1H), 1.65-1.52 (m, 2H), 1.52-1.45 (m, 1H), 1.31 (ddd, J=10.6, 5.2, 2.2 Hz, 1H), 0.96-0.92 (m, 1H), 0.90 (t, J=7.5 Hz, 3H); $^{13}$C NMR (101 MHz, CDCl$_3$) δ 151.0 and 148.6 (1C), 133.0, 132.9, 131.7 and 131.6 (1C), 124.6 and 124.4 (1C), 122.34, 119.43 and 119.36 (1C), 116.23, 114.85 and 114.82 (1C), 106.8 and 106.6 (1C), 59.0, 56.3, 56.2, 41.4, 31.8, 29.9, 27.4, 24.5, 12.7; m/z calcd. for C$_{19}$H$_{23}$FN$_2$=298.18, found=299.23.

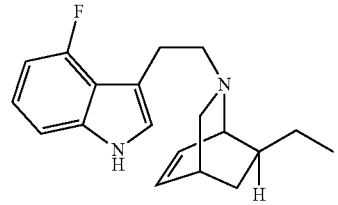 [SMILES: CCC1CC2C=CC1N(CCc1c[nH]c3cccc(F)c13)C2]

exo-7-ethyl-2-(2-(4-fluoro-1H-indol-3-yl)ethyl)-2-azabicyclo[2.2.2]oct-5-ene (70): Prepared from 7 and 3-(2-bromoethyl)-4-fluoroindole according to general procedure A. Purified by repeated flash column chromatography (silica gel, hexanes:EtOAc mixtures +/−2% Et$_3$N). Pale yellow-orange oil, 51% yield. $^1$H NMR (400 MHz, CDCl$_3$) δ 8.06 (br s, 1H), 7.06 (ddd, J=13.0, 10.9, 6.5 Hz, 2H), 6.97 (s, 1H), 6.77-6.68 (m, 1H), 6.38-6.27 (m, 2H), 3.32-3.28 (m, 1H), 3.12 (dd, J=9.2, 2.1 Hz, 1H), 3.04-2.87 (m, 2H), 2.87-2.78 (m, 1H), 2.57-2.49 (m, 1H), 2.44 (br d, J=2.2 Hz, 1H), 2.00 (dt, J=9.2, 2.4 Hz, 1H), 1.64-1.53 (m, 2H), 1.49 (ddd, J=14.6, 6.1, 3.0 Hz, 1H), 1.36-1.23 (m, 1H), 0.94 (ddd, J=12.2, 4.9, 2.1 Hz, 1H), 0.89 (t, J=7.4 Hz, 3H); $^{13}$C NMR (101 MHz, CDCl$_3$) δ 158.8 and 156.3 (1C), 139.2 and 139.1 (1C), 133.0, 132.9, 122.4 and 122.3 (1C), 121.9, 116.6 and 116.4 (1C), 114.0, 107.23 and 107.19 (1C), 104.6 and 104.4 (1C), 59.74 and 59.73 (1C), 56.2, 56.0, 41.3, 31.7, 29.9, 27.3, 25.6, 12.6; m/z calcd. for C$_{19}$H$_{23}$FN$_2$=298.18, found=299.24.

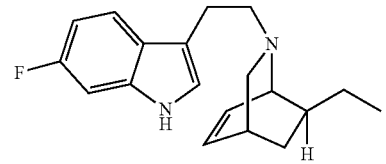 [SMILES: CCC1CC2C=CC1N(CCc1c[nH]c3cc(F)ccc13)C2]

exo-7-ethyl-2-(2-(6-fluoro-1H-indol-3-yl)ethyl)-2-azabicyclo[2.2.2]oct-5-ene (71): Prepared from 8 and 3-(2-bromoethyl)-6-fluoroindole according to general procedure A. Purified by repeated flash column chromatography (silica gel, hexanes:EtOAc mixtures +/−2% Et$_3$N). Pale-yellow oil, 11% yield (low yield due to poor purification). $^1$H NMR (500 MHz, CDCl$_3$) δ 7.91 (br s, 1H), 7.48 (dd, J=8.7, 5.4 Hz, 1H), 7.04-6.98 (m, 2H), 6.87 (ddd, J=9.6, 8.7, 2.3 Hz, 1H), 6.37-6.27 (m, 2H), 3.26 (dd, J=3.6, 1.7 Hz, 1H), 3.10 (dd, J=9.1, 2.3 Hz, 1H), 2.90-2.73 (m, 3H), 2.54-2.48 (m, 1H), 2.44 (br ddd, J=7.7, 3.8, 2.2 Hz, 1H), 1.95 (dt, J=9.1, 2.6 Hz, 1H), 1.65-1.51 (m, 2H), 1.51-1.44 (m, 1H), 1.34-1.26 (m, 1H), 0.96-0.91 (m, 1H), 0.89 (t, J=7.4 Hz, 3H); $^{13}$C NMR (126 MHz, CDCl$_3$) δ 161.0 and 159.1 (1C), 136.2 and 136.1 (1C), 133.3, 132.6, 124.4, 121.9, 119.8 and 119.7 (1C), 115.1, 108.1 and 107.9 (1C), 97.5 and 97.3 (1C), 59.0, 56.3, 56.1, 41.1, 31.6, 29.7, 27.3, 24.3, 12.7; m/z calcd. for C$_{19}$H$_{23}$FN$_2$=298.18, found=299.23.

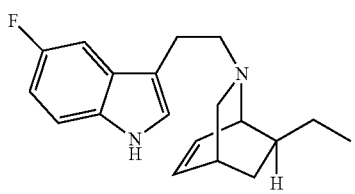 [SMILES: CCC1CC2C=CC1N(CCc1c[nH]c3ccc(F)cc13)C2]

exo-7-ethyl-2-(2-(5-fluoro-1H-indol-3-yl)ethyl)-2-azabicyclo[2.2.2]oct-5-ene (72): Prepared from 7 and 3-(2-bromoethyl)-5-fluoroindole according to general procedure A. Purified by flash column chromatography (silica gel, column treated with 2% Et$_3$N in hexanes, then eluted with 6:1 to 7:3 hexanes:EtOAc). Pale-yellow oil, 47% yield. $^1$H NMR (400 MHz, CDCl$_3$) δ 7.95 (br s, 1H), 7.27-7.20 (m, 2H), 7.07 (d, J=2.3 Hz, 1H), 6.92 (td, J=9.1, 2.5 Hz, 1H), 6.38-6.27 (m, 2H), 3.26 (dt, J=4.9, 1.6 Hz, 1H), 3.11 (dd, J=9.1, 2.3 Hz, 1H), 2.89-2.70 (m, 3H), 2.55-2.48 (m, 1H), 2.45 (br ddd, J=7.8, 3.8, 2.0 Hz, 1H), 1.96 (dt, J=9.1, 2.6 Hz, 1H), 1.66-1.53 (m, 2H), 1.53-1.44 (m, 1H), 1.36-1.26 (m, 1H), 0.97-0.92 (m, 1H), 0.90 (t, J=7.4 Hz, 3H); $^{13}$C NMR (125 MHz, CDCl$_3$) δ 158.7 and 156.9 (1C), 133.0, 132.83, 132.78, 128.2, 123.5, 115.6, 111.7 and 111.6 (1C), 110.3 and 110.1 (1C), 104.1 and 103.9 (1C), 59.0, 56.4, 56.2, 41.3, 31.8, 29.9, 27.4, 24.5, 12.7; m/z calcd. for C$_{19}$H$_{23}$FN$_2$=298.18, found=299.24.

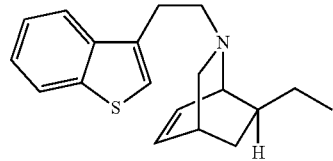 [SMILES: CCC1CC2C=CC1N(CCc1csc3ccccc13)C2]

exo-2-(2-(benzo[b]thiophen-3-yl)ethyl)-7-ethyl-2-azabicyclo[2.2.2]oct-5-ene (73): Prepared from 7 and 3-(2-bromoethyl)benzo[b]thiophene according to general procedure A. Purified by repeated flash column chromatography (silica gel, hexanes:EtOAc mixtures). Yellow-orange oil, 55% yield. $^1$H NMR (400 MHz, CDCl$_3$) δ 7.87-7.82 (m, 1H), 7.78-7.73 (m, 1H), 7.41-7.30 (m, 2H), 7.18 (s, 1H), 6.38-6.28 (m, 2H), 3.24 (dt, J=5.1, 1.7 Hz, 1H), 3.11 (dd, J=9.1, 2.3 Hz, 1H), 3.01-2.79 (m, 3H), 2.63-2.53 (m, 1H), 2.45 (br ddd, J=7.7, 3.8, 2.2 Hz, 1H), 1.97 (dt, J=9.1, 2.6 Hz, 1H), 1.66-1.52 (m, 2H), 1.52-1.44 (m, 1H), 1.36-1.28 (m, 1H), 0.93 (ddd, J=12.4, 4.9, 2.3 Hz, 1H), 0.89 (t, J=7.4 Hz, 3H); $^{13}$C NMR (101 MHz, CDCl$_3$) δ 140.4, 139.4, 135.5, 133.1, 132.8, 124.1, 123.9, 123.0, 121.8, 121.7, 58.1, 56.3 (2C), 41.3, 31.8, 29.9, 27.8, 27.3, 12.6; m/z calcd. for C$_{19}$H$_{23}$NS=297.16, found=298.27.

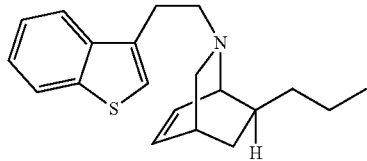 [SMILES: CCCC1CC2C=CC1N(CCc1csc3ccccc13)C2]

exo-2-(2-(1H-indol-3-yl)ethyl)-7-propyl-2-azabicyclo[2.2.2]oct-5-ene (74): Prepared from 58a and 3-(2-bromoethyl)indole according to general procedure A. Purified by flash column chromatography (silica gel, 5:1 hexanes:EtOAc+2% Et$_3$N). Yellow oil, 48% yield. $^1$H NMR (400 MHz, CDCl$_3$) δ 7.91 (br s, 1H), 7.62 (d, J=7.7 Hz, 1H), 7.34 (d, J=8.0 Hz, 1H), 7.19 (td, J=7.6, 1.1 Hz, 1H), 7.13 (td, J=7.5, 0.9 Hz, 1H), 7.03 (d, J=2.2 Hz, 1H), 6.39-6.30 (m, 2H), 3.29-3.24 (m, 1H), 3.15 (dd, J=9.1, 2.2 Hz, 1H), 2.96-2.77 (m, 3H), 2.61-2.52 (m, 1H), 2.46 (br d, J=2.2 Hz, 1H), 2.00 (dt, J=9.1, 2.3 Hz, 1H), 1.66-1.40 (m, 4H), 1.41-1.27 (m, 2H), 1.00-0.95 (m, 1H), 0.93 (t, J=7.3 Hz, 3H); $^{13}$C NMR (126 MHz, CDCl$_3$) δ 136.3, 133.0, 132.9, 127.9, 121.9, 121.6, 119.2, 119.1, 115.3, 111.1, 59.2, 56.5, 56.4, 39.1, 36.9, 31.8, 30.0, 24.5, 21.3, 14.6; m/z calcd. for C$_{20}$H$_{26}$N$_2$=294.21, found=294.97.

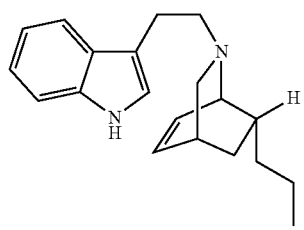 [SMILES: CCCC1CC2C=CC1N(CCc1c[nH]c3ccccc13)C2]

endo-2-(2-(1H-indol-3-yl)ethyl)-7-propyl-2-azabicyclo[2.2.2]oct-5-ene (75): Prepared from 58b and 3-(2-bromoethyl)indole according to general procedure A. Purified by flash column chromatography (silica gel, 6:4 to 1:1 hexanes:EtOAc+2% Et$_3$N). Yellow oil, 38% yield. 1H NMR (400 MHz, CDCl$_3$) δ 8.07 (s, 1H), 7.61 (d, J=7.7 Hz, 1H), 7.34 (d, J=8.1 Hz, 1H), 7.18 (t, J=7.6 Hz, 1H), 7.11 (t, J=7.2 Hz, 1H), 6.99 (d, J=2.1 Hz, 1H), 6.39 (t, J=7.3 Hz, 1H), 6.16 (t, J=6.8 Hz, 1H), 3.42-3.37 (m, 1H), 3.05 (dd, J=9.7, 1.6 Hz, 1H), 3.01-2.82 (m, 3H), 2.63-2.54 (m, 1H), 2.54-2.48 (br m, 1H), 2.21-2.10 (br m, 2H), 1.80 (ddd, J=12.1, 9.3, 2.7 Hz, 1H), 1.37-1.23 (m, 2H), 1.17 (ddt, J=13.2, 9.2, 6.5 Hz, 1H), 1.03-0.92 (m, 1H), 0.88 (t, J=7.3 Hz, 3H), 0.84-0.77 (m, 1H); $^{13}$C NMR (126 MHz, CDCl$_3$) δ 136.4, 133.6, 130.4, 127.7, 122.0, 121.5, 119.3, 119.1, 115.0, 111.2, 59.1, 57.6, 54.5, 38.5, 38.4, 31.6, 31.0, 24.6, 20.2, 14.4; m/z calcd. for C$_{20}$H$_{26}$N$_2$=294.21, found=295.26.

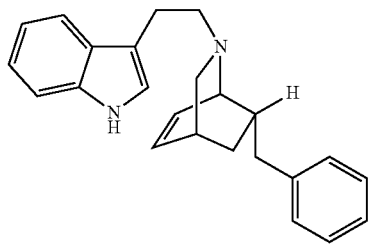 [SMILES: C1=CC2C(Cc3ccccc3)CC1CN2CCc1c[nH]c2ccccc12]

endo-2-(2-(1H-indol-3-yl)ethyl)-7-benzyl-2-azabicyclo[2.2.2]oct-5-ene (76): Prepared from 54 and 3-(2-bromoethyl) indole according to general procedure A. Purified by repeated flash column chromatography (silica gel, 6:4 hexanes:EtOAc+2% Et$_3$N). Yellow oil, 37% yield. $^1$H NMR (400 MHz, CDCl$_3$) δ 7.96 (s, 1H), 7.56 (d, J=7.9 Hz, 1H), 7.34-7.25 (m, 3H), 7.22-7.14 (m, 4H), 7.12-7.07 (m, 1H), 6.92 (d, J=2.1 Hz, 1H), 6.47 (t, J=7.3 Hz, 1H), 6.25-6.19 (m, 1H), 3.32-3.27 (m, 1H), 3.06 (dd, J=9.7, 1.9 Hz, 1H), 2.93-2.76 (m, 3H), 2.59-2.49 (m, 3H), 2.47-2.31 (m, 2H), 2.13 (dt, J=9.7, 2.6 Hz, 1H), 1.79 (ddd, J=12.2, 9.1, 2.7 Hz, 1H), 0.94-0.86 (m, 1H); $^{13}$C NMR (126 MHz, CDCl$_3$) δ 140.8, 136.3, 133.9, 130.2, 129.1 (2C), 128.4 (2C), 127.7, 125.9, 122.0, 121.5, 119.3, 119.1, 114.9, 111.2, 59.1, 56.8, 54.5, 42.1, 40.1, 31.6, 30.5, 24.6; m/z calcd. for C$_{24}$H$_{26}$N$_2$=342.21, found=343.20.

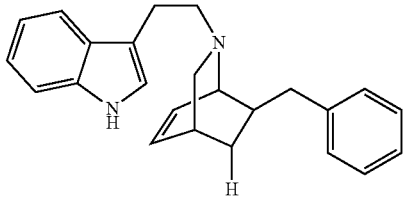 [SMILES: C1=CC2C(Cc3ccccc3)CC1CN2CCc1c[nH]c2ccccc12]

exo-2-(2-(1H-indol-3-yl)ethyl)-7-benzyl-2-azabicyclo[2.2.2]oct-5-ene (77): Prepared from 48 and 3-(2-bromoethyl)indole according to general procedure A. Purified by repeated flash column chromatography (silica gel, hexanes:EtOAc mixtures+2% Et$_3$N (first two columns) then DCM+2% Et$_3$N (final column)). Yellow oil, 26% yield (low yield due to poor purification). $^1$H NMR (500 MHz, CDCl$_3$) δ 7.92 (br s, 1H), 7.63 (d, J=7.8 Hz, 1H), 7.36 (d, J=8.1 Hz, 1H), 7.21 (t, J=7.5 Hz, 1H), 7.17-7.11 (m, 4H), 7.06-7.00 (m, 3H), 6.34 (t, J=7.2 Hz, 1H), 6.21-6.16 (m, 1H), 3.23 (dd, J=9.1, 2.2 Hz, 1H), 3.02 (d, J=5.4 Hz, 1H), 2.94-2.83 (m, 3H), 2.82-2.73 (m, 2H), 2.56-2.51 (m, 1H), 2.51-2.46 (br m, 1H), 2.03 (dt, J=9.1, 2.5 Hz, 1H), 1.73-1.65 (m, 1H), 1.55-1.47 (m, 1H), 1.05 (ddd, J=12.3, 4.8, 2.0 Hz, 1H); $^{13}$C NMR (126 MHz, CDCl$_3$) δ 142.2, 136.4, 133.0, 132.8, 129.3 (2C), 128.2 (2C), 127.9, 125.6, 122.0, 121.7, 119.3, 119.1, 115.4, 111.2, 59.2, 56.3, 55.4, 41.4, 40.1, 31.8, 30.1, 24.6; m/z calcd. for C$_{24}$H$_{26}$N$_2$=342.21, found 342.91.

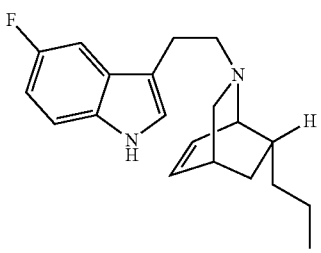 [SMILES: CCCC1CC2C=CC1N(CCc1c[nH]c3ccc(F)cc13)C2]

endo-2-(2-(5-fluoro-1H-indol-3-yl)ethyl)-7-propyl-2-azabicyclo[2.2.2]oct-5-ene (78): Prepared from 58b and 3-(2-bromoethyl)-5-fluoroindole according to general procedure A. Purified by repeated flash column chromatography (silica gel, 1:1 hexanes:EtOAc+2% Et$_3$N (first column) then gradient of MeOH in DCM+2% Et$_3$N (second column)). Off-white solid, 42% yield. $^1$H NMR (400 MHz, CDCl$_3$) δ 8.11 (br s, 1H), 7.23 (dt, J=9.6, 3.7 Hz, 2H), 7.03 (d, J=2.2 Hz, 1H), 6.91 (td, J=9.1, 2.5 Hz, 1H), 6.39 (t, J=7.3 Hz, 1H), 6.18-6.11 (m, 1H), 3.37 (br s, 1H), 3.04 (dd, J=9.7, 1.8 Hz, 1H), 2.93-2.78 (m, 3H), 2.60-2.46 (m, 2H), 2.19-2.07 (m, 2H), 1.79 (ddd, J=12.1, 9.2, 2.8 Hz, 1H), 1.35-1.25 (m, 2H), 1.18-1.09 (m, 1H), 1.02-0.90 (m, 1H), 0.87 (t, J=7.3 Hz, 3H), 0.83-0.75 (m, 1H); $^{13}$C NMR (126 MHz, CDCl$_3$) δ 158.7 and 156.9 (1C), 133.7, 132.9, 130.3, 128.14 and 128.06 (1C), 123.5, 115.1, 111.8 and 111.7 (1C), 110.4 and 110.2 (1C), 104.0 and 103.9, 58.9, 57.6, 54.4, 38.4, 38.7, 31.6, 30.9, 24.6, 20.2, 14.4; m/z calcd. for C$_{20}$H$_{25}$FN$_2$=312.20, found=313.24.

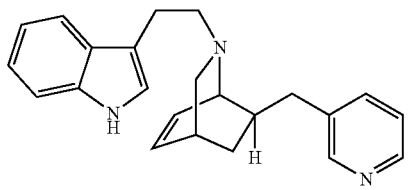 [SMILES: C1=CC2C(Cc3cccnc3)CC1CN2CCc1c[nH]c2ccccc12]

exo-2-(2-(5-fluoro-1H-indol-3-yl)ethyl)-7-propyl-2-azabicyclo[2.2.2]oct-5-ene (79): Prepared from 58a and 3-(2-bromoethyl)-5-fluoroindole according to general procedure A. Purified by flash column chromatography (silica gel, 5:1 to 8:2 gradient of hexanes:EtOAc+2% Et$_3$N). Yellow oil, 58% yield. $^1$H NMR (400 MHz, CDCl$_3$) δ 7.93 (br s, 1H), 7.26-7.21 (m, 2H), 7.07 (d, J=2.2 Hz, 1H), 6.92 (td, J=9.0, 2.5 Hz, 1H), 6.38-6.27 (m, 2H), 3.22 (d, J=5.2 Hz, 1H), 3.12 (dd, J=9.1, 2.3 Hz, 1H), 2.89-2.69 (m, 3H), 2.59-2.47 (m, 1H), 2.45 (br s, 1H), 1.96 (dt, J=9.1, 2.4 Hz, 1H), 1.62-1.37 (m, 4H), 1.37-1.25 (m, 2H), 0.97-0.92 (m, 1H), 0.90 (t, J=7.3 Hz, 3H); $^{13}$C NMR (126 MHz, CDCl$_3$) δ 158.7 and 156.9 (1C), 132.9 (2C), 132.8, 128.3 and 128.2 (1C), 123.5, 115.5, 111.7 and 111.6 (1C), 110.3 and 110.1 (1C), 104.1 and 103.9 (1C), 59.0, 56.6, 56.4, 39.1, 36.9, 31.8, 30.0, 24.4, 21.3, 14.6; m/z calcd. for C$_{20}$H$_{25}$FN$_2$=312.20, found=313.34.

exo-2-(2-(1H-indol-3-yl)ethyl)-7-(pyridin-3-ylmethyl)-2-azabicyclo[2.2.2]oct-5-ene (80):

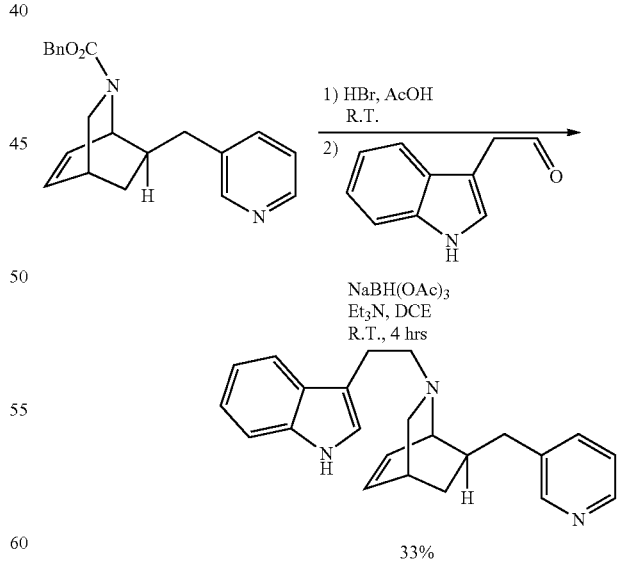

66a (67 mg, 0.20 mmol) was dissolved in glacial AcOH (0.60 mL) under argon, 33% HBr in AcOH (0.80 mL) was added, and the solution was stirred at room temperature for 1 h. The volatiles were then removed in vacuo and the resulting pale-brown solid (deprotected isoquinuclidine, HBr salt) was dried under high vacuum for 1 h. At this time, dry dichloroethane (1.2 mL) was added followed by triethylamine (0.056 mL, 40 mg, 0.40 mmol), 3-indolylacetaldehyde (32 mg, 0.20 mmol), and sodium triacetoxyborohydride (85 mg, 0.40 mmol) and the resulting orange-red mixture was stirred at room temperature for 4 h. The reaction was then quenched with $H_2O$ (10 mL) and extracted with $CHCl_3$ (3×5 mL). The combined organics were washed with $H_2O$ (5 mL) and brine (5 mL), dried over $Na_2SO_4$, and concentrated to yield a brown oil. This was purified by flash column chromatography (silica gel, DCM+2% $Et_3N$) to yield a light brown oil (23 mg, 33% yield). $^1H$ NMR (500 MHz, $CDCl_3$) δ 8.39-8.35 (m, 2H), 8.11 (br s, 1H), 7.62 (d, J=7.8 Hz, 1H), 7.35 (d, J=8.0 Hz, 1H), 7.22-7.11 (m, 3H), 7.03 (d, J=1.9 Hz, 1H), 6.97 (dd, J=7.7, 4.8 Hz, 1H), 6.35 (t, J=7.2 Hz, 1H), 6.20-6.16 (m, 1H), 3.23 (dd, J=9.2, 2.2 Hz, 1H), 2.96 (d, J=5.5 Hz, 1H), 2.92-2.81 (m, 3H), 2.80-2.71 (m, 2H), 2.54 (ddd, J=7.8, 6.2, 3.4 Hz, 1H), 2.52-2.48 (br m, 1H), 2.04 (dt, J=9.1, 2.5 Hz, 1H), 1.71-1.63 (m, 1H), 1.51 (ddd, J=10.9, 6.1, 3.1 Hz, 1H), 1.03 (ddd, J=12.3, 4.7, 2.1 Hz, 1H); $^{13}C$ NMR (126 MHz, $CDCl_3$) δ 150.6, 147.1, 137.3, 136.9, 136.4, 133.3 (br), 132.4 (br), 127.9, 123.3, 122.0, 121.8, 119.3, 119.0, 115.2 (br), 111.3, 59.3, 56.1, 55.5, 40.9, 37.1, 31.7, 30.0, 24.5; m/z calcd. for $C_{23}H_{25}N_3$=343.20, found 344.19.

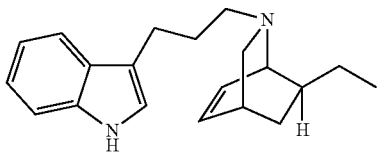 [SMILES: CCC1CC2C=CC1N(CCCc1c[nH]c3ccccc13)C2]

exo-2-(3-(1H-indol-3-yl)propyl)-7-ethyl-2-azabicyclo[2.2.2]oct-5-ene (81): Prepared from B7 and 3-(3-bromopropyl)indole according to general procedure A. Purified by flash column chromatography (silica gel, 15 to 20% gradient of EtOAc in hexanes). Pale-yellow oil, 58% yield. $^1H$ NMR (400 MHz, $CDCl_3$) δ 7.88 (bs s, 1H), 7.62 (d, J=7.9 Hz, 1H), 7.35 (d, J=8.1 Hz, 1H), 7.21-7.15 (m, 1H), 7.13-7.08 (m, 1H), 6.99-6.96 (m, 1H), 6.34-6.23 (m, 2H), 3.19-3.16 (br m, 1H), 3.05 (dd, J=9.1, 2.3 Hz, 1H), 2.88-2.71 (m, 2H), 2.51 (dt, J=11.8, 7.4 Hz, 1H), 2.43-2.37 (br m, 1H), 2.30-2.21 (m, 1H), 1.87-1.69 (m, 3H), 1.68-1.53 (m, 2H), 1.51-1.42 (m, 1H), 1.34-1.24 (m, 1H), 0.96-0.88 (m, 1H), 0.92 (t, J=7.4 Hz, 3H); $^{13}C$ NMR (126 MHz, $CDCl_3$) δ 136.5, 132.9 (2C), 127.8, 121.9, 121.3, 119.20, 119.16, 117.2, 111.1, 58.1, 56.4, 55.9, 41.5, 31.8, 30.0, 29.0, 27.4, 22.8, 12.7; m/z calcd. for $C_{20}H_{26}N_2$=294.21, found=295.24.

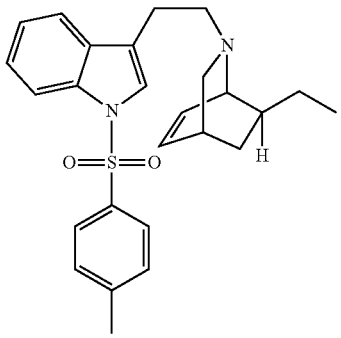 [SMILES: CCC1CC2C=CC1N(CCc1cn(S(=O)(=O)c3ccc(C)cc3)c3ccccc13)C2]

exo-7-ethyl-2-(2-(1-tosyl-1H-indol-3-yl)ethyl)-2-azabicyclo[2.2.2]oct-5-ene (82): 10a (140 mg, 0.50 mmol), p-toluenesulfonyl chloride (167 mg, 0.875 mmol), and tetrabutylammonium bisulfate (17 mg, 0.050 mmol) were dissolved in DCM (2.5 mL), 50% m/m aq. NaOH (0.25 mL) was added, and the mixture was left to stir at room temperature under argon for 12 h. The reaction was then diluted with $H_2O$ (5 mL) and DCM (2.5 mL) and the organic layer was separated. The remaining aqueous was extracted with additional DCM (2×5 mL) and the combined organics were washed with $H_2O$ (2×5 mL) and brine (5 mL), dried over $Na_2SO_4$, and concentrated. The resulting off-white solid was purified by flash column chromatography (silica gel, 9:1 hexanes:EtOAc+2% $Et_3N$) to yield a tan solid. NMR revealed that impurities still remained so this material was dissolved in a 1:1 mixture of hexanes and DCM. Upon concentration on the rotary evaporator white crystals precipitated from this solution. These were collected and washed 3 times with ice-cold $Et_2O$ to yield the pure product (177 mg, 81%). $^1H$ NMR (400 MHz, $CDCl_3$) δ 7.96 (d, J=8.2 Hz, 1H), 7.74 (d, J=8.4 Hz, 2H), 7.46 (d, J=7.6 Hz, 1H), 7.40 (s, 1H), 7.31-7.25 (m, 1H), 7.24-7.17 (m, 3H), 6.36-6.26 (m, 2H), 3.20 (br d, J=5.3 Hz, 1H), 3.04 (dd, J=9.0, 2.2 Hz, 1H), 2.83-2.66 (m, 3H), 2.53-2.45 (m, 1H), 2.45-2.40 (br m, 1H), 2.33 (s, 3H), 1.90 (dt, J=9.0, 2.5 Hz, 1H), 1.58-1.42 (m, 3H), 1.34-1.24 (m, 1H), 0.93-0.88 (m, 1H), 0.86 (t, J=7.4 Hz, 3H); $^{13}C$ NMR (126 MHz, $CDCl_3$) δ 144.7, 135.7, 135.3, 133.1, 132.7, 131.5, 129.9 (2C), 126.9 (2C), 124.5, 123.2, 123.0, 121.9, 119.6, 113.8, 57.7, 56.3, 56.2, 41.3, 31.7, 29.8, 27.4, 24.2, 21.6, 12.6; m/z calcd. for $C_{26}H_{30}N_2O_2S$=434.20, found=435.12.

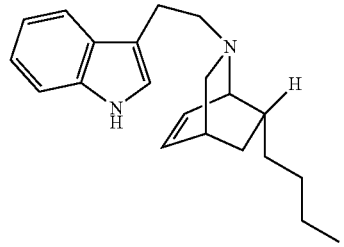 [SMILES: CCCCC1CC2C=CC1N(CCc1c[nH]c3ccccc13)C2]

endo-2-(2-(1H-indol-3-yl)ethyl)-7-butyl-2-azabicyclo[2.2.2]oct-5-ene (83): Prepared from 63b and 3-(2-bromoethyl)indole according to general procedure B. Purified by flash column chromatography (silica gel, hexanes:EtOAc=6:4 with 1% $NEt_3$). Pale yellow solid, 54% yield. $^1HNMR$ (400 MHz, $CDCl_3$) δ 7.99 (br s, 1H), 7.61 (d, J=7.8 Hz, 1H), 7.34 (d, J=8.1 Hz, 1H), 7.21-7.16 (m, 1H), 7.13-7.08 (m, 1H), 7.00 (d, J=2.0 Hz, 1H), 6.39 (t, J=7.2 Hz, 1H), 6.18-6.10 (m, 1H), 3.41 (s, 1H), 3.06 (d, J=9.5 Hz, 1H), 3.00-2.85 (m, 3H), 2.60-2.51 (m, 1H), 2.51 (s, 1H), 2.13 (dt, J=9.8, 2.5 Hz, 2H), 1.80 (ddd, J=12.1, 9.2, 2.7 Hz, 1H), 1.30-1.20 (m, 5H), 1.01-0.93 (m, 1H), 0.88 (t, J=6.8 Hz, 3H), 0.79 (ddd, J=7.5, 4.6, 2.5 Hz, 1H); $^{13}C$ NMR (101 MHz, $CDCl_3$) δ 136.2, 133.7, 130.1, 127.6, 121.9, 121.4, 119.2, 118.9, 114.7, 111.0, 58.9, 57.5, 54.2, 38.3, 35.7, 31.4, 30.8, 29.2, 24.4, 22.9, 14.09; m/z calcd. for $C_{21}H_{28}N_2$=308.22, found=308.86.

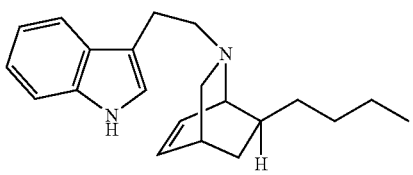 [SMILES: CCCCC1CC2C=CC1N(CCc1c[nH]c3ccccc13)C2]

exo-2-(2-(1H-indol-3-yl)ethyl)-7-butyl-2-azabicyclo[2.2.2]oct-5-ene (84): Prepared from 63a and 3-(2-bromoethyl)indole according to general procedure B. Purified by flash column chromatography (silica gel, hexanes:EtOAc=6:4 with 1% NEt$_3$). Pale yellow solid, 25% yield. $^1$H NMR (400 MHz, CDCl$_3$) δ 7.94 (br s, 1H), 7.60 (d, J=7.8 Hz, 1H), 7.34 (d, J=8.0 Hz, 1H), 7.16 (t, J=7.2 Hz, 1H), 7.12 (t, J=7.2 Hz, 1H), 7.03 (s, 1H), 6.40-6.26 (m, 2H), 3.27 (s, 1H), 3.15 (s, 1H), 2.97-2.74 (m, 3H), 2.57 (s, 1H), 2.45 (s, 1H), 1.99 (d, J=9.1 Hz, 1H), 1.63-1.45 (m, 3H), 1.30 (br d, J=3.1 Hz, 4H), 0.98-0.86 (m, 5H); $^{13}$C NMR (101 MHz, CDCl$_3$) δ 136.2, 132.8, 132.7, 127.7, 121.8, 121.5, 119.1, 118.9, 115.0, 111.0, 58.9, 56.4, 56.2, 39.2, 34.1, 31.6, 30.4, 29.8, 24.2, 23.0, 14.2; m/z calcd. for C$_{21}$H$_{28}$N$_2$=308.22, found=308.80.

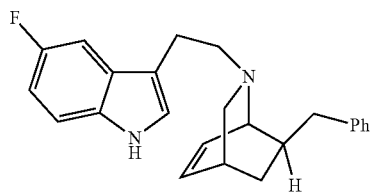 [SMILES: Fc1ccc2[nH]cc(CCN3CC4C=CC3C(Cc3ccccc3)C4)c2c1]

exo-7-benzyl-2-(2-(5-fluoro-1H-indol-3-yl)ethyl)-2-azabicyclo[2.2.2]oct-5-ene (85): Prepared from 64a and 3-(2-bromoethyl)-5-fluoroindole according to general procedure B. Purified by flash column chromatography (silica gel, hexanes:EtOAc=8:2). Pale yellow solid, 40% yield. $^1$H NMR (400 MHz, CDCl$_3$) δ 7.93 (br s, 1H), 7.29-7.24 (m, 2H), 7.17-7.08 (m, 4H), 7.01-6.91 (m, 3H), 6.34 (t, J=7.2 Hz, 1H), 6.21-6.15 (m, 1H), 3.22 (dd, J=9.0, 2.1 Hz, 1H), 2.99 (d, J=5.4 Hz, 1H), 2.86-2.73 (m, 5H), 2.54-2.46 (m, 2H), 2.01 (dt, J=9.0, 2.5 Hz, 1H), 1.73-1.64 (m, 1H), 1.57-1.47 (m, 1H), 1.04 (ddd, J=12.3, 4.7, 2.0 Hz, 1H); $^{13}$C NMR (100 MHz, CDCl$_3$) δ 157.7 (d, J=234.1 Hz), 141.9, 133.1, 132.7, 132.4, 129.1, 128.1, 128.0, 125.5, 123.5, 115.2, 111.6 (d, J=9.6 Hz), 110.1 (d, J=26.3 Hz), 103.7 (d, J=23.3 Hz), 58.8, 56.0, 55.3, 41.1, 39.8, 31.5, 29.8, 24.3; m/z calcd. for C$_{24}$H$_{25}$FN$_2$=360.20, found=360.93.

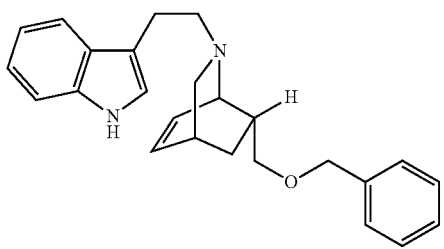 [SMILES: C1=CC2C(COCc3ccccc3)CC1CN2CCc1c[nH]c2ccccc12]

endo-2-(2-(1H-indol-3-yl)ethyl)-7-(benzyloxymethyl)-2-azabicyclo[2.2.2]oct-5-ene (86):
Compound 65b (73 mg, 0.20 mmol) was dissolved in dry DCM (1.6 mL) under argon and the solution was cooled to 0° C. Trimethylsilyl iodide (114 μl, 0.80 mmol) was then added and the mixture was stirred for 3 h at room temperature. The reaction was quenched with MeOH and concentrated to yield a foamy orange oil which was used for the next step without further purification. This orange oil was re-dissolved in dry DCE (1.2 mL) under argon, 3-indolylacetaldehyde (47 mg, 0.29 mmol), triethylamine (70 μl, 0.4 mmol), and sodium triacetoxyborohydride (83 mg, 0.39 mmol) were added, and the resulting orange mixture was left to stir for 3 h at room temperature The reaction was quenched with water (10 mL) and extracted with CHCl$_3$ (3×10 mL). The combined organics were dried over Na$_2$SO$_4$ and concentrated to yield an orange solid which was purified by flash column chromatography (silica gel, DCM:MeOH=19:1) to yield a pale yellow solid (46 mg, 0.12 mmol, 62% yield). 1H NMR (400 MHz, CDCl$_3$) δ 8.05 (br s, 1H), 7.61 (d, J=7.8 Hz, 1H), 7.37-7.28 (m, 6H), 7.20-7.15 (m, 1H), 7.14-7.09 (m, 1H), 6.99 (d, J=2.2 Hz, 1H), 6.38 (dd, J=10.8, 3.9 Hz, 1H), 6.16-6.09 (m, 1H), 4.55-4.44 (m, 2H), 3.71-3.66 (m, 1H), 3.14-3.05 (m, 3H), 2.98-2.86 (m, 3H), 2.65-2.56 (m, 2H), 2.55-2.49 (m, 1H), 2.14 (dt, J=9.7, 2.6 Hz, 1H), 1.75 (ddd, J=12.3, 9.5, 2.7 Hz, 1H), 0.73-0.63 (m, 1H); $^{13}$C NMR (101 MHz, CDCl$_3$) δ 138.7, 136.3, 133.6, 130.0, 128.3, 127.5, 127.4 (2C), 121.8, 121.4, 119.1, 118.9, 114.7, 111.0, 73.5, 72.7, 58.9, 54.6, 38.5, 31.0, 26.6 (2C), 24.5; m/z calcd. for C$_{25}$H$_{28}$N$_2$O=372.22, found=373.40.

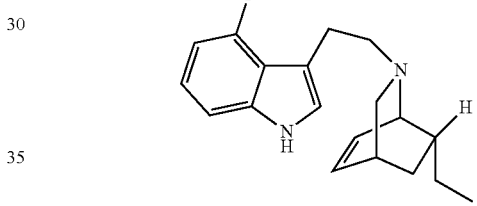

endo-7-ethyl-2-(2-(4-fluoro-1H-indol-3-yl)ethyl)-2-azabicyclo[2.2.2]oct-5-ene (87): Prepared from 8 and 3-(2-bromoethyl)-4-fluoroindole according to general procedure A. Purified by flash column chromatography (silica gel, hexanes:EtOAc=6:4 with 2% NEt$_3$). Pale yellow solid, 49% yield. $^1$HNMR (400 MHz, CDCl$_3$) δ 8.37 (br s, 1H), 7.06 (dt, J=7.7, 6.5 Hz, 2H), 6.92 (s, 1H), 6.72 (ddd, J=11.0, 7.5, 0.9 Hz, 1H), 6.38 (t, J=6.9 Hz, 1H), 6.19-6.11 (m, 1H), 3.47 (s, 1H), 3.07-2.92 (m, 3H), 2.90-2.82 (m, 1H), 2.61-2.55 (m, 1H), 2.50 (br s, 1H), 2.16 (dd, J=9.8, 2.5 Hz, 1H), 2.04 (br s, 1H), 1.78 (ddd, J=12.1, 9.2, 2.8 Hz, 1H), 1.22-1.11 (m, 1H), 1.05-0.96 (m, 1H), 0.85 (t, J=7.3 Hz, 3H), 0.81-0.75 (m, 1H); $^{13}$C NMR (100 MHz, CDCl$_3$) δ 156.9 (d, J=251.7 Hz), 138.8 (d, J=13.7 Hz), 133.3, 129.9, 121.9 (d, J=8.0 Hz), 121.4, 116.3, 113.0, 106.8 (d, J=3.0 Hz), 103.9 (d, J=13.1 Hz), 59.4, 56.7, 53.7, 39.8, 31.0, 30.3, 28.4, 25.2, 11.3; m/z calcd. for [M+H]$^+$ C$_{19}$H$_{24}$N$_2$F=299.1924, found=299.1924.

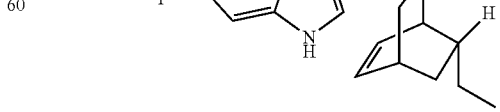

endo-7-ethyl-2-(2-(6-fluoro-1H-indol-3-yl)ethyl)-2-azabicyclo[2.2.2]oct-5-ene (88): Prepared from 8 and 3-(2- bromoethyl)-6-fluoroindole according to general procedure A. Purified by flash column chromatography (silica gel, hexanes:EtOAc=6:4 with 2% NEt$_3$). Pale yellow solid, 49% yield. $^1$H NMR (500 MHz, CDCl$_3$) δ 8.10 (br s, 1H), 7.49 (dd, J=8.6, 5.3 Hz, 1H), 7.01 (dd, J=9.7, 2.2 Hz, 1H), 6.96 (d, J=1.9 Hz, 1H), 6.87 (ddd, J=9.6, 8.8, 2.3 Hz, 1H), 6.38 (t, J=7.1 Hz, 1H), 6.17-6.10 (m, 1H), 3.44-3.39 (m, 1H), 3.03 (dd, J=9.7, 1.8 Hz, 1H), 2.95-2.82 (m, 3H), 2.57-2.54 (m, 1H), 2.51 (br s, 1H), 2.11 (ddd, J=8.5, 5.6, 2.9 Hz, 1H), 2.08-2.02 (m, 1H), 1.79 (ddd, J=12.1, 9.2, 2.8 Hz, 1H), 1.17 (dd, J=12.9, 5.7 Hz, 1H), 1.01 (dt, J=14.2, 7.5 Hz, 1H), 0.85 (t, J=7.4 Hz, 3H), 0.81-0.76 (m, 1H); $^{13}$C NMR (100 MHz, CDCl$_3$) δ 160.1 (d, J=236.2 Hz), 136.1 (d, J=12.4 Hz), 133.6, 130.0, 124.3, 121.6, 119.7 (d, J=13.5 Hz), 114.9, 107.9 (d, J=21.1 Hz), 97.3 (d, J=19.1 Hz), 58.8, 57.1, 54.2, 40.3, 31.4, 30.6, 28.7, 24.3, 11.6; m/z calcd. for [M+H]$^+$ C$_{19}$H$_{24}$N$_2$F=299.1924, found=299.1924.

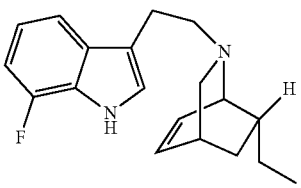 [SMILES: CCC1CC2C=CC1N(CCc1c[nH]c3c(F)cccc13)C2]

endo-7-ethyl-2-(2-(7-fluoro-1H-indol-3-yl)ethyl)-2-azabicyclo[2.2.2]oct-5-ene (89): Prepared from B8 and 3-(2-bromoethyl)-7-fluoroindole according to general procedure A. Purified by flash column chromatography (silica gel, hexanes:EtOAc=6:4 with 2% NEt$_3$). Pale yellow solid, 45% yield. $^1$H NMR (500 MHz, CDCl$_3$) δ 8.22 (br s, 1H), 7.35 (d, J=7.9 Hz, 1H), 7.03-6.97 (m, 2H), 6.87 (dd, J=11.2, 7.8 Hz, 1H), 6.39 (t, J=7.0 Hz, 1H), 6.18-6.11 (m, 1H), 3.47-3.41 (m, 1H), 3.05 (dd, J=9.7, 1.8 Hz, 1H), 2.97-2.85 (m, 3H), 2.59 (dt, J=9.4, 6.6 Hz, 1H), 2.54-2.49 (m, 1H), 2.13 (d, J=9.7 Hz, 1H), 2.09-2.04 (m, 1H), 1.79 (ddd, J=12.1, 9.2, 2.8 Hz, 1H), 1.23-1.15 (m, 1H), 1.07-0.98 (m, 1H), 0.86 (t, J=7.4 Hz, 3H), 0.82-0.77 (m, 1H); $^{13}$C NMR (101 MHz, CDCl$_3$) δ 149.6 (d, J=243.6 Hz), 133.9, 131.3 (d, J=5.4 Hz), 129.7, 124.5 (d, J=13.1 Hz), 122.2, 119.4 (d, J=6.1 Hz), 115.4, 114.7 (d, J=3.4 Hz), 106.7 (d, J=16.1 Hz), 58.7, 57.2, 54.2, 40.1, 31.3, 30.4, 28.6, 24.2, 11.5; m/z calcd. for [M+H]$^+$ C$_{19}$H$_{24}$N$_2$F=299.1924, found=299.1913.

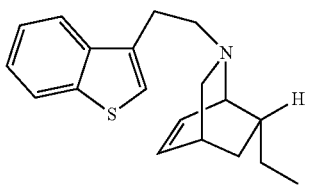 [SMILES: CCC1CC2C=CC1N(CCc1csc3ccccc13)C2]

endo-2-(2-(benzo[b]thiophen-3-yl)ethyl)-7-ethyl-2-azabicyclo[2.2.2]oct-5-ene (90): Prepared from 8 and 3-(2-bromoethyl)benzo[b]thiophene according to general procedure A. Purified by flash column chromatography (silica gel, hexanes:EtOAc=1:1). Pale yellow oil, 49% yield. $^1$H NMR (500 MHz, CDCl$_3$) δ 7.84 (d, J=7.8 Hz, 1H), 7.77 (d, J=7.7 Hz, 1H), 7.41-7.31 (m, 2H), 7.13 (s, 1H), 6.40 (t, J=7.2 Hz, 1H), 6.17-6.12 (m, 1H), 3.44-3.37 (m, 1H), 3.09-2.89 (m, 4H), 2.66-2.58 (m, 1H), 2.55-2.50 (m, 1H), 2.11 (dt, J=9.7, 2.7 Hz, 1H), 2.06-2.04 (br m, 1H), 1.80 (ddd, J=12.1, 9.2, 2.8 Hz, 1H), 1.24-1.14 (m, 1H), 1.06-0.97 (m, 1H), 0.86 (t, J=7.4 Hz, 3H), 0.83-0.77 (m, 1H); $^{13}$C NMR (101 MHz, CDCl$_3$) δ 140.3, 139.1, 135.0, 133.6, 130.0, 124.1, 123.8, 122.8, 121.7, 121.5, 57.8, 57.8, 54.3, 40.5, 31.4, 30.5, 28.7, 27.8, 11.6; m/z calcd. for [M+H]$^+$ C$_{19}$H$_{24}$NS=298.1629, found=298.1637.

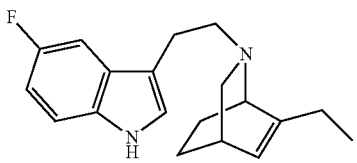 [SMILES: CCC1=CC2CCC1N(CCc1c[nH]c3ccc(F)cc13)C2]

6-ethyl-2-(2-(5-fluoro-1H-indol-3-yl)ethyl)-2-azabicyclo[2.2.2]oct-5-ene (91): Prepared from 68 and 3-(2-bromoethyl)-5-fluoroindole by a modification of general procedure A using 8 eq. of Na$_2$CO$_3$ as base in the alkylation step. Purified by repeated flash column chromatography (silica gel, 50 to 100% Et$_2$O in hexanes (first column) then 50 to 100% EtOAc in hexanes+3% Et$_3$N (second column)). Pale-yellow solid, 16% yield. $^1$H NMR (400 MHz, CDCl$_3$) δ 8.09 (br d, J=26.3 Hz, 1H), 7.23 (d, J=8.3 Hz, 2H), 7.03 (s, 1H), 6.92 (t, J=8.9 Hz, 1H), 5.93 (d, J=5.6 Hz, 1H), 3.30 (s, 1H), 3.09 (d, J=9.0 Hz, 1H), 2.95-2.73 (m, 3H), 2.55-2.39 (m, 2H), 2.14-2.00 (m, 3H), 1.56 (t, J=10.3 Hz, 1H), 1.33-1.21 (m, 3H), 1.03 (t, J=7.4 Hz, 3H); m/z calcd. for C$_{19}$H$_{23}$FN$_2$=298.18, found=299.00.

EXAMPLE 13

GDNF In-Situ ELISA in C6 Glioma Cells

The GDNF E$_{max}$ Immunoassay System from Promega (Madison, Wis.) was used to determine small molecule induced GDNF release from C6 glioma cells (ATCC, Manassas, Va.) with the following protocol. A 96-well ELISA plate was sterilized with UV for 30 minutes. The plate was coated with 100 µl/well of the anti-GDNF monoclonal antibody solution in carbonate coating buffer prepared per the manufacturer's instructions, and incubated overnight at 4° C. The antibody coating buffer was removed from the plate, which was then blocked according to the instructions in the kit. The plate was then incubated with 200 µl/well complete growth medium (95% DMEM, 5% FBS, 1% penicillin/streptomycin) for 2×1 h at rt to remove residue of the blocking buffer. After these washes were complete, fresh culture media was added to the wells. C6 cells were seeded at a density of 11,000 cells/well, with a total volume of approximately 150 µl in each well. The plate was incubated at 37° C. in an atmosphere containing 5% CO$_2$. After 24 hours, complete growth medium was replaced with low serum medium (98.5% DMEM, 0.5% FBS, 1% penicillin/streptomycin) and the plate was incubated overnight for cellular synchronization. On the following day, cells were treated with experimental compounds for the indicated time. We used 10 µM concentrations of the tested compounds during a 48-hour incubation. Simultaneously with initiation of treatment, cells were removed from pre-treatment control wells with 5×200 µL washes of TBST (to control for basal GDNF release before the treatment period), and low-serum medium was added to these wells. 6 hours prior to stopping treatment with experimental compounds, the GDNF standard was added to the plate per the manufacturer's instructions. To terminate the treatment, the plate was washed extensively with 200 µl/well TBST washing buffer 5 times, which removed the cells. GDNF release for each well was measured according to GDNF $E_{max}$ Immunoassay system instructions, and a plate reader was used to measure absorbance at 450 nm. Total GDNF release is calculated from the standard curve using Microsoft Excel. The listed values in Table 1 are presented as fold-increase of release of GDNF over control release of GDNF, corrected for pre-treatment release by subtracting from all values the mean amount of GDNF released in pre-treatment control wells. Statistical significance was determined using the Student's t-test.

TABLE 1

| Compound # | Structure | Fold-Increase of GDNF Concentration |
|---|---|---|
| 10a | 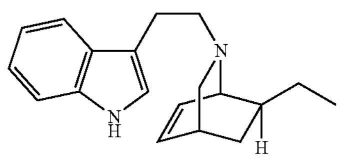 [SMILES: CCC1CC2C=CC1N(CCc1c[nH]c3ccccc13)C2] | 3.2 ± 0.2 |
| 10b | 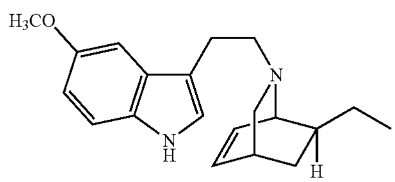 [SMILES: CCC1CC2C=CC1N(CCc1c[nH]c3ccc(OC)cc13)C2] | 2.2 ± 0.2 |
| 12a | 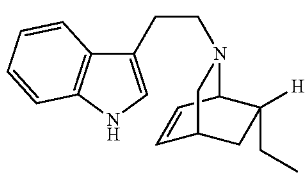 [SMILES: CCC1CC2C=CC1N(CCc1c[nH]c3ccccc13)C2] | 2.0 ± 0.1 |
| 12b | 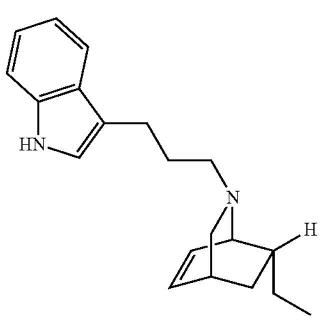 [SMILES: CCC1CC2C=CC1N(CCCc1c[nH]c3ccccc13)C2] | 1.5 ± 0.0 |
| 12c | 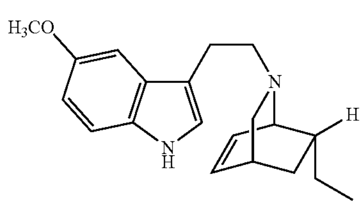 [SMILES: CCC1CC2C=CC1N(CCc1c[nH]c3ccc(OC)cc13)C2] | 2.1 ± 0.1 |

TABLE 1-continued

| Compound # | Structure | Fold-Increase of GDNF Concentration |
|---|---|---|
| 12d | 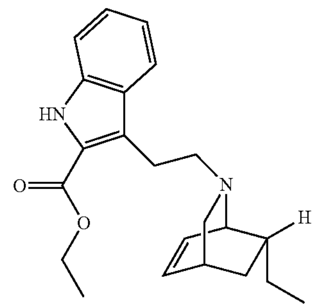 [SMILES: CCOC(=O)c1[nH]c2ccccc2c1CCN1CC2C=CC1C(CC)C2] | 1.5 ± 0.0 |
| 12f | 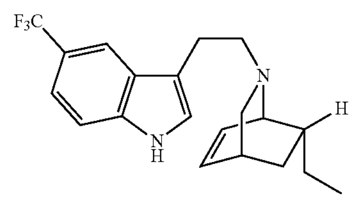 [SMILES: CCC1CC2C=CC1N(CCc1c[nH]c3ccc(C(F)(F)F)cc13)C2] | 2.0 ± 0.0 |
| 12g | 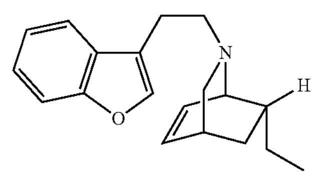 [SMILES: CCC1CC2C=CC1N(CCc1coc3ccccc13)C2] | 2.9 ± 0.1 |
| 12h | 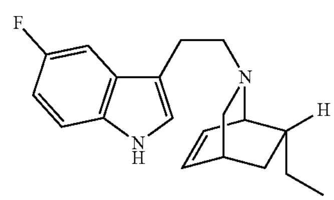 | 3.1 ± 0.2 |
| 12l | 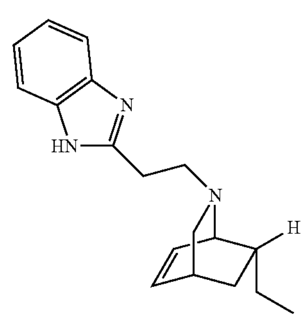 [SMILES: CCC1CC2C=CC1N(CCc1nc3ccccc3[nH]1)C2] | 1.5 ± 0.0 |
| 13a | 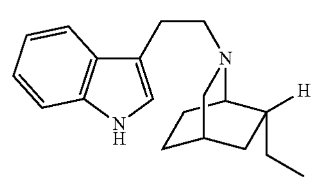 [SMILES: CCC1CC2CCC1N(CCc1c[nH]c3ccccc13)C2] | 2.0 ± 0.0 |

TABLE 1-continued

| Compound # | Structure | Fold-Increase of GDNF Concentration |
|---|---|---|
| 13b | (5-fluoroindole with azabicyclic ethyl substituent) | 2.0 ± 0.0 |
| 18a | (indole with azabicyclic alkene) | 1.6 ± 0.0 |
| 18b | (indole with azabicyclic alkene, isomer) | 1.6 ± 0.1 |
| 21 | (indole with azabicyclic ethyl ester) | 1.0 ± 0.0 |
| 22 | (indole with azabicyclic diester) | 2.0 ± 0.0 |

EXAMPLE 14

Treatment of C6 Glioma Cells and Measurement of GDNF Release by Conventional ELISA Conventional ELISAs were used to determine compound-induced increases of GDNF concentration in conditioned media of C6 glioma cells, and have afforded increased sensitivity compared to in-situ ELISA in our hands. C6 cells were purchased from ATCC (Manassas, Va.) at passage 37 and were used between passages 41-46. This requirement for a narrow range of passages is based on an observed decrease in magnitude of GDNF release with age of the cell line, and is consistent with reported behavior of C6 cells. All incubations were conducted at 37° C. in a humidified atmosphere containing 5% $CO_2$. GDNF release was measured for each compound in 3 independent experiments. Briefly, C6 cells were seeded into sterile 12-well culture plates (Falcon) at a density of 300,000 cells per well and were recovered for 24 h in 1mL complete growth medium (94% high glucose DMEM, 5% FBS, 1% penicillin/streptomycin). Wells were then washed with 1mL sterile DPBS and were incubated for an additional 24 h with 0.5 mL low-serum medium (98.5% high glucose DMEM, 0.5% FBS, 1% penicillin/streptomycin). On the following day, experimental compounds or DMSO vehicle control were added each to duplicate wells in an additional 0.5 mL of low-serum medium. The final concentration of each compound was 10 µM in 1mL low-serum medium containing 0.1% DMSO. Plates were incubated with compounds and vehicle control for 48 h. Conditioned media were then collected from each well and GDNF concentrations were measured in triplicate on 96-well ELISA plates using the GDNF $E_{max}$ Immunoassay System from Promega (Madison, Wis.) according to the manufacturer's instructions. A Bio-Tek H1MF plate reader (Burlington, Vt.) was used to measure absorbance from the resulting colorimetric reaction. Total GDNF release for each compound was calculated from the standard curve using Microsoft Excel. Data are normalized to the vehicle control and are thus presented as fold increase of GDNF concentration in experimental wells over that of the vehicle control. Each reported compound afforded a statistically significant increase of GDNF release over the DMSO control in each of three independent experiments conducted on separate days unless otherwise noted. Statistical significance within each experiment was determined by ANOVA followed by Tukey's post-hoc analysis using GraphPad Prism. Because of the naturally high variability of GDNF release values between experiments, data presented herein are intra-assay means from a representative experiment ±intra-assay standard error of the mean (SEM) calculated from biological replicates. Cytotoxicity for each compound was below 20% as measured by LDH levels in conditioned media (Cytotox 96, Promega).

All results (Table 2) represent fold-increase of GDNF release by C6 glioma cells treated with the indicated compound for 48 hours, normalized to the vehicle control. Results are presented from a representative experiment and were determined to be statistically significant (ANOVA) compared to the vehicle control. All compounds induced a statistically significant increase of GDNF in each of 3 independent experiments unless otherwise indicated. 88 was tested twice and afforded statistically significant results in both trials.

TABLE 2

| Compound # | Structure | GDNF Increase ± SEM (fold/vehicle control) |
|---|---|---|
| 74 | (indole with azabicyclic propyl substituent) | 7.11 ± 1.17 |

TABLE 2-continued

| Compound # | Structure | GDNF Increase ± SEM (fold/vehicle control) |
|---|---|---|
| 84 | 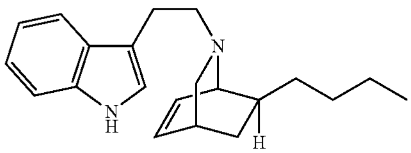 [SMILES: CCCCC1CC2C=CC1N(CCc1c[nH]c3ccccc13)C2] | 12.65 ± 0.66 |
| 77 | 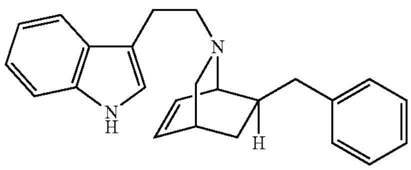 [SMILES: C1=CC2C(Cc3ccccc3)CC1CN2CCc1c[nH]c2ccccc12] | 13.22 ± 0.08 |
| 80 | 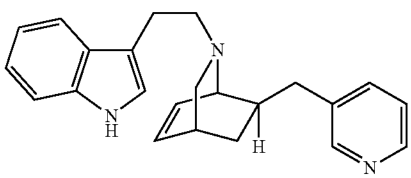 [SMILES: C1=CC2C(Cc3cccnc3)CC1CN2CCc1c[nH]c2ccccc12] | 7.02 ± 1.31 |
| 81 | 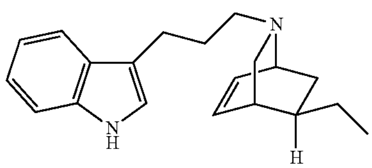 [SMILES: CCC1CC2C=CC1CN2CCCc1c[nH]c2ccccc12] | 12.55 ± 0.05 |
| 70 | 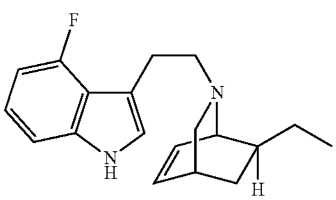 [SMILES: CCC1CC2C=CC1N(CCc1c[nH]c3cccc(F)c13)C2] | 15.75 ± 0.65 |
| 72 | 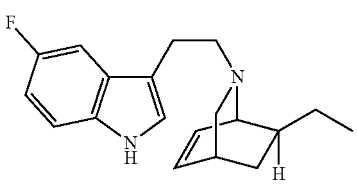 [SMILES: CCC1CC2C=CC1N(CCc1c[nH]c3ccc(F)cc13)C2] | 16.23 ± 0.41 |
| 71 | 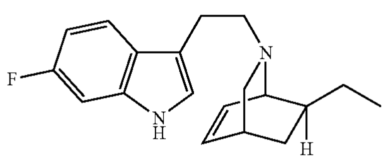 [SMILES: CCC1CC2C=CC1N(CCc1c[nH]c3cc(F)ccc13)C2] | 16.49 ± 0.30 |
| 69 | 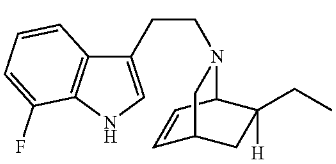 | 12.13 ± 0.01 |
| 79 | 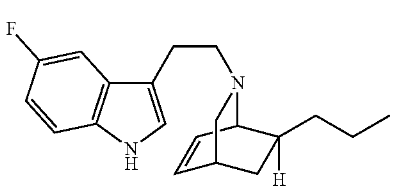 [SMILES: CCCC1CC2C=CC1N(CCc1c[nH]c3ccc(F)cc13)C2] | 14.55 ± 0.21 |

TABLE 2-continued
| Compound # | Structure | GDNF Increase ± SEM (fold/vehicle control) |
|---|---|---|
| 85 | 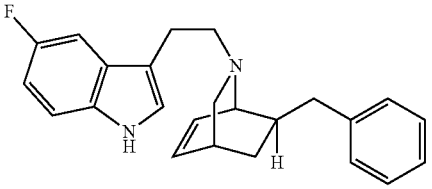 [SMILES: Fc1ccc2[nH]cc(CCN3CC4C=CC3C(Cc3ccccc3)C4)c2c1] | 13.23 ± 2.03 |
| 73 | 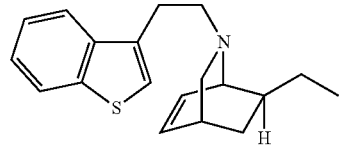 [SMILES: CCC1CC2C=CC1N(CCc1csc3ccccc13)C2] | 9.87 ± 0.22 |
| 75 | 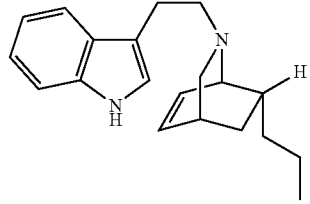 [SMILES: CCCC1CC2C=CC1N(CCc1c[nH]c3ccccc13)C2] | 14.77 ± 0.85 |
| 83 | 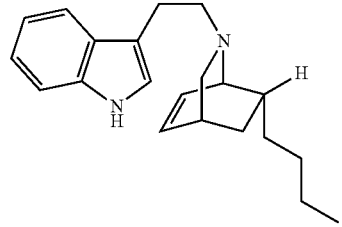 [SMILES: CCCCC1CC2C=CC1N(CCc1c[nH]c3ccccc13)C2] | 12.84 ± 0.50 |
| 76 | 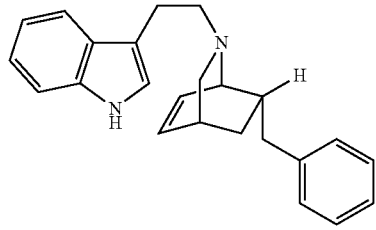 [SMILES: C1=CC2C(Cc3ccccc3)CC1CN2CCc1c[nH]c2ccccc12] | 12.80 ± 0.85 |
| 86 | 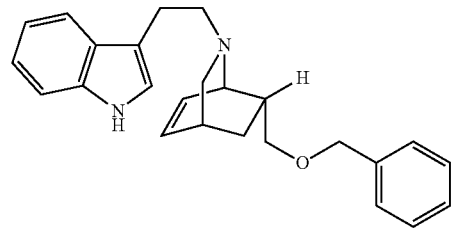 [SMILES: C1=CC2C(COCc3ccccc3)CC1CN2CCc1c[nH]c2ccccc12] | 13.82 ± 2.01 |
| 87 | 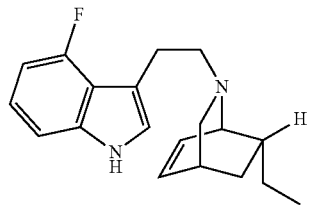 [SMILES: CCC1CC2C=CC1N(CCc1c[nH]c3cccc(F)c13)C2] | 10.87 ± 0.84 |

TABLE 2-continued

| Compound # | Structure | GDNF Increase ± SEM (fold/vehicle control) |
|---|---|---|
| 88 | 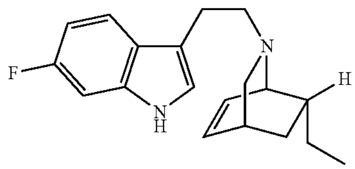 [SMILES: CCC1CC2C=CC1N(CCc1c[nH]c3cc(F)ccc13)C2] | 16.03 ± 1.66 |
| 89 | 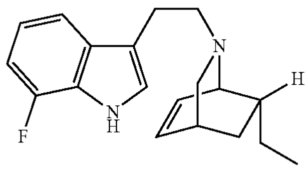 [SMILES: CCC1CC2C=CC1N(CCc1c[nH]c3c(F)cccc13)C2] | 14.71 ± 0.11 |
| 78 | 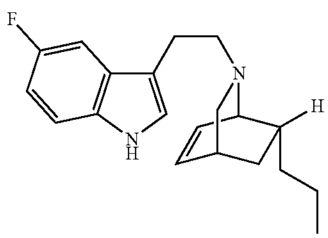 [SMILES: CCCC1CC2C=CC1N(CCc1c[nH]c3ccc(F)cc13)C2] | 14.39 ± 0.51 |
| 90 | 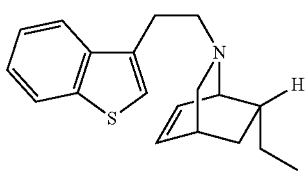 [SMILES: CCC1CC2C=CC1N(CCc1csc3ccccc13)C2] | 11.86 ± 0.01 |
| 91 | 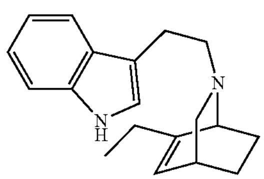 [SMILES: CCC1=CC2CCC1N(CCc1c[nH]c3ccccc13)C2] | 13.61 ± 0.62 |
| 82 | 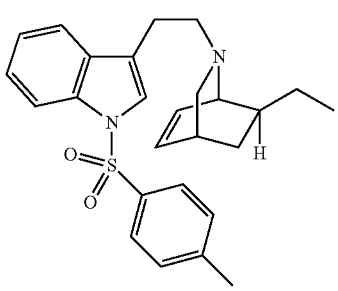 [SMILES: CCC1CC2C=CC1N(CCc1cn(S(=O)(=O)c3ccc(C)cc3)c3ccccc13)C2] | 13.56 ± 1.41 |

EXAMPLE 15

GDNF Releasing Potency Assay

Four compounds were selected for determination of GDNF releasing potency. The $EC_{50}$ value (Table 3) is defined as the concentration of the compound at which 50% of maximal GDNF release is obtained. The C6 cells were incubated with the selected compounds over a range of concentrations (0.1, 1, 5, 10, 20, 30 and 50 uM for each compound) and the amount of released GDNF at each concentration was via examing the dose-dependent release. A dose-response curve was constructed and the $EC_{50}$ value was obtained by fitting this curve using GraphPad Prism software.

TABLE 3

| Compound # | Structure | GDNF Release EC$_{50}$ (µM) |
|---|---|---|
| 10a | 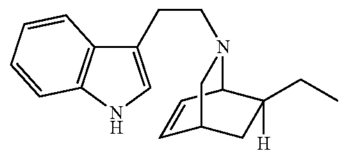 [SMILES: CCC1CC2C=CC1N(CCc1c[nH]c3ccccc13)C2] | 10.2 ± 0.3 |
| 12a | 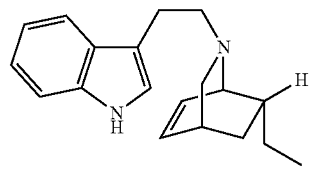 [SMILES: CCC1CC2C=CC1N(CCc1c[nH]c3ccccc13)C2] | 18.2 ± 0.2 |
| 12h | 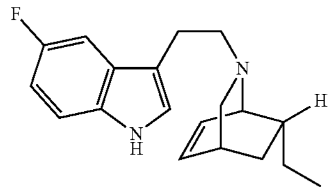 [SMILES: CCC1CC2C=CC1N(CCc1c[nH]c3ccc(F)cc13)C2] | 3.3 ± 0.1 |
| 12g | 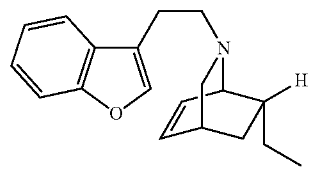 | 3.6 ± 0.1 |

Discussion

GDNF (Glial cell line-Derived Neurotrophic Factor) is essential for growth, development and plasticity of dopamine and motor neurons as well as other brain cell populations. In the brain, GDNF is released by both neurons and glia cells. On the basis of the trophic and repair effects GDNF has on neural cells, it is considered a potential therapeutic agent for several neurological disorders. However, GDNF is a protein and thus not readily administered to the brain. Ibogaine, a natural alkaloid and GDNF inducer, is not clinically useful due to side effects. Consequently, new inducers of GDNF release are needed.

GDNF inducers are promising drug targets as potential therapeutics, most notably in the context of, among others, Parkinson's disease, neuropathic pain, depression and substance use disorders. The isoquinuclidine compounds described in Examples 1-5 (Table 1) show up to a 3.2 fold increase in release of GDNF over the untreated control as measured by in-situ ELISA. Table 2 shows compounds that increase GDNF levels in C6 conditioned media by up to 16.49 fold over the untreated control as measured by the conventional ELISA protocol described in Example 14. This general increase in GDNF release compared to that measured by in-situ ELISA (Table 1) is a consequence of increased sensitivity of conventional ELISA in these experiments. Compound 12h has an EC$_{50}$ value of 3.3 µM while compound 12g has an EC$_{50}$ value of 3.3 µM in a GDNF releasing potency assay (Table 3). Therefore, the compounds of the present invention are inducers of GDNF and may be used to treat a variety of diseases, including, among others, Parkinson's disease, neuropathic pain, depression and substance use disorders.

An additional aspect of the invention provides synthetic methods and chemical intermediates that may be used to encompass chemical space about the isoquinulidine core structure. Additional compounds, which are synthesized according to the schemes in FIGS. 7-12, are expected to function analogously to the compounds disclosed in Tables 1 and 2. Additional compounds, which are synthesized according to the method described in the schemes of FIGS. 1-19, are expected to function analogously to the compounds disclosed in Tables 1, 2 and 3.

REFERENCES

Airaksinen, M. S. and Saarma, M. (2002) The GDNF Family: Signaling, Biological Functions and Therapeutic Value, Nature Rev. Neurosci. 3, 383-394.

Buechi, G.; Mak, C-P. (1977) Nitro olefination of indoles and some substituted benzenes with 1-dimethylamino-2-nitroethylene, J. Org. Chem. 42, 1784-1786.

Bolaños, C. A.; Nestler, E. J. (2004) Neurotrophic Mechanisms in Drug Addiction, NeuroMol. Med. 5, 69-83.

Borne, R. F.; Clark, C. R.; Holbrook, J. M. (1973) 2-Azabicyclo[2.2.2.]octane derivatives as conformational analogs of local anesthetics, J. Med. Chem. 16, 853-856.

Boucher, T. J.; Okuse, K.; Bennett, D. L. H.; Munson, J. B.; Wood, J. N.; McMahon, S. B. (2000) Potent Analgesic Effects of GDNF in Neuropathic Pain States, Science 290, 124-127.

Campos, K. R.; Woo, J. C. S.; Lee, S.; Tillyer, R. D. (2004) A General Synthesis of Substituted Indoles from Cyclic Enol Ethers and Enol Lactones, Org. Lett. 6, 79-82.

Carnicella, S.; Kharazia, V.; Jeanblanc, J.; Janak, P. H.; Ron, D. (2008) GDNF is a Fast-acting Potent Inhibitor of Alcohol Consumption and Relapse, Proc. Natl. Acad. Sci. 105, 8114-8119.

Carnicella, S.; He, D.-Y.; Yowell, Q. V.; Glick, S. D.; Ron, D. (2010) Noribogaine, but not 18-MC, Exhibits Similar Actions as Ibogaine on GDNF Expression and Ethanol Self-Administration, Addiction Biol. 15, 424-433

Cava, M. P.; Wilkins Jr., C.; Dalton, D. R.; Bessho, K. (1965) New Isoquinuclidine Synthesis. A New Route to dl-Dioscorone, J. Org. Chem. 30, 3772-3774

Cowart, M. et al. (2004) Discovery of 2-(4-Pyridin-2-ylpiperazin-1-ylmethyl)-1H-benzimidazole (ABT-724), a Dopaminergic Agent with a Novel Mode of Action for the Potential Treatment of Erectile Dysfunction, J. Med. Chem. 47, 3853-3864.

Feldman, P. L.; Rapoport, H. (1986) Convenient Synthesis of 6-Methoxyindole and 6-Methoxytryptophyl Bromide, Synthesis, 735-737.

Fowler, F. K. (1972) Synthesis of 1,2- and 1,4-dihydropyridines, J. Org. Chem. 37, 1321-1323.

He, D.-Y.; McGough, N. N. H.; Ravindranathan, A.; Jeanblanc, J.; Logrip, M. L.; Phamluong, K.; Janak, P. H.; Ron, D. (2005) Glial Cell Line-Derived Neurotrophic Factor Mediates the Desirable Action of the Anti-Addiction Drug Ibogaine Against Alcohol Consumption, J. Neurosci. 25, 619-628.

Kozikowski, A. P.; Gaisina, I. N.; Yuan, H.; Petukhov, P. A.; Blond, S. Y.; Fedolak, A.; Caldarone, B.; McGonigle, P. (2007) J. Am. Chem. Soc. 129, 8328-8332.

Krow, G. R.; Shaw, D. A.; Lynch, B.; Lesler, W.; Szczepanski, S. W.; Raghavachari, R. (1988) Regioselective synthesis of isoquinuclidin-6-ones. Synthesis of an ibogamine intermediate, J. Org. Chem. 53, 2258-2262.

Mariano, P. S.; Dunaway-Mariano, D.; Huesmann, P. L. (1979) Amino-Claisen rearrangements of N-vinylisoquinuclidines in novel approaches to the synthesis of hydroisoquinolines and hydrophenanthridines, J. Org. Chem. 44, 124-133.

Mewshaw, R. E.; Zhou, D.; Zhou, P.; Shi, X.; Hornby, G.; Spangler, T.; Scerni, R.; Smith, D.; Schechter, L. E.; Andree, T. H. (2004) J. Med. Chem. 47, 3823-3842.

Messer, C. J.; Eisch, A. J.; Carlezon, W. A.; Whistler, K.; Shen, L.; Wolf, D. H.; Westphal, H.; Collins, F.; Russell, D. S.; Nestler, E. J. (2000) Role of GDNF in Biochemical and Behavioral Adaptations to Drugs of Abuse, Neuron 26, 247-257.

Molander, G. A.; O. Argintaru, A.; Aron, I.; Dreher, S. D. (2010) Org. Lett. 12, 5783-5785.

Nakano, H.; Osone, K.; Takeshita, M.; Kwon, E.; Seki, C.; Matsuyama, H.; Takano, N. and Kohari, Y. (2010) Chem. Commun. 46, 4827.

Sugawara, S. et al. Proc. Nat. Acad. Sci. (2009) 106, 5430-5435.

Takebayashi, M.; Hisaoka, K.; Nishida, A.; Tsuchioka, M.; Miyoshi, I.; Kozuru, T.; Hisaka, S.; Okamoto, Y.; Shinno, H.; Morinobu, S.; Yamawaki, S. (2006) Decreased Level of Whole Blood GDNF in Remitted Patients with Mood Disorders, Int. J. Neuropsychopharm. 9, 607-612.

Tomaszewski, Z.; Johnson, M. P.; Huang, X.; Nichols, D. E. (1992) J. Med. Chem. 35, 2061-2064.

Trost, B.; Genet, J. P. (1976) Palladium catalyzed cyclizations to alkaloid skeletons. Facile synthesis of desethylibogamine, J. Am. Chem. Soc. 98, 8516-8517

Trupp, M.; Belluardo, N.; Funakoshi, H.; Ibáñez, C. F. (1997) Complementary and Overlapping Expression of Glial Cell Line-Derived Neurotrophic Factor (GDNF), c-ret Proto-Oncogene, and GDNF Receptor-α Indicates Multiple Mechanisms of Trophic Actions in the Adult Rat CNS, J. Neurosci. 17, 3554-3567.

Vega, A. M.; Martinez, M. T.; Palop, J. A.; Mateo, J. M.; Fernández-Alvarez, E. (1981) J. Heterocyclic Chem. 18, 889-892.

Woodward, R. B.; Bader, F. E.; Bickel, H.; Frey, A. J.; Kierstead, R. W. (1958) Tetrahedron, 2, 1-57.

What is claimed is:

1. A compound of the structure:

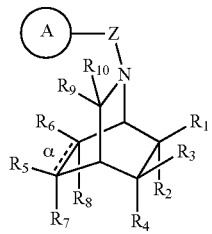

wherein
A is a ring structure, with or without substitution;
Z is present or absent and when present is

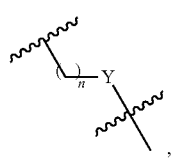

wherein
n is 0, 1, 2, 3, or 4;
Y is —$CH_2$—;

$R_1$ is H and $R_2$ is substituted or unsubstituted alkyl, substituted or unsubstituted aryl, substituted or unsubstituted heteroalkyl, substituted or unsubstituted heteroaryl, unsubstituted hydroxyl, amino, or amide, or $R_2$ is H and $R_1$ is substituted or unsubstituted alkyl, substituted or unsubstituted aryl, substituted or unsubstituted heteroalkyl, substituted or unsubstituted heteroaryl, unsubstituted hydroxyl, amino, or amide;

$R_3$ and $R_4$ are independently H, substituted or unsubstituted alkyl, substituted or unsubstituted aryl, substituted or unsubstituted heteroalkyl, substituted or unsubstituted heteroaryl, hydroxyl, amino, ester or amide;

$R_5$ and $R_6$ are independently H, substituted or unsubstituted alkyl, substituted or unsubstituted aryl, substituted or unsubstituted heteroalkyl, substituted or unsubstituted heteroaryl, hydroxyl, amino, ester or amide;

α represents a bond, which is present or absent and when α is present, then $R_7$ and $R_8$ are absent;

$R_7$ and $R_8$ are present when α is absent and $R_5$ and $R_7$ combine to form a carbonyl or $R_6$ and $R_8$ combine to form a carbonyl;

$R_9$ and $R_{10}$ are each hydrogen or combine to form a carbonyl; and when α is present, Z is

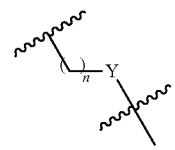

where n=1, Y is —$CH_2$—, A is unsubstituted indole attached at the 3-position of the indole, $R_3$, $R_4$, $R_5$, $R_6$, $R_9$ and $R_{10}$ are each H, and one of $R_1$ or $R_2$ is H, then the other one of $R_1$ or $R_2$ is other than H or ethyl, wherein the ring structure A is an indole, or a pharmaceutically acceptable salt, diastereomer, or enantiomer thereof.

2. The compound of claim 1, wherein the ring structure A is,

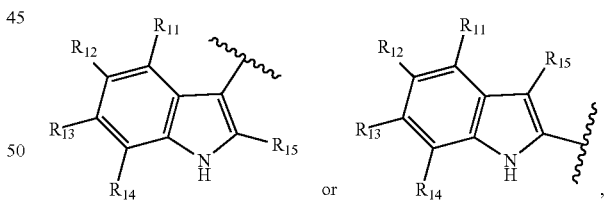

wherein $R_{11}$, $R_{12}$, $R_{13}$, $R_{14}$ and $R_{15}$ are each independently H, alkyl, aryl, heteroalkyl, heteroaryl, ester, or halide, each with or without substitution, or a pharmaceutically acceptable salt, diastereomer, or enantiomer thereof.

3. The compound of claim 2, wherein
wherein $R_{12}$, $R_{13}$ and $R_{15}$ are each independently H, F, Cl, Br, $CH_3$, $CF_3$, OMe, $OCF_3$, C(O)O$R_{16}$,
wherein $R_{16}$ is alkyl, and
$R_{11}$ and $R_{14}$ are each independently H, F, Cl, Br, $CH_3$, $CF_3$, OMe, $OCF_3$, C(O)O$R_{16}$,
wherein $R_{16}$ is alkyl
or a pharmaceutically acceptable salt, diastereomer, or enantiomer thereof.

4. The compound of claim 3,
wherein the ring structure A is,

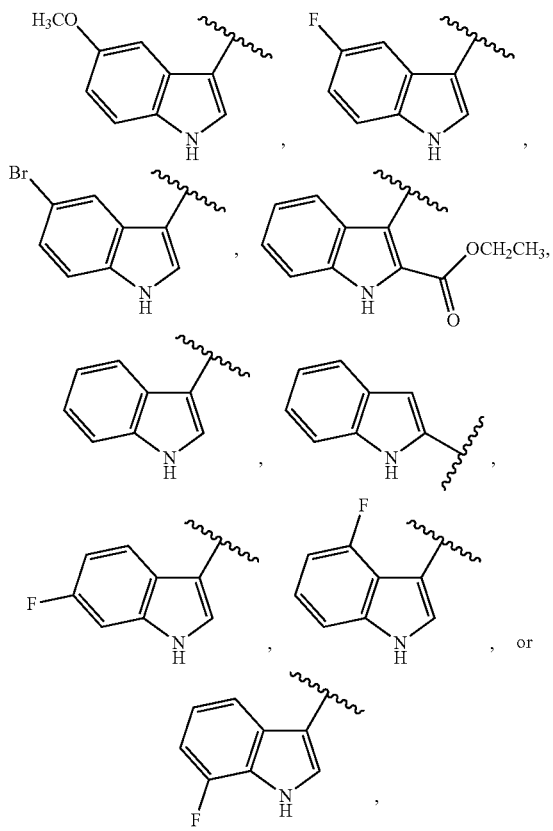

or a pharmaceutically acceptable salt, diastereomer, or enantiomer thereof.

5. The compound of claim 1,
wherein the ring structure A is

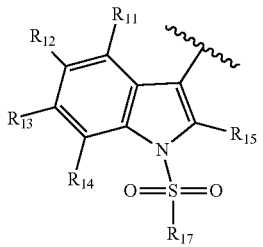

wherein $R_{11}$, $R_{12}$, $R_{13}$, $R_{14}$ and $R_{15}$ are each independently H, alkyl, aryl, heteroalkyl, heteroaryl, ester, or halide, each with or without substitution; and
$R_{17}$ is alkyl, aryl, heteroalkyl, or heteroaryl, each with or without substitution,
or a pharmaceutically acceptable salt, diastereomer, or enantiomer thereof.

6. The compound of claim 5, wherein
wherein $R_{11}$, $R_{12}$, $R_{13}$, $R_{14}$ and $R_{15}$ are each independently H, F, Cl, Br, $CH_3$, $CF_3$, OMe, $OCF_3$, $C(O)OR_{16}$, wherein $R_{16}$ is alkyl; and
$R_{17}$ is phenyl, benzyl, or tolyl,
or a pharmaceutically acceptable salt, diastereomer, or enantiomer thereof.

7. The compound of claim 6,
wherein the ring structure A is,

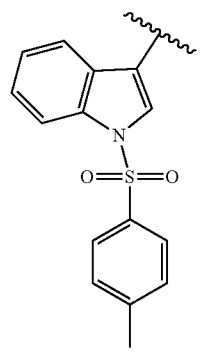

or a pharmaceutically acceptable salt, diastereomer, or enantiomer thereof.

8. The compound of claim 1,
wherein Z is

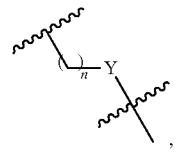

Y is —$CH_2$—, n=0, 1 or 2, $R_1$ is H and $R_2$ is alkyl or $CH_2$-aryl, or
wherein Z is

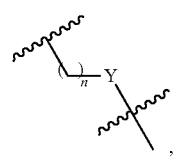

Y is —$CH_2$—, n=0, 1 or 2, $R_2$ is H and $R_1$ is alkyl or $CH_2$-aryl,
wherein the alkyl and aryl are each unsubstituted,
or a pharmaceutically acceptable salt, diastereomer, or enantiomer thereof.

9. A compound of the structure:

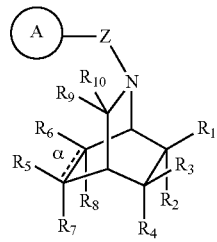

wherein
A is an indole, with or without substitution;
Z is present or absent and when present is

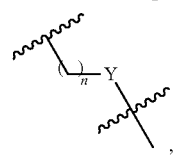

wherein
n is 0, 1, 2, 3, or 4;
Y is $CH_2$;
$R_1$, $R_2$, $R_3$, $R_4$, $R_5$ and $R_6$ are independently H, substituted or unsubstituted alkyl, substituted or unsubstituted aryl, substituted or unsubstituted heteroalkyl, substituted or unsubstituted heteroaryl, hydroxyl, amino, ester or amide;
α represents a bond, which is present or absent and when α is present, then $R_7$ and $R_8$ are absent;
$R_7$ and $R_8$ are present when α is absent and $R_5$ and $R_7$ combine to form a carbonyl or $R_6$ and $R_8$ combine to form a carbonyl;
$R_9$ and $R_{10}$ are each hydrogen or combine to form a carbonyl; and
when α is present, Z is

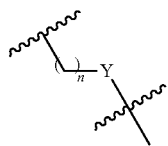

where n=1, Y is $-CH_2-$, A is unsubstituted indole attached at the 3-position of the indole, $R_3$, $R_4$, $R_5$, $R_6$, $R_9$ and $R_{10}$ are each H, and one of $R_1$ or $R_2$ is H, then the other one of $R_1$ or $R_2$ is other than H or ethyl, wherein Z is

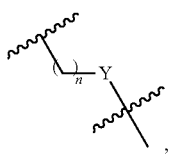

Y is $-CH_2-$, n=0, 1 or 2, $R_3$ is H and $R_4$ is alkyl, ester, or $CH_2$-aryl, or
wherein Z is

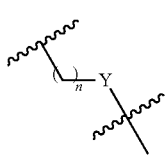

Y is $-CH_2-$, n=0, 1 or 2, $R_4$ is H and $R_3$ is alkyl, ester, or $CH_2$-aryl,
or a pharmaceutically acceptable salt, diastereomer, or enantiomer thereof.

10. The compound of claim 1,
wherein Z is

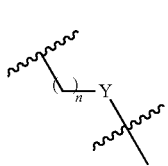

Y is $-CH_2-$, n=0, 1 or 2, $R_1$ is H and $R_2$ is $-CH_2$-aryl, $-CH_2$-heteroaryl, $-CH_2-O-CH_2$-aryl, $-CH_2-O-CH_2$-heteroaryl, or
wherein Z is

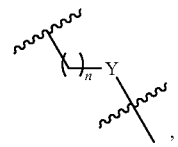

Y is $-CH_2-$, n=0, 1 or 2, $R_2$ is H and $R_1$ is $-CH_2$-aryl, $-CH_2$-heteroaryl, $-CH_2-O-CH_2$-aryl, $-CH_2-O-CH_2$-heteroaryl,
or a pharmaceutically acceptable salt, diastereomer, or enantiomer thereof.

11. The compound of claim 1,
wherein Z is

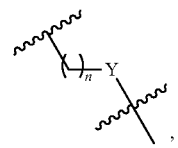

Y is $-CH_2-$, α is absent, n=1 or 2, $R_6$ and $R_8$ combine to form a $=O$, and $R_5$ and $R_7$ are independently H, alkyl, ester, or $CH_2$-aryl,
or a pharmaceutically acceptable salt, diastereomer, or enantiomer thereof.

12. The compound of claim 1,
wherein Z is

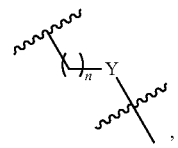

Y is $-CH_2-$, α is absent, n=1 or 2, $R_5$ and $R_7$ combine to form a $=O$, and $R_6$ and $R_8$ are independently H, alkyl, ester, or $CH_2$-aryl,
or a pharmaceutically acceptable salt, diastereomer, or enantiomer thereof.

13. The compound of claim 1,
wherein Z is

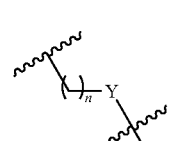

Y is $-CH_2-$, α is present, n=1 or 2, $R_5$ and $R_6$ are independently H, alkyl, ester, or $CH_2$-aryl,
or a pharmaceutically acceptable salt, diastereomer, or enantiomer thereof.

14. The compound of claim 1, wherein the structure is
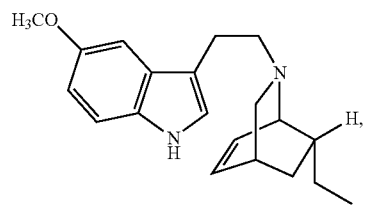
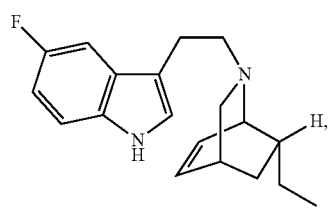
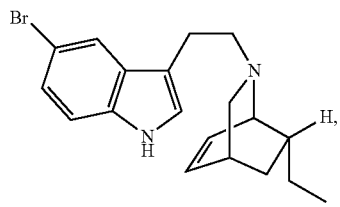
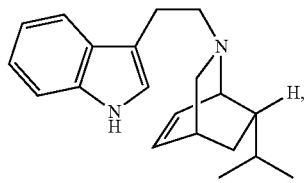
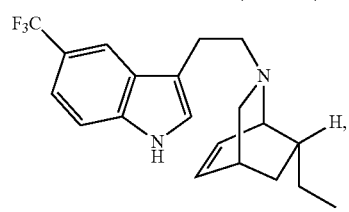
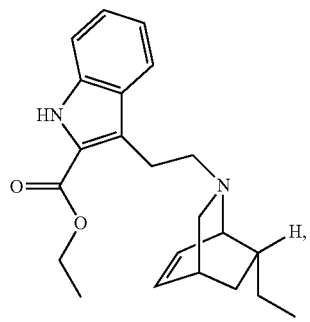
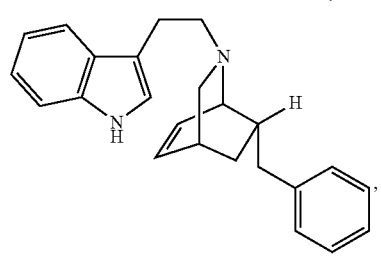
-continued
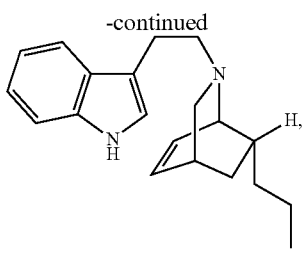
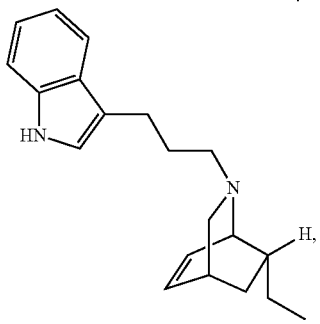
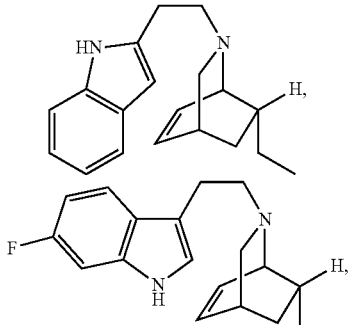
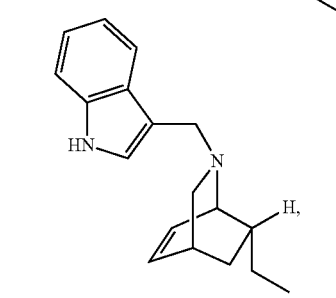
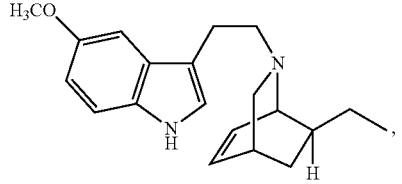
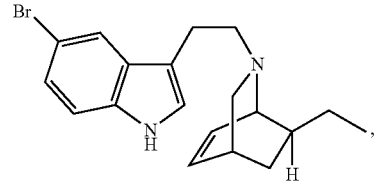

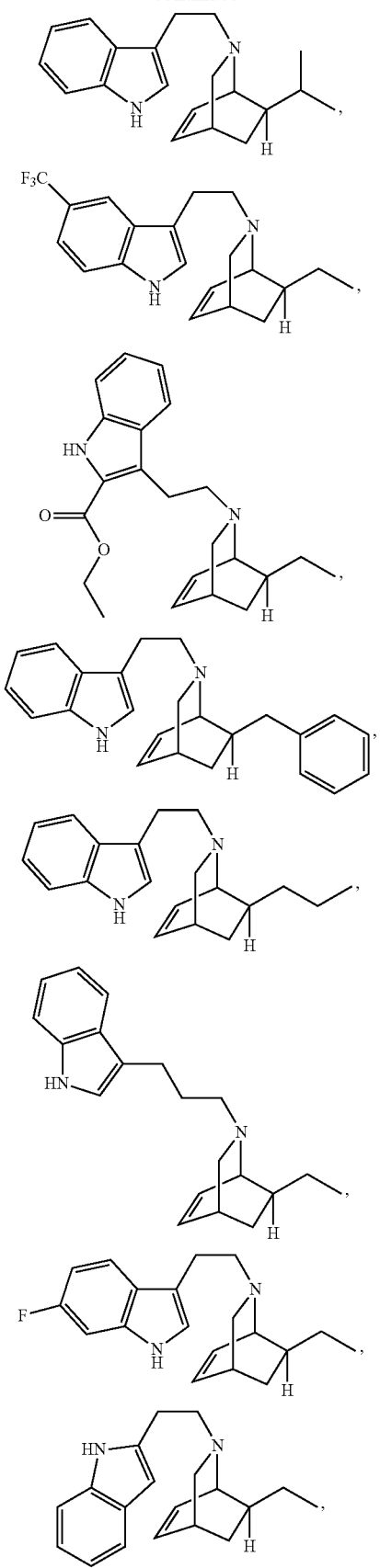
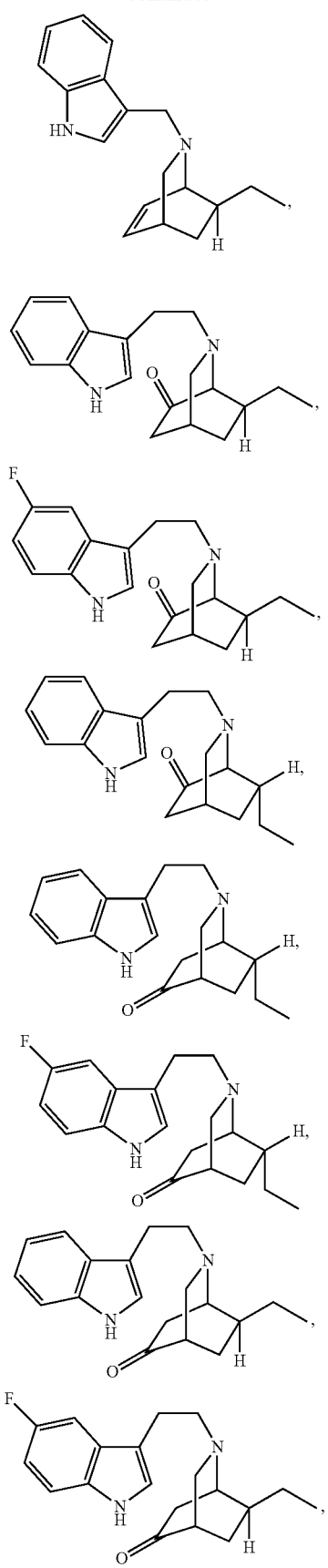

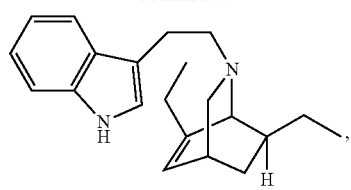
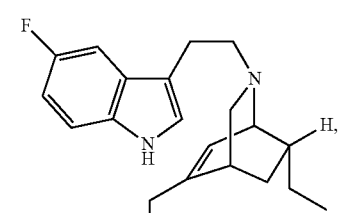
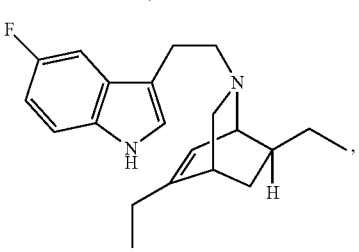
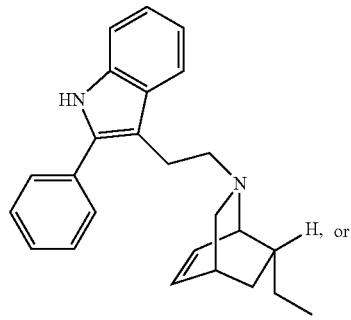
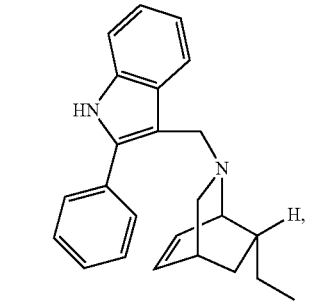
or a pharmaceutically acceptable salt, diastereomer, or enantiomer thereof.
15. The compound of claim 1, wherein the structure is
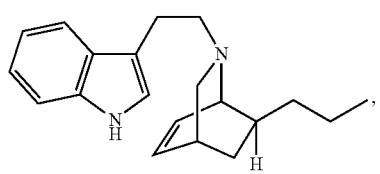
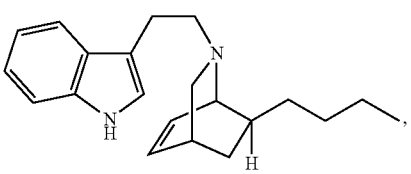
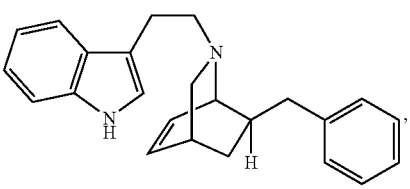
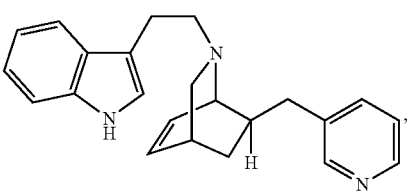
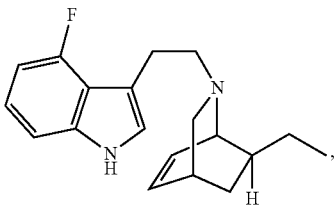
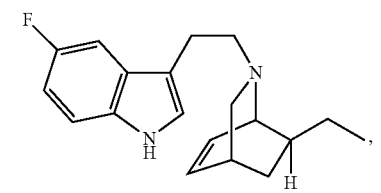
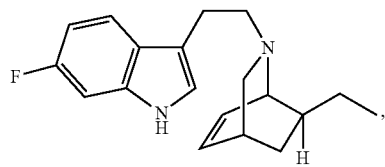
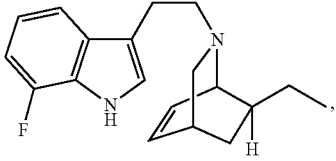
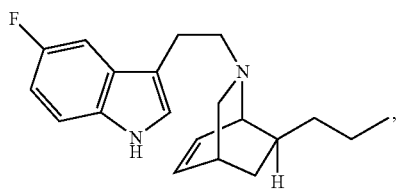
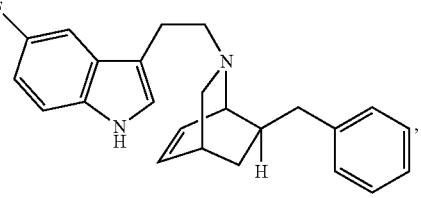

119
-continued

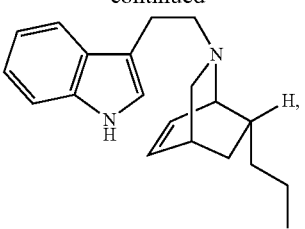

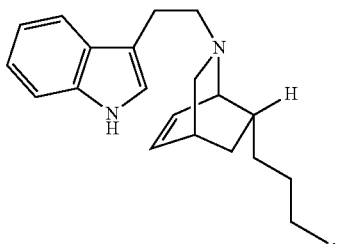

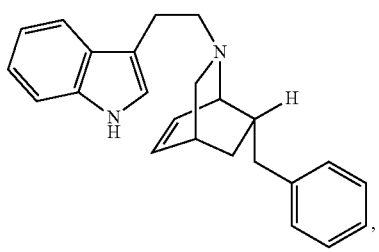

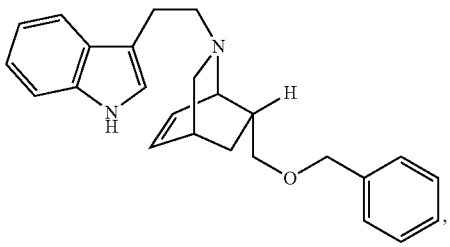

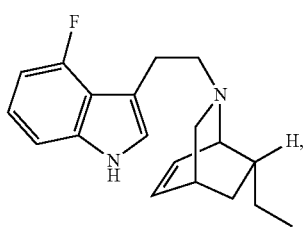

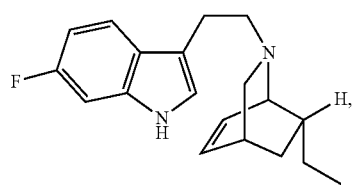

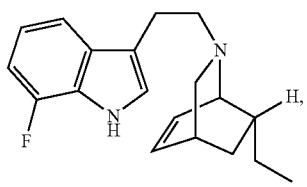

120
-continued

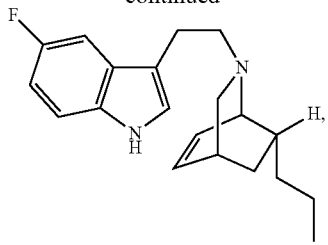

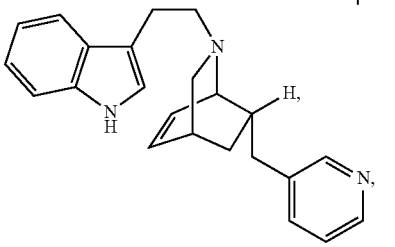

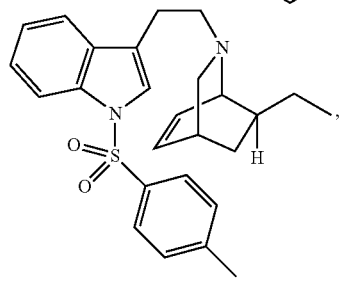

or a pharmaceutically acceptable salt, diastereomer, or enantiomer thereof.

16. A method for inducing a neural cell to release Glial cell-derived neurotrophic factor (GDNF) comprising contacting the cell with a compound of the structure:

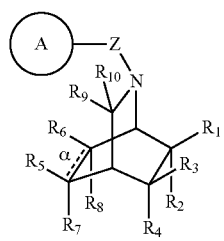

wherein
A is a ring structure, with or without substitution;
Z is present or absent and when present is

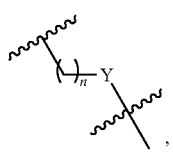

wherein
n is 0, 1, 2, 3, or 4;
Y is —CH$_2$—;
$R_1$, $R_2$, $R_3$, $R_4$, $R_5$ and $R_6$ are independently H, substituted or unsubstituted alkyl, substituted or unsubstituted aryl, substituted or unsubstituted heteroalkyl, substituted or unsubstituted heteroaryl, hydroxyl, amino, ester or amide;

α represents a bond, which is present or absent and when α is present, then $R_7$ and $R_8$ are absent;

$R_7$ and $R_8$ are present when α is absent and $R_5$ and $R_7$ combine to form a carbonyl or $R_6$ and $R_8$ combine to form a carbonyl;

$R_9$ and $R_{10}$ are each hydrogen;

when α is present, Z is

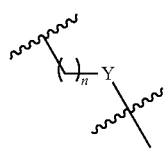

where n=1, Y is —CH$_2$—, A is unsubstituted indole attached at the 3-position of the indole, $R_3$, $R_4$, $R_5$, $R_6$, $R_9$ and $R_{10}$ are each H, and one of $R_1$ or $R_2$ is H, then the other one of $R_1$ or $R_2$ is other than ethyl ester; and wherein the ring structure A is an indole, or a pharmaceutically acceptable salt, diastereomer, or enantiomer thereof.

17. A process for producing the compound of claim 1 comprising:

(i) (a) contacting a compound of the structure:

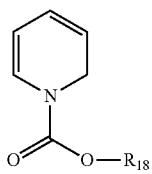

wherein $R_{18}$ is alkyl or benzyl, with methyl vinyl ketone so as to produce a mixture of exo and endo compounds of the structure:

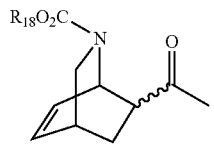

(b) reacting the product of step (a) with tosylhydrazine in a first suitable solvent so as to produce a mixture of exo and endo compounds of the structure:

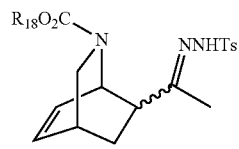

(c) separating the endo and exo products of step (b) by chromatography, and reacting each product with a reducing agent in a second suitable solvent to produce compounds of the structures:

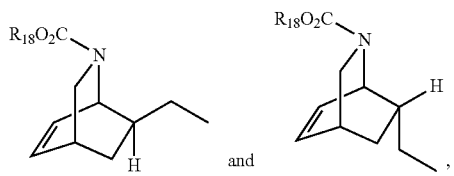

or (ii) (a) contacting a compound of the structure:

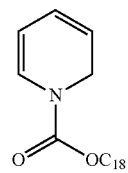

with ethyl acrylate so as to produce a mixture of exo and endo compounds of the structure:

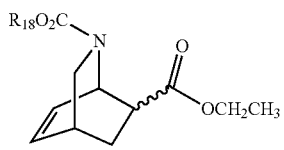

(b) reacting the product of step (a) with lithium hydroxide to produce the corresponding acid followed by reacting the acid with N,O-dimethylhydroxylamine in the presence of 1-ethyl-3-(3-dimethylaminopropyl) carbodiimide in a first suitable solvent so as to produce a mixture of exo and endo compounds of the structure:

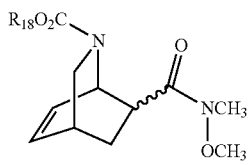

(c) reacting the product of step (b) with $R_{19}$MgBr in a ethereal solvent so as to produce a mixture of exo and endo compounds of the structure:

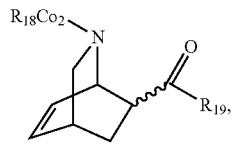

wherein $R_{19}$ is alkyl, (d) reacting the product of step (a) with tosylhydrazine in a first suitable solvent so as to produce a mixture of exo and endo compounds of the structures:

123

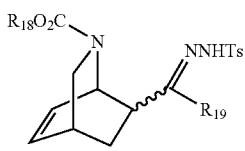

(c) separating the endo and exo products of step (b) by chromatography, and reacting each product with a reducing agent in a second suitable solvent to produce compounds of the structures:

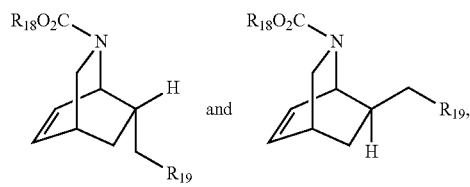

or (iii) (a) contacting a compound of the structure:

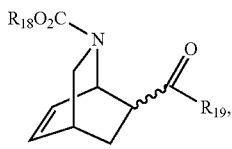

wherein $R_{19}$ aryl or heteroaryl, with a reducing agent to produce a mixture of exo and endo compounds of the structure:

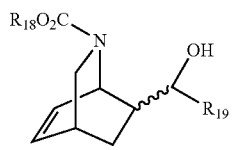

(b) reacting the product of step (a) with iodine, triphenylphosphine, and imidazole in a first suitable solvent so as to produce a mixture of exo and endo compounds of the structure:

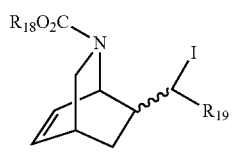

(c) reacting the product of step (b) with a reducing agent in a second suitable solvent so as to produce a mixture of exo and endo compounds of the structure:

124

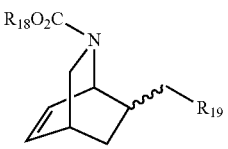

(d) separating the endo and exo products of step (c) by chromatography to produce compounds of the structures:

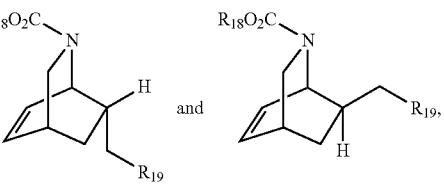

or (iv) (a) contacting a compound of the structure:

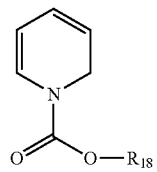

with acrolein in the presence of trifluoroacetic acid and

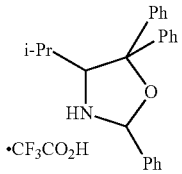 [SMILES: "·CF3CO2H" ; CC(C)C1NC(c2ccccc2)OC1(c1ccccc1)c1ccccc1]

so as to produce the compound of the structure:

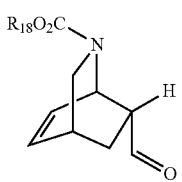

(b) reacting the product of step (a) with sodium methoxide in methanol followed by a reducing agent in a second suitable solvent so as produce a mixture of exo and endo compounds of the structure

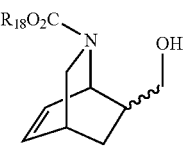

(c) separating the endo and exo products of step (b) by chromatography to produce compounds of the structure:

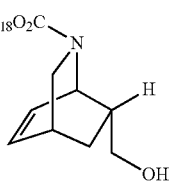 and 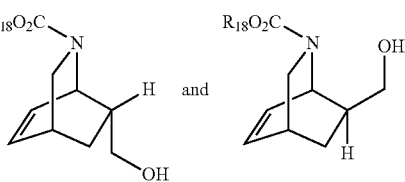

(d) reacting either product of step (c) with an alkyl halide or substituted alkyl halide in the presence of a base to produce a compound of the structure

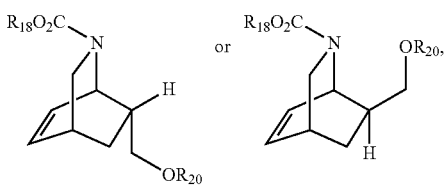

or (v) (a) reacting either of the following compounds:

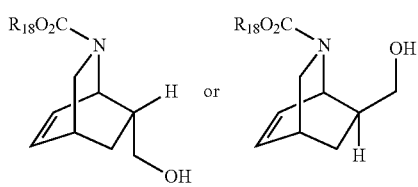

with trifluoromethanesulfonic anhydride in a basic solvent to produce either of the following compounds:

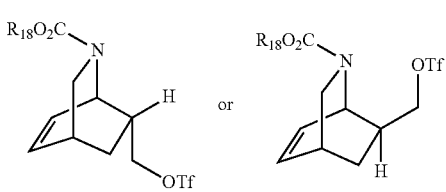

b) reacting either product of step (a) with $Li_2CuCl_4$, and $R_{21}MgBr$ in a ethereal solvent so as to produce either of the following compounds:

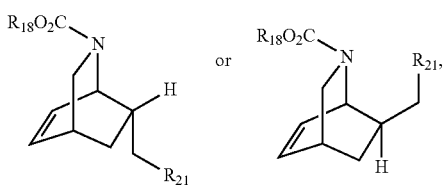

wherein $R_{21}$ is alkyl, aryl or heteroaryl, or (vi) (a) contacting a compound of the structure:

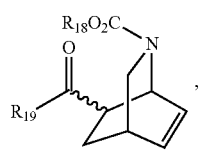

wherein $R_{19}$ is alkyl, with hydrogen in the presence of palladium on carbon in a first suitable solvent to produce a mixture of exo and endo compounds of the structure:

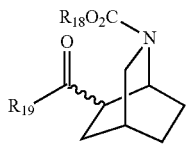

(b) reacting the product of step (a) with 3-chloroperoxybenzoic acid and $Sc(OTf)_3$ in a second suitable solvent so as to produce a mixture of exo and endo compounds of the structures:

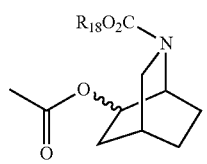

(c) reacting the product of step (b) with lithium hydroxide followed by an oxidizing agent so as to produce a compound of the structure

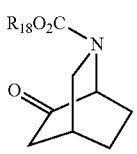

(d) reacting the product of step (c) with lithium bis(trimethylsilyl)amide followed by $Ph-N(OTf)_2$ so as to produce a compound of the structure:

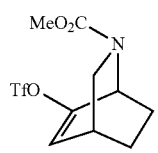 [SMILES: COC(=O)N1CC2C=C(OS(=O)(=O)C(F)(F)F)C1CC2]

(e) reacting the product of step (d) with $CuBr \cdot SMe_2$ and $R_{21}MgBr$ in a ethereal solvent so as to produce a compound of the structure

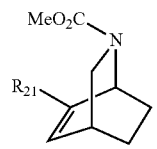

wherein $R_{21}$ is alkyl, aryl or heteroaryl; or (vii) (a) contacting a compound of the structure:

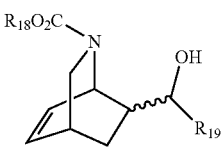

with p-toluoyl chloride in the presence of tetramethylethylenediamine in a first suitable solvent so as to produce a mixture of exo and endo compounds of the structure:

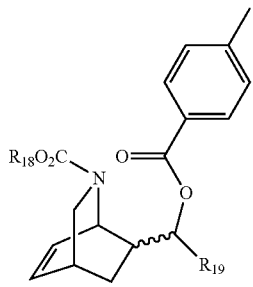

(b) reacting the product of step (a) with a samarium iodide in the presence of hexamethylphosphoramide in a second suitable solvent so as to produce a mixture of exo and endo compounds of the structure:

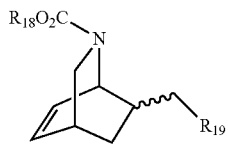

(c) separating the endo and exo products of step (b) by chromatography to produce compounds of the structures:

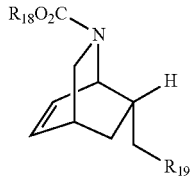 and 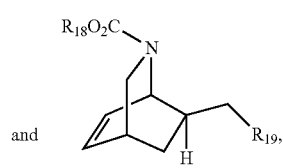

and
(viii) deprotecting the carbamate of the product of any of steps (i)-(vii) with TMSI or HBr/AcOH followed by reacting the deprotected amine with:
a compound of the structure

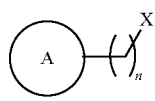

wherein X is a halide,
in the presence of a base, or

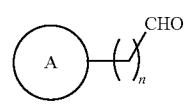

in the presence of a reducing agent and an acid,
wherein A is a ring structure, with or without substitution; and n is 0, 1, 2, 3, or 4,
wherein the ring structure A is an indole;
so as to thereby produce the compound of claim 1.

18. A pharmaceutical composition comprising the compound of claim 1 and a pharmaceutically acceptable carrier.

19. A method for inducing a neural cell to release Glial cell-derived neurotrophic factor (GDNF) comprising contacting the cell with the compound of claim 1 so as to thereby induce the neural cell to release Glial cell-derived neurotrophic factor (GDNF).

20. The compound of claim 9 of the structure:

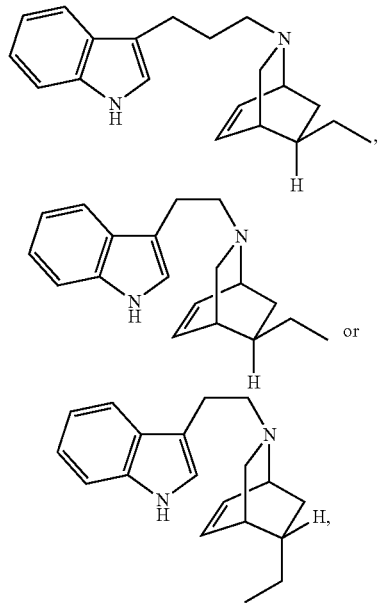

or a pharmaceutically acceptable salt, diastereomer, or enantiomer thereof.

21. A pharmaceutical composition comprising the compound of claim 9 and a pharmaceutically acceptable carrier.

22. A method for inducing a neural cell to release Glial cell-derived neurotrophic factor (GDNF) comprising contacting the cell with the compound of claim 9 so as to thereby induce the neural cell to release Glial cell-derived neurotrophic factor (GDNF).

23. The compound of claim 1,
wherein
α represents a bond, which is present; and
$R_9$ and $R_{10}$ are each hydrogen,
or a pharmaceutically acceptable salt, diastereomer, or enantiomer thereof.

24. The compound of claim 1,
wherein
$R_3$ and $R_4$ are each H;
$R_5$ and $R_6$ are each H;
α represents a bond, which is present; and
$R_9$ and $R_{10}$ are each hydrogen,
or a pharmaceutically acceptable salt, diastereomer, or enantiomer thereof.

25. The compound of claim 1,
wherein
$R_1$ is H and $R_2$ is substituted or unsubstituted alkyl, substituted or unsubstituted aryl, substituted or unsubstituted heteroalkyl, substituted or unsubstituted heteroaryl, unsubstituted hydroxyl, amino, or amide, or $R_2$ is H and $R_1$ is substituted or unsubstituted alkyl, substituted or unsubstituted aryl, substituted or unsubstituted heteroalkyl, substituted or unsubstituted heteroaryl, unsubstituted hydroxyl, amino, or amide;
wherein each substituted alkyl or heteroalkyl is substituted with aryl or heteroaryl, or a pharmaceutically acceptable salt, diastereomer, or enantiomer thereof.

26. A compound of the structure:

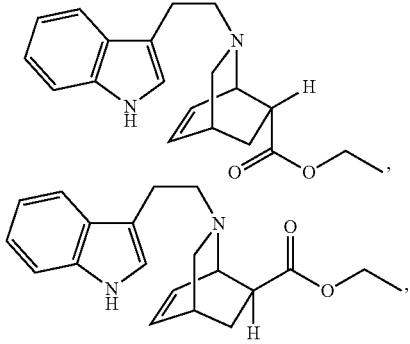

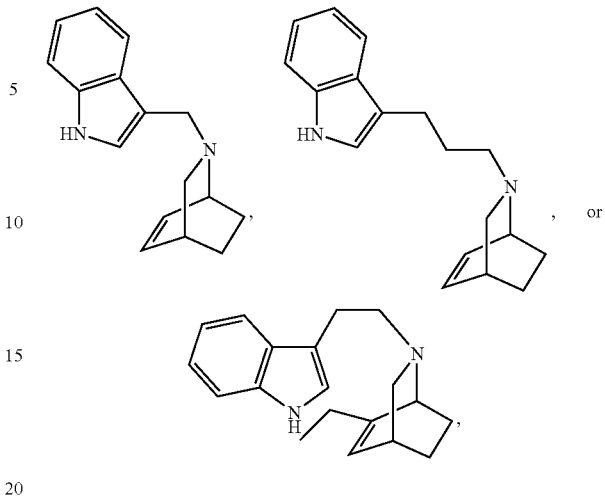

or a pharmaceutically acceptable salt, diastereomer, or enantiomer thereof.

* * * * *